US012570805B2

(12) United States Patent
Pan et al.

(10) Patent No.: US 12,570,805 B2
(45) Date of Patent: Mar. 10, 2026

(54) SYNTHESIS OF OLIGOSACCHARIDES AS PREBIOTICS FROM SIMPLE SUGARS AND POLYSACCHARIDES IN CONCENTRATED ACIDS

(71) Applicant: Wisconsin Alumni Research Foundation, Madison, WI (US)

(72) Inventors: Xuejun Pan, Madison, WI (US); Meijun Zeng, Madison, WI (US); Ning Li, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 845 days.

(21) Appl. No.: 17/832,490

(22) Filed: Jun. 3, 2022

(65) Prior Publication Data

US 2022/0389172 A1 Dec. 8, 2022

Related U.S. Application Data

(60) Provisional application No. 63/197,041, filed on Jun. 4, 2021.

(51) Int. Cl.
| | |
|---|---|
| *C08H 8/00* | (2010.01) |
| *C07H 1/08* | (2006.01) |
| *C07H 3/06* | (2006.01) |

(52) U.S. Cl.
CPC ................. *C08H 8/00* (2013.01); *C07H 1/08* (2013.01); *C07H 3/06* (2013.01)

(58) Field of Classification Search
CPC ............... C08H 8/00; C07H 1/08; C07H 3/06
USPC ........................................................... 530/502
See application file for complete search history.

(56) References Cited

U.S. PATENT DOCUMENTS

2019/0194239 A1* 6/2019 Pan .......................... C08H 8/00

FOREIGN PATENT DOCUMENTS

WO WO-2011035978 A1 * 3/2011 ............. C08B 30/12

OTHER PUBLICATIONS

Reinoso et al., WO 2011/035978 A1 machine translation in English, Mar. 31, 2011. (Year: 2011).*
Sathitsuksanoh et al., "Cellulose solvent-based pretreatment for corn stover and avicel: concentrated phosphoric acid versus ionic liquid," Cellulose, 19(4):1161-1172 (2012).

* cited by examiner

*Primary Examiner* — David T Karst
(74) *Attorney, Agent, or Firm* — Foley & Lardner LLP

(57) ABSTRACT

Provided herein are methods for preparing a product including predominantly prebiotic oligosaccharides by non-enzymatic methods of glycosylation of monosaccharides, disaccharides, and/or polysaccharides. The methods may include mixing one or more types of monosaccharides, disaccharides, and/or polysaccharides with an effective amount of a dehydrating acid at a temperature sufficient to form a product including predominantly prebiotic oligosaccharides.

20 Claims, 45 Drawing Sheets

Short-chain fatty acid production in oligosaccharide fermentation broth by *Lactobacillus* strains

| Acid conc. (g/L) | Strain | GlOS_H₂SO₄ | | GOS1 | | GOS2 | | FOS1 | | FOS2 | |
|---|---|---|---|---|---|---|---|---|---|---|---|
| | | Oligo. | Control | Oligo. | Control | Oligo. | Control | Oligo. | Control | Oligo. | Control |
| Lactic acid (LA) | L. reuteri | 1.57 | 1.50 | 2.17 | 1.26 | 1.39 | 1.15 | 1.97 | 1.11 | 2.57 | 2.20 |
| | L. casei | 4.22 | 3.64 | 3.27 | 2.99 | 2.65 | 2.87 | 4.40 | 4.42 | 5.53 | 4.99 |
| | L. GG | 3.37 | 3.17 | 2.36 | 2.38 | 2.42 | 2.25 | 4.14 | 4.06 | 5.39 | 4.71 |
| | L. gasseri | 2.95 | 2.47 | 1.91 | 1.99 | 2.19 | 1.94 | 2.66 | 3.87 | 5.41 | 4.68 |
| Formic acid (FA) | L. reuteri | 0.02 | 0.02 | 0.01 | 0.02 | 0.01 | 0.02 | 0.02 | 0.02 | 0.01 | 0.02 |
| | L. casei | 0.03 | 0.08 | 0.16 | 0.16 | 0.16 | 0.15 | 0.01 | 0.01 | 0.01 | 0.01 |
| | L. GG | 0.23 | 0.25 | 0.27 | 0.27 | 0.26 | 0.26 | 0.11 | 0.11 | 0.06 | 0.07 |
| | L. gasseri | 0.01 | 0.02 | 0.02 | 0.02 | 0.02 | 0.02 | 0.01 | 0.02 | 0.01 | 0.01 |
| Acetic acid (AA) | L. reuteri | 0.52 | 0.51 | 0.55 | 0.52 | 0.50 | 0.48 | 0.50 | 0.49 | 0.63 | 0.56 |
| | L. casei | 1.35 | 1.36 | 1.41 | 1.41 | 1.31 | 1.34 | 0.61 | 0.46 | 0.57 | 0.58 |
| | L. GG | 1.51 | 1.47 | 1.52 | 1.51 | 1.53 | 1.46 | 1.11 | 1.98 | 0.86 | 0.80 |
| | L. gasseri | 0.39 | 0.38 | 0.35 | 0.41 | 0.21 | 0.40 | 0.35 | 0.29 | 0.35 | 0.35 |
| Propionic acid (PA) | L. reuteri | 0.25 | 0.24 | 0.30 | 0.22 | 0.23 | 0.23 | 0.03 | 0.22 | 0.39 | 0.33 |
| | L. casei | 0.18 | 0.17 | 0.22 | 0.17 | 0.16 | 0.16 | 0.16 | 0.17 | 0.17 | 0.15 |
| | L. GG | 0.24 | 0.19 | 0.18 | 0.18 | 0.22 | 0.23 | 0.21 | 0.18 | 0.18 | 0.18 |
| | L. gasseri | 0.18 | 0.21 | 0.28 | 0.19 | 0.18 | 0.17 | 0.18 | 0.17 | 0.19 | 0.18 |
| Butyric acid (BA) | L. reuteri | 0.10 | 0.10 | 0.10 | 0.09 | 0.08 | 0.08 | 0.09 | 0.09 | 0.10 | 0.09 |
| | L. casei | 0.12 | 0.11 | 0.11 | 0.11 | 0.10 | 0.11 | 0.09 | 0.10 | 0.11 | 0.11 |
| | L. GG | 0.12 | 0.11 | 0.11 | 0.10 | 0.10 | 0.09 | 0.11 | 0.09 | 0.12 | 0.10 |
| | L. gasseri | 0.08 | 0.08 | 0.07 | 0.08 | 0.07 | 0.08 | 0.08 | 0.07 | 0.08 | 0.08 |

L: Glcβ(1→3)Glc linkage

Tr: Glc(1→1)Glc linkage

N: Glcα(1→3)Glc linkage

M: Glcα(1→4)Glc linkage

G: Glcβ(1→6)Glc linkage

S: Glcβ(1→2)Glc linkage

: Glcα(1→6)Glc linkage

K: Glcα(1→2)Glc linkage

FIG. 13 (Cont.)

Short-chain fatty acid production in oligosaccharide fermentation broth by *Lactobacillus* strains

| Acid conc. (g/L) | Strain | GlOS_H₂SO₄ | | GOS1 | | GOS2 | | FOS1 | | FOS2 | |
|---|---|---|---|---|---|---|---|---|---|---|---|
| | | Oligo. | Control | Oligo. | Control | Oligo. | Control | Oligo. | Control | Oligo. | Control |
| Lactic acid (LA) | L. reuteri | 1.57 | 1.50 | 2.17 | 1.26 | 1.39 | 1.15 | 1.07 | 1.11 | 2.57 | 2.20 |
| | L. casei | 4.22 | 3.64 | 3.27 | 2.99 | 2.65 | 2.87 | 4.40 | 4.42 | 5.82 | 4.99 |
| | L. GG | 3.37 | 3.17 | 2.36 | 2.38 | 2.42 | 2.25 | 4.14 | 4.06 | 5.39 | 4.71 |
| | L. gasseri | 2.95 | 2.47 | 1.91 | 1.99 | 2.19 | 1.94 | 2.66 | 2.87 | 5.41 | 4.68 |
| Formic acid (FA) | L. reuteri | 0.02 | 0.02 | 0.01 | 0.02 | 0.01 | 0.02 | 0.02 | 0.02 | 0.01 | 0.02 |
| | L. casei | 0.03 | 0.08 | 0.16 | 0.16 | 0.16 | 0.15 | 0.01 | 0.01 | 0.01 | 0.01 |
| | L. GG | 0.23 | 0.25 | 0.27 | 0.27 | 0.26 | 0.26 | 0.11 | 0.11 | 0.06 | 0.07 |
| | L. gasseri | 0.01 | 0.02 | 0.02 | 0.02 | 0.02 | 0.02 | 0.01 | 0.02 | 0.01 | 0.01 |
| Acetic acid (AA) | L. reuteri | 0.52 | 0.51 | 0.55 | 0.52 | 0.50 | 0.46 | 0.50 | 0.49 | 0.63 | 0.56 |
| | L. casei | 1.35 | 1.36 | 1.41 | 1.41 | 1.31 | 1.34 | 0.61 | 0.46 | 0.57 | 0.58 |
| | L. GG | 1.51 | 1.47 | 1.52 | 1.51 | 1.53 | 1.46 | 1.11 | 1.08 | 0.86 | 0.80 |
| | L. gasseri | 0.39 | 0.38 | 0.35 | 0.41 | 0.21 | 0.40 | 0.35 | 0.29 | 0.35 | 0.35 |
| Propionic acid (PA) | L. reuteri | 0.25 | 0.24 | 0.30 | 0.22 | 0.23 | 0.23 | 0.03 | 0.22 | 0.39 | 0.33 |
| | L. casei | 0.18 | 0.17 | 0.22 | 0.17 | 0.16 | 0.16 | 0.16 | 0.17 | 0.17 | 0.15 |
| | L. GG | 0.24 | 0.19 | 0.18 | 0.18 | 0.22 | 0.23 | 0.21 | 0.18 | 0.18 | 0.18 |
| | L. gasseri | 0.18 | 0.21 | 0.28 | 0.19 | 0.18 | 0.17 | 0.18 | 0.17 | 0.19 | 0.18 |
| Butyric acid (BA) | L. reuteri | 0.10 | 0.10 | 0.10 | 0.09 | 0.08 | 0.08 | 0.09 | 0.09 | 0.10 | 0.09 |
| | L. casei | 0.12 | 0.11 | 0.11 | 0.11 | 0.10 | 0.11 | 0.09 | 0.10 | 0.11 | 0.11 |
| | L. GG | 0.12 | 0.11 | 0.11 | 0.10 | 0.10 | 0.09 | 0.11 | 0.09 | 0.12 | 0.10 |
| | L. gasseri | 0.08 | 0.08 | 0.07 | 0.08 | 0.07 | 0.08 | 0.08 | 0.07 | 0.08 | 0.08 |

FIG. 14

Mano- and disaccharides in oligosaccharide fermentation broth by *Lactobacillus* strains after 24 h

| Sugar | Strain | GOS_H₂SO₄ | | | GOS1 | | | GOS2 | | | FOS1 | | | FOS2 | | |
|---|---|---|---|---|---|---|---|---|---|---|---|---|---|---|---|---|
| | | Oligo. | Control | 0 h | Oligo. | Control | 0 h | Oligo. | Control | 0 h | Oligo. | Control | 0 h | Oligo. | Control | 0 h |
| Glucose | L. reuteri | 0.00 | 0.00 | | 0.00 | 0.00 | | 0.01 | 0.00 | | 0 | 0 | | 0.02 | 0.00 | |
| | L. casei | 0.00 | 0.00 | | 0.00 | 0.00 | | 0.00 | 0.00 | | 0 | 0 | 0 | 0.01 | 0.00 | 2.24 |
| | L. GG | 0.00 | 0.00 | 0.81 | 0.00 | 0.00 | 0.00 | 0.01 | 0.00 | 0.03 | 0 | 0 | 0 | 0.01 | 0.06 | |
| | L. gasseri | 0.00 | 0.00 | | 0.00 | 0.00 | | 0.02 | 0.00 | | 0 | | | 0.01 | 0.00 | |
| Galactose | L. reuteri | | | | 0.01 | 0.00 | | 0.02 | 0.00 | | | | | | | |
| | L. casei | | | | 0.00 | 0.00 | 0.17 | 0.00 | 0.00 | 0.06 | | | | | | |
| | L. GG | | | | 0.04 | 0.07 | | 0.02 | 0.03 | | | | | | | |
| | L. gasseri | | | | 0.01 | 0.00 | | 0.01 | 0.00 | | | | | | | |
| | L. reuteri | | | | 0.05 | 0.00 | | 0.14 | 0.00 | | | | | | | |
| Lactose | L. casei | | | | 0.09 | 0.00 | 0.00 | 0.14 | 0.00 | 0.00 | | | | | | |
| | L. GG | | | | 0.17 | 0.05 | | 0.25 | 0.05 | | | | | | | |
| | L. gasseri | | | | 0.16 | 0.03 | | 0.21 | 0.04 | | | | | | | |
| Fructose | L. reuteri | | | | | | | | | | 2.05 | 1.72 | | 0.41 | 0.26 | |
| | L. casei | | | | | | | | | | 0.08 | 0.08 | 2.23 | 0.71 | 0.09 | 0.8 |
| | L. GG | | | | | | | | | | 0.05 | 0.05 | | 0.71 | 0.06 | |
| | L. gasseri | | | | | | | | | | 1.21 | 0.82 | | 0.73 | 0.05 | |
| | L. reuteri | | | | | | | | | | 0 | 0 | | 0.00 | 0.00 | |
| Sucrose | L. casei | | | | | | | | | | 0 | 0 | 0 | 0.10 | 0.14 | 0.18 |
| | L. GG | | | | | | | | | | 0 | 0 | | 0.10 | 0.15 | |
| | L. gasseri | | | | | | | | | | 0 | 0 | | 0.00 | 0.00 | |

Sugar concentration (g/L)

FIG. 15

Molecular weight: derivatized GIOS (Da)

SYNTHESIS OF OLIGOSACCHARIDES AS PREBIOTICS FROM SIMPLE SUGARS AND POLYSACCHARIDES IN CONCENTRATED ACIDS

CROSS-REFERENCE TO RELATED APPLICATIONS

This application claims the benefit of priority to U.S. Provisional Patent Application Ser. No. 63/197,041, filed on Jun. 4, 2021, the entire disclosure of which is hereby incorporated by reference herein.

GOVERNMENT RIGHTS

This invention was made with government support under 23-CRHF-0-6055 awarded by the USDA/NIFA. The government has certain rights in the invention.

FIELD

The present technology relates to non-enzymatic methods of preparing prebiotic oligosaccharides from monosaccharides, disaccharides, and/or polysaccharides using an effective amount of dehydrating acid.

BACKGROUND

Certain oligosaccharides which are indigestible by humans may nevertheless serve as food for probiotic microorganisms and promote human health. Such oligosaccharides are known as prebiotic oligosaccharides. Oligosaccharides are oligomers of sugar monomer units (monosaccharides) linked by glycosidic bonds with degrees of polymerization (DP) from 2 to 10 or in some cases up to 20. Examples of prebiotic oligosaccharides include glucooligosaccharides (GlOS or GlcOS), fructooligosaccharides (FOS), galactooligosaccharides (GaOS or GOS), xylooligosaccharides (XOS), maltooligosaccharides, isomaltooligosaccharides (IMO), mannooligosaccharides, cellooligosaccharides, and pecticoligosaccharides (POS). Passing through the upper gastrointestinal tract intact, prebiotic oligosaccharides can be selectively metabolized by the beneficial bacteria in the colon, thus modulating the composition and/or activity of the gut microbiota and resulting in improvement to host health. The direct physiological benefits encompass stimulation of probiotic population such as *Bifidobacterium* and *Lactobacillus* strains and accumulation of metabolic end products, such as short-chain fatty acid (SCFA) in the colon. Besides the direct benefits above to hosts, a range of systemic health implications are recognized, including metabolic inhibition of pathogenic microorganisms, constipation alleviation, reduction of diet-induced obesity, improvement of mineral absorption, repression of allergic symptoms, enhancement of immune system, reduction of colon cancer, and modulation of cholesterol levels. The bioactivities and prebiotic functionalities of oligosaccharides depend on their sugar compositions, DP value, and glycosidic linkages.

At present, prebiotics are generally produced through either controlled hydrolysis of polysaccharides or direct synthesis from simple sugars. Methods using controlled hydrolysis of polysaccharides are limited by the starting polysaccharides since sugar compositions and glycosidic linkages of the oligosaccharides are mostly inherited from the parent polysaccharides and their supplies are limited. Enzymatic hydrolysis can be expensive and suitable enzymes of limited availability. Acid hydrolysis is cheaper, but often induces sugar degradation and result in undesirable side-products. Synthesis of oligosaccharides from simple sugars using enzymes is also an expensive and problematic process in view of the challenges of identifying and synthesizing enzymes with high activity and selectivity, good stability and recyclability, low cost, and industrial feasibility. Non-enzymatic catalysts, especially acids, can also catalyze the glycosylation. However, challenges remain to prepare oligosaccharides with the degree of polymerization (DP)>2 while avoiding sugar degradation and other undesired byproducts.

SUMMARY

The present technology provides methods for preparing a product that predominantly includes prebiotic oligosaccharides by non-enzymatic glycosylation of monosaccharides, disaccharides, and/or polysaccharides. Thus, in one aspect, the present technology provides methods including reacting a mixture including one or more types of monosaccharides, disaccharides, and/or polysaccharides and about 40 to about 98 wt % of dehydrating acid to provide a product that predominantly includes prebiotic oligosaccharides, wherein the mixture is reacted at a temperature of about 10° C. to about 160° C.

In another aspect the present technology provides methods of preparing a product including predominantly prebiotic oligosaccharides including reacting a mixture comprising about 1 wt % to about 90 wt % of one or more types of monosaccharides, disaccharides, and/or polysaccharides and an effective amount of a dehydrating acid; wherein the mixture is reacted at a temperature of about 10° C. to about 160° C.

In another aspect the present technology provides methods of preparing a product including predominantly prebiotic oligosaccharides including reacting one or more types of monosaccharides, disaccharides, polysaccharides or a combination of two or more thereof in a solution comprising an effective amount of sulfuric or phosphoric acid at a temperature sufficient to form a sugar mixture comprising predominantly prebiotic oligosaccharides.

The foregoing summary is illustrative only and is not intended to be in any way limiting. In addition to the illustrative aspects, embodiments and features described above, further aspects, embodiments and features will become apparent by reference to the following drawings and the detailed description.

BRIEF DESCRIPTION OF THE DRAWINGS

(FIG. 1A) residual glucose yield; (FIG. 1B) GlOS yield; (FIG. 1C) GlOS selectivity; (FIG. 1D) IM and GB yield; (FIG. 1E) LGA yield; (FIG. 1F) HMF yield.

FIG. 14 shows short-chain fatty acid production in oligosaccharide fermentation broth by *Lactobacillus* strains. GlOS-$H_2SO_4$ denotes the oligosaccharides synthesized from glucose in 72% $H_2SO_4$; GOS1 and GOS2 denote the oligosaccharides synthesized from galactose and lactose, respectively, in ALBTH; FOS1 and FOS2 denote the oligosaccharides synthesized from fructose and sucrose, respectively, in ALBTH. The oligosaccharide samples contained 10 g/L sugars. The control samples were of the same monosaccharide concentration with the oligosaccharide samples.

FIG. 15 shows mono- and disaccharides in oligosaccharide fermentation broth by *Lactobacillus* strains after 24 h.

(FIG. 21A) permeate flux (FIG. 21B) observed rejection values as a function of volume concentration ratio.

(FIG. 22A) permeate flux and the observed rejection of $H_2SO_4$; (FIG. 22B) observed rejection of glucose, cellobiose, raffinose and stachyose. The initial feed concentration of glucose, cellobiose, raffinose and stachyose was 0.33 g/L, 0.44 g/L, 0.53 g/L and 0.32 g/L, respectively.

(FIG. 23A) residual glucose yield; (FIG. 23B) GlcOS yield; (FIG. 23C) isomaltose yield; (FIG. 23D) gentiobiose yield. The initial glucose loading is 20% (w/w).

DETAILED DESCRIPTION

Figure 1A:
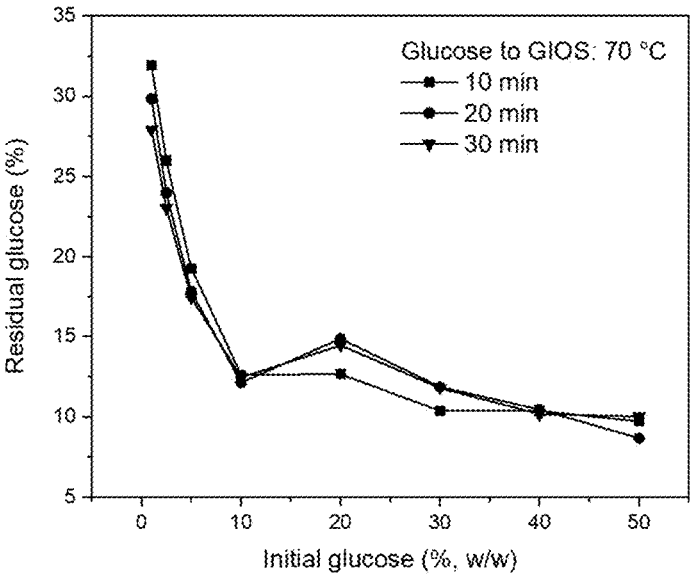
FIGS. 1A-1F show the effect of initial glucose concentration (1-50%, w/w) on GlOS synthesis from glucose glycosylation in 72 wt % wt $H_2SO_4$ at 70° C.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The following terms are used throughout as defined below. All other terms and phrases used herein have their ordinary meanings as one of skill in the art would understand.

As used herein, singular articles such as "a", "an", and "one" are intended to refer to singular or plural. As such, this statement is intended to serve as antecedent basis for use of such exclusive terminology as "solely," "only," and the like in connection with the recitation of claim elements, or use of a "negative" limitation.

The term "about" can refer to a variation of up to ±5% of the value specified. For example, "about 50" can in some embodiments carry a variation from 45 to 55 percent. In other embodiments, "about" can refer to a variation of ±1%, ±2%, or ±3%. Unless indicated otherwise herein, the term "about" is intended to include values, e.g., weight percentages, proximate to the recited range that are equivalent in terms of the functionality of the individual ingredient, the composition, or the embodiment. In addition, unless indicated otherwise herein, a recited range (e.g., weight percentages) includes each specific value, integer, decimal, or identity within the range.

The term "and/or" means any one of the items, any combination of the items, or all of the items with which this term is associated.

As used herein, values of wt % refer to the percentage weight of the individual component based on the weight of the total composition. For example, wt % of dehydrating acid in a mixture (or solution) is the amount of dehydrating acid by weight divided by the total weight of the mixture (or solution), where the resulting fraction is multiplied by 100%. Those of skill in the art will understand that all values of wt % herein are calculated in an analogous fashion.

The present technology provides methods of preparing prebiotic oligosaccharides via non-enzymatic glycosylation of monosaccharides, disaccharides, polysaccharides, and combinations of two or more thereof. As noted above, "oligosaccharides," as that term is used herein, may have from 2 to 20 monosaccharide residues, joined to each other by glycosidic bonds. Monosaccharides have from 3 to 8 carbons, i.e., 3, 4, 5, 6 7, 8 or a range between and including any two of the foregoing values (e.g., 3-6 or 5-6 carbons). "Polysaccharides," as that term is used herein, include at least 50 monosaccharide residues, joined to each other by glycosidic bonds. In certain embodiments, the polysaccharide includes at least 100, at least 300, at least 500, or at least 800 monosaccharide residues, joined to each other by glycosidic bonds. Polysaccharides, in some embodiments may have up to 10,000, up to 5,000, up to 3,000, up to 2,000, up to 1,000, or up to 500 monosaccharide residues, joined to each other by glycosidic bonds.

Oligosaccharides may be characterized according to their DP, which refers to the number of monosaccharide residues that make up a particular oligosaccharide. Thus, a disaccharide has a DP of 2, whereas an oligosaccharide having 20 residues has a DP of 20. Prebiotic oligosaccharides of the present technology may have a variety of lengths (e.g., a DP of 2, 3, 4, 5, 6, 7, 8, 9, 10, 11, 12, 13, 14, 15, 16, 17, 18, 19, 20 or a range between and including any two of the foregoing values). For example, in any embodiments herein, the prebiotic oligosaccharides may have a DP of 2-10 or 3-10 residues. Such oligosaccharides are typically water soluble (i.e., have a solubility>1 mg/mL in water at 25° C.).

The DP of the various saccharides in the compositions of the invention may be measured using gel permeation chromatography (GPC), matrix-assisted laser desorption/ionization time-of-flight (MALDI-TOF) mass spectrometry, or other conventional molecular weight determination methods. Oligosaccharides with a certain DP can be identified and quantitated using HPLC (such as DIONEX with an electrochemical detector) by comparing with the standard saccharides. An average DP for mixtures of oligosaccharides may also be calculated based on mass spectrometry or other analytical techniques known in the art.

In one aspect, the methods of the present technology include reacting a mixture of one or more types of monosaccharides, disaccharides, and/or polysaccharides and about 40 to about 98 wt % of a dehydrating acid to provide a product that predominantly includes prebiotic oligosaccharides. In another aspect, the methods of the present technology include reacting a mixture comprising about 1 wt % to about 90 wt % of one or more types of monosaccharides, disaccharides, and/or polysaccharides and an effective amount of a dehydrating acid to provide a product that predominantly includes prebiotic oligosaccharides. In another aspect, the methods of the present technology include reacting one or more types of monosaccharides, disaccharides, and/or polysaccharides in a solution comprising an effective amount of sulfuric or phosphoric acid at a temperature sufficient to form a sugar mixture comprising predominantly prebiotic oligosaccharides. In any aspect or embodiment, the methods may further include reacting the mixture at a temperature of about 10° C. to about 160° C.

As used herein, the term "dehydrating acid" refers to an acid that is sufficiently acidic and can be employed at a concentration sufficient to facilitate the dehydration of sugar units during the formation glycosidic linkages such that the product predominantly includes prebiotic oligosaccharides. The dehydrating acid must also dissolve a sufficient amount of the mixture of monosaccharides, disaccharides, and/or polysaccharides to provide a product which predominantly includes prebiotic oligosaccharides. For example, the dehydrating acid may have a pKa of about −4 to less than 4. Thus, useful acids may have pKas of −4, −3,−2, −1, 0, 1, 2, 3, 4 or a range between and including any two of the foregoing values, e.g., from −3 to 3. In any embodiments, the dehydrating acid may have a pKa of about −3, e.g., −2.8. In any embodiments, the dehydrating acid may have a pKa of about 2, e.g., 2.1. For example, in any aspect or embodiment, the dehydrating acid may be $H_2SO_4$ or may be $H_3PO_4$.

As used herein, the phrase "product predominantly comprising" preceding a component of the product, refers to a product in which the component (e.g., prebiotic oligosaccharides) makes up the largest amount of the product by weight compared to any other species in the product. For example, where the product predominantly comprises prebiotic oligosaccharides, it will be understood that the amount of prebiotic saccharides in the product is larger than the combined amounts of, e.g., any other sugars in the product. Similarly, where the product predominantly comprises prebiotic oligosaccharides that have a DP of at least three, it will be understood that the amount of such oligosaccharides make up the largest percentage by weight of the product. Even if such products also include prebiotic disaccharides, the combined weight of DP 3 or greater oligosaccharides (e.g., those with 3 or more sugar residues) is greater than the combined weight of disaccharides. In any embodiments, the present method provides predominantly prebiotic oligosaccharides with a DP of 3, 4, 5, 6, 7, 8, 9, 10, 11, 12, 13, 14, 15, or a range between and including any two of the foregoing values.

The present methods utilize an effective amount of dehydrating acid, which includes any amount that is sufficient to drive the reaction to provide a product that predominantly comprises prebiotic oligosaccharides. In any aspect or embodiment of the methods, the amount of dehydrating acid used may be about 40 wt % to about 98 wt % of the mixture or solution, including about 40 wt %, about 50 wt %, about 60 wt %, about 64 wt %, about 70 wt %, about 76 wt %, about 80 wt %, about 84 wt %, about 90 wt %, about 92 wt %, about 95 wt %, about 98 wt %, or a range between and including any of the foregoing values. For example, the mixture or solution may include about 60-92 wt % dehydrating acid, about 64-90 wt % dehydrating acid, or about 70 to about 80 wt % dehydrating acid. In some embodiments, the mixture or solution may include about 60 to about 92 wt % dehydrating acid, about 64 to about 90 wt % dehydrating acid, or about 70 to about 80 wt % dehydrating acid. In some embodiments, the mixture or solution may include about 70-90 wt % dehydrating acid, or about 76 wt % dehydrating acid, or about 85 wt % dehydrating acid. Accordingly, the amount of dehydrating acid used in any aspects or embodiments of the methods may be about 60 to about 92 wt % sulfuric acid, 64 to about 84 wt % sulfuric acid, about 76 wt % sulfuric acid, about 70 to about 80 wt % phosphoric acid, about 70 wt % to about 90 wt % phosphoric acid, about 85 wt % phosphoric acid, or about 80 wt % phosphoric acid. In some embodiments, the amount of dehydrating acid used may be about 64 to about 84 wt % sulfuric acid, about 76 wt % sulfuric acid. In any aspects or embodiments, a mixture of sulfuric and phosphoric acid may be used.

In any aspect or embodiment of the present technology, the mixture or solution may include about 1 to about 90 wt % of one or more monosaccharides, disaccharides, and/or polysaccharides. For example, the mixture or solution may include the one or more types of monosaccharides, disaccharides, and/or polysaccharides at 1 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or a range between and including any two of the foregoing values. For example, in any aspects or embodiments, the mixture or solution includes about 1 wt % to about 70 wt %, about 1 wt % to about 50 wt %, about 10 wt % to about 50 wt %, about 30 wt % to about 50 wt %, about 20 to about 60 wt %, about 20 wt % to about 70 wt %, or about 30 wt % to about 70 wt % monosaccharides, disaccharides, and/or polysaccharides.

A wide variety of monosaccharides disaccharides, and/or polysaccharides may be used in the methods of the present technology, including, but not limited to glucose, fructose, galactose, xylose, levoglucosan, mannose, arabinose, sucrose, lactose, maltose, isomaltose, gentiobiose, cellobiose, trehalose, neotrehalose, isotrehalose, kojibiose, sophorose, nigerose, laminaribiose, apiose, rhamnose, hydrolyzed starch, hydrolyzed cellulose, hydrolyzed dextrin, hydrolyzed dextran, hydrolyzed lignocellulosic biomass, cellulose, hemicellulose, corn stover, or a combination of any two or more thereof. By "hydrolyzed starch," "hydrolyzed cellulose" and "hydrolyzed lignocellulosic biomass" is meant a mixture of monosaccharides (or disaccharides and soluble oligosaccharides) comprising 90 wt % or more, respectively, of a starch hydrolysate, cellulose hydrolysate or a lignocellulosic biomass hydrolysate. In any aspects or embodiments, one or more monosaccharides in the mixture or solution may be selected from glucose, fructose, galactose, xylose, levoglucosan, mannose, arabinose, apiose, rhamnose, hydrolyzed starch, hydrolyzed cellulose, hydrolyzed lignocellulosic biomass, and combinations of two or more thereof. In some embodiments of any aspect of the present technology, the monosaccharide may be glucose. In some, the monosaccharide may be galactose. In some, the monosaccharide may be fructose. In some, the monosaccharide may be xylose. In some, the monosaccharide may be mannose. In some, the monosaccharide may be arabinose. In any aspects or embodiments, one or more disaccharides in the mixture or solution may be selected from sucrose, lactose, maltose, isomaltose, gentiobiose, cellobiose, trehalose, neotrehalose, isotrehalose, kojibiose, sophorose, nigerose, laminaribiose, hydrolyzed dextrin, hydrolyzed dextran, and combinations of any two or more thereof. In some embodiments of any aspect of the present technology, the disaccharide may be sucrose. In some, the disaccharide may be lactose. In some, the disaccharide may be maltose. In some, the disaccharide may be isomaltose. In some, the disaccharide may be gentiobiose. In some, the disaccharide may be cellobiose. In any aspects or embodiments, one or more polysaccharides in the mixture or solution may be selected from cellulose, hemicellulose, corn stover, and combinations of any two or more thereof. Notably, when polysaccharides are employed in the present methods, simultaneous hydrolysis and glycosylation occurs. That is, the product prebiotic oligosaccharides contain not only glycosidic linkages of the starting polysaccharide, but other glycosidic linkages as well.

In any aspects or embodiments of the present technology, combinations of two, three, four, five, six or more types of monosaccharides, disaccharides, and/or polysaccharides may be used in the mixtures or solutions of the present technology. By way of non-limiting example, the mixture or solution may include two or more types of monosaccharides. Thus, in some embodiments of any aspect of the present technology, the mixture or solution may include glucose and galactose. In another, the mixture or solution may include glucose and fructose. In some embodiments of any aspect of the present technology, the mixture or solution may include glucose, galactose, fructose, mannose, xylose and arabinose. As another non-limiting example, the mixture or solution may include two or more types of disaccharides. In some embodiments of any aspect of the present technology, the disaccharide may be lactose. In some embodiments of any aspect of the present technology, the disaccharide may be sucrose. In some embodiments of any aspect of the present technology, the disaccharide may be maltose. In some embodiments of any aspect of the present technology, the disaccharide may be cellobiose. In some embodiments of any aspect of the present technology, the disaccharide may be trehalose. In some embodiments of any aspect of the present technology, the mixture or solution may include lactose, sucrose, cellobiose, and maltose. As another non-limiting example, the mixture or solution may include one or more types of monosaccharides and one or more types of disaccharides, such as any of those disclosed herein.

Various temperatures may be used in the present methods so long as they are sufficient to form a product that includes predominantly prebiotic oligosaccharides. For example, the reaction of the mixture or solution of monosaccharides, disaccharides, and/or polysaccharides may take place in a temperature range of about 10° C. to about 160° C. However, to avoid overly lengthy reaction times, a temperature of at least about 50° C. may generally be used. Temperatures that are too high increase the amount of side reactions and impurities. Thus, temperatures for use include about 10° C., about 15° C., about 20° C., about 25° C., about 30° C., about 35° C., about 40° C., about 50° C., about 60° C., about 70° C., about 80° C., about 90° C., about 100° C., about 110° C., about 120° C., about 130° C., about 140° C., about 150° C., about 160° C., or a range between and including any two of the foregoing values. For example, the temperature may be about the temperature is about 35° C. to about 120° C., about 40° C. to about 90° C., about 50° C. to about 90° C., about 60° C. to about 80° C., or about 70° C. to about 90° C. In certain embodiments, the temperature may be about 25° C. to about 70° C.

Temperatures for use in methods of the present technology may vary with starting mono- and disaccharides but may be readily established by those of skill in the art based on the disclosure herein. For example, with respect to the methods for preparing glucooligosaccharides from glucose, the temperature may be about 60° C. to about 80° C., e.g., about 70° C. With respect to the methods of preparing galactooligosaccharides from lactose, the temperature may be about 50° C. to about 130° C., e.g., about 70° C. to about 110° C., or about 90° C. With respect to the methods of preparing fructooligosaccharides from sucrose, the temperature may be about 25° C. to about 80° C., e.g., about 40° C. to about 70° C., e.g., about 50° C.

A variety of reaction times are suitable for use in methods of the present technology, and will vary depending on the concentration of the monosaccharide, disaccharides, and/or polysaccharides, the strength and amount of dehydrating acid, the temperature of the mixture or solution, and the like. Examples of suitable time periods for producing products including predominantly prebiotic oligosaccharides include 1, 2, 3, 4, 5, 10, 15, 20, 25, 30, 40, or 50 minutes, 1, 1.5, or 2 hours, or a range between and including any two of the foregoing values. For example, the reaction time may range from 1 minute to 60 minutes, 1 minute to 30 minutes, 2 minutes to 30 minutes, 5 minutes to 20 minutes, and the like.

Reaction times for preparing prebiotic oligosaccharides may be ascertained by those of skill in the art based on disclosure herein. For example, with respect to the methods of preparing glucooligosaccharides from glucose, the mixture may be reacted for less than about 5 minutes or from about 10 to about 30 minutes, e.g., about 20 minutes. With respect to the methods of preparing galactooligosaccharides from lactose, the mixture may be reacted for less than 5 minutes or from about 10 minutes to about 60 minutes, e.g., about 20 minutes. With respect to the methods of preparing fructooligosaccharides from sucrose, the mixture may be reacted for about 5 to about 20 minutes, e.g., about 10 minutes. With respect to the methods of preparing xylooligosaccharides from xylose, the mixture may be reacted for about 10 to about 50 minutes, e.g., about 30 minutes.

The present methods may be used to efficiently produce many types of prebiotic oligosaccharides. In some embodiments of any aspect of the present methods, the prebiotic oligosaccharides produced contain one or more glycosidic bonds selected from the group consisting of ($\alpha$, $\alpha$)-1,1; ($\alpha$, $\beta$)-1,1; ($\beta$, $\beta$)-1,1; $\alpha$/$\beta$-1,2; $\alpha$/$\beta$-1,3; $\alpha$/$\beta$-1,4; and $\alpha$/$\beta$-1,6. In some embodiments of any aspect of the present technology, the product predominantly including prebiotic oligosaccharides has a DP of at least 2, e.g., 2 to 10. In some embodiments of any aspect of the present technology, the product predominantly including prebiotic oligosaccharides has a DP of at least 3, e.g., 3 to 10. In some embodiments of any aspect of the present technology, the product predominantly including prebiotic oligosaccharides has a DP of 2, 3, 4, 5, 6, 7, 8, 9 or 10, or a range between and including any two of these values.

In some embodiments of any aspect of the present technology, the mixture is reacted at a temperature of 50° C. to 80° C. and the resulting product includes predominantly prebiotic oligosaccharides having a DP of at least 2 or at least 3 or at least 4, e.g., 2-10. In some embodiments of any aspect of the present technology, the mixture is reacted at a temperature of 50° C. to 80° C. and the resulting product includes predominantly prebiotic oligosaccharides having a DP of at least 3 or at least 4, e.g., 3-10. In some embodiments, the mixture is reacted at a temperature of 50° C. to 70° C. and the predominantly prebiotic oligosaccharides have a degree of polymerization of 2 to 10. In some embodiments, the mixture is reacted at a temperature of 50° C. to 70° C. and the predominantly prebiotic oligosaccharides have a degree of polymerization of 2 or about 2. In some embodiments, the mixture is reacted at a temperature of 50° C. to 70° C. and the predominantly prebiotic oligosaccharides have a degree of polymerization of 3 or about 3. In some embodiments, the mixture is reacted at a temperature of 60° C. to 100° C. and the resulting product includes predominantly prebiotic oligosaccharides having a DP of at least 4, e.g., 4 to 10 or 4 to 7. In some embodiments, the mixture is reacted at a temperature of 90° C. and the predominantly prebiotic oligosaccharides have a degree of polymerization of 4 to 8. In some embodiments, the mixture is reacted at a temperature of 90° C. and the predominantly prebiotic oligosaccharides have a degree of polymerization of 2 to 7. In some embodiments, the mixture is reacted at a temperature of 90° C. and the predominantly prebiotic oligosaccharides have a degree of polymerization of 4 to 7. In some embodiments, the mixture is reacted at a temperature of 50° C. and the predominantly prebiotic oligosaccharides have a degree of polymerization of 4 to 7. In some embodiments, the mixture is reacted at a temperature of 50° C. for 10 to 15 minutes and the predominantly prebiotic oligosaccharides have a degree of polymerization of 4 to 7.

In some embodiments of any aspect of the present technology, the method may further include purifying the prebiotic oligosaccharides from the reaction mixture or solution. Any suitable purification methods may be used including but not limited to preparative HPLC, preparative thin-layer chromatography, nanofiltration, adsorption chromatography on charcoal, ion-exchange chromatography, or low-pressure gel permeation chromatography, yeast fermentation (microbes that utilize residual glucose).

The present methods provide prebiotic oligosaccharides with reduced levels of impurities such as, but not limited to, levoglucosan, formic acid (FA), levulinic acid (LA), furfural and hydroxymethyl furfural (HMF). For example, the prebiotic oligosaccharides may have less than 10%, less than 7%, less than 5%, less than 3%, less than 2%, less than 1%, less than 0.5%, or less than 0.1% impurities. In some embodiments of methods of the present technology, the purified prebiotic oligosaccharides contain less than 5%, less than 3%, less than 2%, less than 1%, less than 0.5%, or less than 0.1% impurities, including levoglucosan, formic acid (FA), levulinic acid (LA), furfural and hydroxymethyl furfural (HMF).

In another aspect, the present technology provides compositions comprising one or more prebiotic oligosaccharides prepared according to any of the methods described herein. For example, in some embodiments, the compositions are nutraceutical compositions and comprise food, drink or other edible component such as herbs, spices, flavorings, or a probiotic-containing edible (e.g., yogurt). In some embodiments, the compositions include one or more prebiotic oligosaccharides prepared according to any of the methods described herein and a pharmaceutical active ingredient and/or a pharmaceutically acceptable excipient.

The examples herein are provided to illustrate advantages of the present technology and to further assist a person of ordinary skill in the art with using the present technology. The examples should in no way be construed as limiting the scope of the present technology, as defined by the appended claims. The examples can include or incorporate any of the variations, aspects or aspects of the present technology as described herein. The variations, aspects or aspects described herein may also further include or incorporate variations of any or all other variations, aspects or aspects of the present technology.

EXAMPLES

Materials

D-glucose (99%), D-fructose (99%), D-lactose, D-xylose (99%), D-cellobiose (98%), D-gentiobiose (98%), 5-hydroxymethylfurfural (HMF, 98%), phosphoric acid (85 wt %) were purchased from Alfa Aesar (Tewksbury, Mass.). D-galactose (99%), sulfuric acid (96%), calcium carbonate (99%) were purchased from Acros Organics (Pittsburgh, Pa.). Levoglucosan (99%) and isomaltose (IM, 97%) were purchased from TCI America (Portland, Oreg.). All chemicals were used as received without further purification.

General Procedure A: Sugar Glycosylation to Give Oligosaccharides

The oligosaccharides synthesized in this example include glucooligosaccharides (GlOS), fructooligosaccharides (FOS), galactooligosaccharides (GaOS), xylooligosaccharides (XOS) etc. GlOS/XOS/MOS was synthesized from glucose/xylose/mannose glycosylation in concentrated sulfuric acid ($H_2SO_4$). FOS was synthesized from sucrose or a mixture of glucose and fructose. GaOS was synthesized from lactose or a mixture of glucose and galactose. The general procedure is illustrated using glucose.

Glucose was mixed with $H_2SO_4$ (64-92 wt %) in a 40-mL glass reactor using a Teflon-coated magnetic bar, and the mixture was heated in an oil bath to the reaction temperature (25-90° C.) within 2 min and maintained at the temperature for the rest of the reaction. Then the reaction mixture was quenched by immersing the glass reactor in ice water. The initial glucose content (%, w/w) was calculated as:

$$\text{Initial glucose}\,(\%,\,w/w) = \frac{\text{Glucose}\,(\text{g})}{\text{Glucose}\,(\text{g}) + \text{H}_2\text{SO}_4(\text{g})} \times 100\%$$

When FOS was synthesized from a mixture of glucose and fructose, initial sugar content (%, w/w) and glucose mass ratio (%, w/w) was calculated as:

$$\text{Initial sugar}\,(\%,\,w/w) = \frac{\text{Glucose}\,(\text{g}) + \text{Fructose}\,(\text{g})}{\text{Glucose}\,(\text{g}) + \text{Fructose}\,(g) + \text{H}_2\text{SO}_4(\text{g})} \times 100\%$$

-continued $$\text{Glucose ratio}\,(\%,\,w/w) = \frac{\text{Glucose}\,(\text{g})}{\text{Glucose}\,(\text{g}) + \text{Fructose}\,(\text{g})} \times 100\%$$

Similarly, when GaOS was synthesized from a mixture of glucose and galactose, initial sugar content (%, w/w) and glucose ratio ((%, w/w) was calculated as:

$$\text{Initial sugar}\,(\%,\,w/w) = \frac{\text{Glucose}\,(\text{g}) + \text{Galactose}\,(\text{g})}{\text{Glucose}\,(\text{g}) + \text{Galactose}\,(\text{g}) + \text{H}_2\text{SO}_4(\text{g})} \times 100\%$$

$$\text{Glucose ratio}\,(\%,\,w/w) = \frac{\text{Glucose}\,(\text{g})}{\text{Glucose}\,(\text{g}) + \text{Galactose}\,(\text{g})} \times 100\%$$

General Procedure B: Purification of Product Oligosaccharides

The oligosaccharides from the glycosylation reaction were separated from residual concentrated $H_2SO_4$ by neutralization and filtration. In brief, after glycosylation, the syrup-like mixture was diluted with deionized water and neutralized with calcium carbonate. The soluble oligosaccharides were separated from insoluble calcium sulfate by vacuum filtration. The filtrate containing oligosaccharides was collected and then freeze-dried to constant weight.

General Procedure C: Chromatographic Quantitation of Saccharides

The concentration of monosaccharides (e.g., glucose, galactose, fructose, xylose, levoglucosan) and disaccharides (e.g., sucrose, lactose, isomaltose, gentiobiose) were quantitated using a high-performance ion exchange chromatography (HPIC) system (Dionex ICS-3000, Sunnyvale, Calif.) equipped with an integrated amperometric detector and CarboPac® PA1 guard and analytical columns (Thermo Scientific, Sunnyvale, Calif.). The gradient eluent containing A: deionized water (18 MΩ) and B: 0.1 M NaOH was programmed as 0-40 min, 100% A and 0% B; 40-49 min, 30% A and 70% B; 49-58 min, 20% A and 80% B with a flow rate of 0.7 mL/min. An isocratic post-column eluent of 0.5 M NaOH (flow rate 0.15 mL/min) was used to ensure the baseline stability and to enhance the detector sensitivity.

General Procedure D: Quantitation of Sugar Degradation Products

The monosaccharide degradation products formic acid (FA), levulinic acid (LA), 5-hydroxylmethylfurfural (HMF) and furfural were quantitated using a high-performance liquid chromatography (HPLC) system (Dionex ICS-3000, Sunnyvale, Calif.) equipped with a Supelco® C-610H column (Bellefonte, Pa.) and a variable wavelength detector (VWD) at 210 nm. The mobile phase is isocratic 0.1% phosphoric acid with a flow rate of 0.6 mL/min.

General Procedure E: Quantitation of Oligosaccharides

Quantitation of oligosaccharides was conducted following post-hydrolysis that convert all the oligosaccharides to monosaccharides (GlOS to glucose, FOS to glucose and fructose, GaOS to glucose and galactose, and XOS to xylose, respectively). Briefly, after the glycosylation the syrup-like mixture was diluted with 4% sulfuric acid to a total sugar concentration less than 5.0 g/L and hydrolyzed at 121° C. for 1 h in an autoclave to convert all oligosaccharides to monosaccharides.

After neutralization with calcium carbonate, the monosaccharides in the hydrolysate was quantitated with the HPIC method described above.

i. Quantitation of GlOS

For glucose glycosylation to GlOS, the GlOS yield and selectivity was calculated by following Equation 1 and 2. The yield of residual glucose after glycosylation was calculated using Equation 3.

$$GlOS \text{ yield (mol \%)} = \frac{Glu^P - Glu^G - LGA^G}{Glu^I} \quad (1)$$

$$GlOS \text{ selectivity (mol \%)} = \frac{Glu^P - Glu^G - LGA^G}{Glu^I - Glu^G} \quad (2)$$

$$\text{Residual glucose yield (mol \%)} = \frac{Glu^G}{Glu^I} \quad (3)$$

where $Glu^I$ denoted the initial glucose (mol) before glycosylation, $Glu^G$ denoted the residual glucose (mol) after glycosylation and $Glu^P$ denoted total glucose (mol) after post hydrolysis. $LGA^G$ denoted the intramolecular dehydration side-product levoglucosan (mol) after glycosylation.

The yield of isomaltose (IM) and gentiobiose (GB) was calculated by following Equation 4 and 5. $IM^G$ and $GB^G$ denoted the IM (mol) and GB (mol) after glycosylation.

$$IM \text{ yield (mol \%)} = \frac{IM^G}{Glu^I} \quad (4)$$

$$GB \text{ yield (mol \%)} = \frac{GB^G}{Glu^I} \quad (5)$$

ii. Quantitation of GaOS

For lactose glycosylation to GaOS, the GaOS yield and selectivity was calculated by following Equation 6 and 7. The yield of residual lactose after glycosylation was calculated using Equation 8. The yield of residual glucose and galactose that derived from lactose hydrolysis was calculated using Equation 9.

$$GaOS \text{ yield (mol \%)} =$$
$$\frac{(Glu + Gal)^P - (Glu + Gal)^G - LGA^G - 2 \times Lac^G}{2 \times Lac^I} \quad (6)$$

$$GaOS \text{ selectivity (mol \%)} =$$
$$\frac{(Glu + Gal)^P - (Glu + Gal)^G - LGA^G - 2 \times Lac^G}{2 \times (Lac^I - Lac^G)} \quad (7)$$

$$\text{Residual lactose yield (mol \%)} = \frac{Lac^G}{Lac^I} \quad (8)$$

$$\text{Residual glucose and galactose yield (mol \%)} = \frac{(Glu + Gal)^G}{2 \times Lac^I} \quad (9)$$

$(Glu+Gal)^P$ and $(Glu+Gal)^G$ denoted the total glucose and galactose concentration (mol) after post hydrolysis and after glycosylation, respectively. $Lac^I$ and $Lac^G$ denoted the initial lactose (mol) and residual lactose (mol) after glycosylation, respectively.

iii. Quantitation of FOS

For sucrose glycosylation to FOS, the molar yield and molar selectivity of FOS was calculated using following Equation 10 and 11. The molar yield of residual sucrose was calculated using Equation 12. The yield of residual glucose and fructose that derived from sucrose hydrolysis was calculated using Equation 13.

$$FOS \text{ yield (mol \%)} = \quad (10)$$
$$\frac{\begin{array}{c}(Glu + Fru)^P - (Glu + Fru)^G + (FA + LA + HMF)^P - \\ (FA + LA + HMF)^G - LGA^G - 2 \times Suc^G\end{array}}{2 \times Suc^I}$$

$$FOS \text{ selectivity (mol \%)} = \quad (11)$$
$$\frac{\begin{array}{c}(Glu + Fru)^P - (Glu + Fru)^G + (FA + LA + HMF)^P - \\ (FA + LA + HMF)^G - LGA^G - 2 \times Suc^G\end{array}}{2 \times (Suc^I - Suc^G)}$$

$$\text{Residual sucrose yield (mol \%)} = \frac{Suc^G}{Suc^I} \quad (12)$$

$$\text{Residual glucose and fructose yield (mol \%)} = \frac{(Glu + Fru)^G}{2 \times Suc^I} \quad (13)$$

$(Glu+Fru)^P$ and $(Glu+Fru)^G$ denoted the total glucose (mol) and fructose (mol) after post hydrolysis and glycosylation, respectively. $Suc^I$ and $Suc^G$ denoted the initial sucrose (mol) and residual lactose (mol) after glycosylation. $(FA+LA+HMF)^P$ and $(FA+LA+HMF)^G$ denoted the total formic acid, levulinic acid and 5-hydroxymethylfurfural concentration (mol) after post hydrolysis and after glycosylation, respectively.

iv. Quantitation of XOS

For xylose glycosylation to XOS, the molar yield and molar selectivity of XOS was calculated using following Equation 14 and 15. The molar yield of residual xylose was calculated using Equation 16.

$$XOS \text{ yield (mol \%)} = \frac{Xyl^P - Xyl^G}{Xyl^I} \quad (14)$$

$$XOS \text{ selectivity (mol \%)} = \frac{Xyl^P - Xyl^G}{Xyl^I - Xyl^G} \quad (15)$$

$$\text{Residual xylose yield (mol \%)} = \frac{Xyl^G}{Xyl^I} \quad (16)$$

where $Xyl^I$ denoted the initial xylose (mol) before glycosylation, $Xyl^G$ denoted the residual xylose (mol) after glycosylation and $Xyl^P$ denoted total xylose (mol) after post hydrolysis.

General Procedure F: GPC Analysis

The degree of polymerization (DP) of the synthesized oligosaccharides was estimated by gel permeation chromatography (GPC) after derivatizing the hydroxyl groups to form the oligosaccharide tricarbanilates. Briefly, dried oligosaccharides (25 mg) were mixed with phenyl isocyanate (0.5 mL) and anhydrous pyridine (5 mL) in a 20-mL glass vial with a PTFE-coated septum. The reaction mixture was kept at 80° C. with gentle stirring until oligosaccharides were completely dissolved (usually 48-72 h). Then, methanol (0.5 mL) was added to the reaction mixture to remove excess phenyl isocyanate, and the oligosaccharides tricarbanilates were recovered by precipitating in water-methanol (3:7, 50 mL), centrifugation, and washed repeatedly with aqueous methanol, followed by water, and then freeze dried. The oligosaccharides tricarbanilates was dissolved in THF (10 mg/mL) and then analyzed by GPC (1.0 mL/min THF as eluent). The weight average degree of polymerization of the oligosaccharides was calculated as:

$$DP = M_w/519 \tag{1}$$

where 519 g/mol is the molecular weight of the repeating unit of the derivatized oligosaccharides.

General Procedure G: NMR

The glycosyl linkage patterns of the synthesized oligosaccharides were determined by NMR spectroscopy. Prior to NMR measurement, the purified oligosaccharides were dissolved in D2O (99.9 atom %, Sigma) and lyophilized to remove exchangeable hydroxyl protons. This process was repeated three times and the samples (15-20 mg) were finally dissolved in 600 $D_2O$ (99.97 atom %, with 1% DSS as a reference) in the NMR tube. NMR spectroscopy ($^1H$, $^1H$-$^{13}C$ HSQC) was recorded on a Bruker AVANCE III 500 MHz instrument with DCH cryoprobe at 30° C. (Department of Chemistry, UW-Madison). $^1H$-$^{13}C$ HSQC were measured in the $^1H$-detected mode with proton decoupling in the $^{13}C$ domain. The parameters were as follows: 2 k×1 k data points; zero-filled to 4 k data points; 32 scans per t1 value; spectral width in t1 20 kHz and in t2 5 kHz; relaxation delay 1 s. All NMR data were processed using Topspin 4.0.8 (Bruker). To estimate the proportion of glycosyl linkages in the oligosaccharides, the anomeric contours of $\alpha/\beta$-1,1, $\alpha/\beta$-1,2, $\alpha/\beta$-1,3, $\alpha/\beta$-1,4, and $\alpha/\beta$-1,6 were integrated for relative comparison due to the similar chemical environment and distinguishable chemical shifts.

General Procedure H: Nanofiltration

Dead-end nanofiltration was carried out with Advantec® UHP76 stirred cell (AdvantecMFS, Inc, CA, USA) using compressed nitrogen. Flat sheet membrane Trisep®XN45 (Microdyn-Nadir, CA, USA) with a molecular weight cutoff (MWCO) of 300-500 Daltons was cut to fit the filtration area (0.00385 m²) of the stirred cell.

The operation temperature of the stirred cell was 20° C. A Teflon stir bar (mounted in the stirred cell) was employed at a stirring rate of 150 rpm. After a steady state condition was achieved, permeate batch samples was collected and analyzed by HPEAC to determine the sugar concentration.

The volumetric flux of permeate was measured and expressed as liter per square meter per hour ($\cdot Lm^{-2} \cdot h^{-1}$):

$$J_V = \frac{V_P}{A \times t} \tag{1}$$

where $V_P$ is the permeate volume (L), A is the effective filtration area (0.00385 m²), t is time (h).

Volume concentration ratio (VCR) was calculated according to the following equation:

$$VCR = \frac{V_f}{V_r} \tag{2}$$

where $V_f$ and $V_r$ is the volume of the initial feed and the volume of the retentate, respectively.

The rejection coefficient $R_i$ for a certain solute i in the batch nanofiltration process was calculated by:

$$R_i = \left(1 - \frac{C_p}{C_f}\right) \times 100\% \tag{3}$$

where $C_p$ and $C_f$ is the concentration (g/mL) of the solute i in the permeate and the initial feed solution, respectively.

Figure 1B:
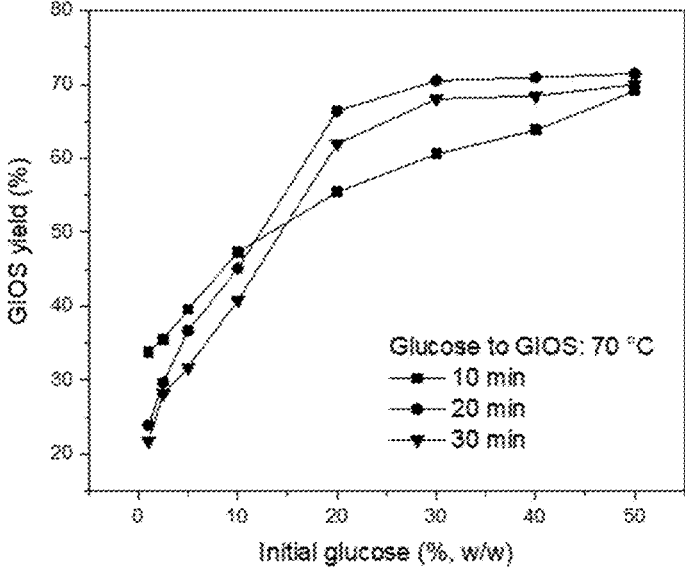
Figure 1C:
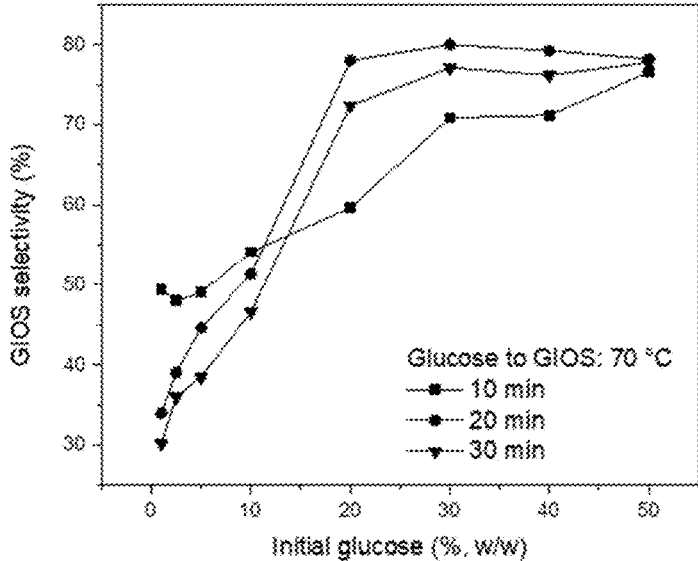

Example 1: Glucose Glycosylation to GlOS in Concentrated $H_2SO_4$ i. Effect of Initial Glucose Concentration The effect of initial glucose content on glucose glycosylation to GlOS in concentrated $H_2SO_4$ (72 wt %) at 70° C. was summarized in FIG. 1. As shown in FIG. 1A, when initial glucose was below 10 wt %, the residual glucose yield decreased dramatically as initial glucose increased, which indicated that high glucose concentration favored its conversion. Over 85 mol % glucose was converted after glycosylation reaction when the initial glucose increased to 50 wt %. It can be seen from FIGS. 1B and 1C that GlOS yield and selectivity both increased with initial glucose and the GlOS yield ascend to a maximum of 71.4% with a selectivity of 78.2% as initial glucose increased to 50 wt % after 20 min glycosylation. When initial glucose was larger than 20 wt %, 20 min was the optimum reaction time since GlOS yield and selectivity slightly decreased when reaction time was extended to 30 min.

Figure 1D:
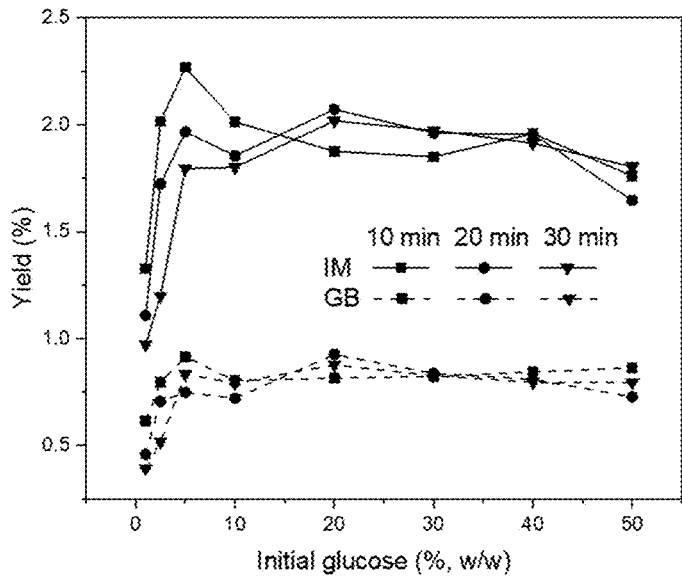
Figure 1E:
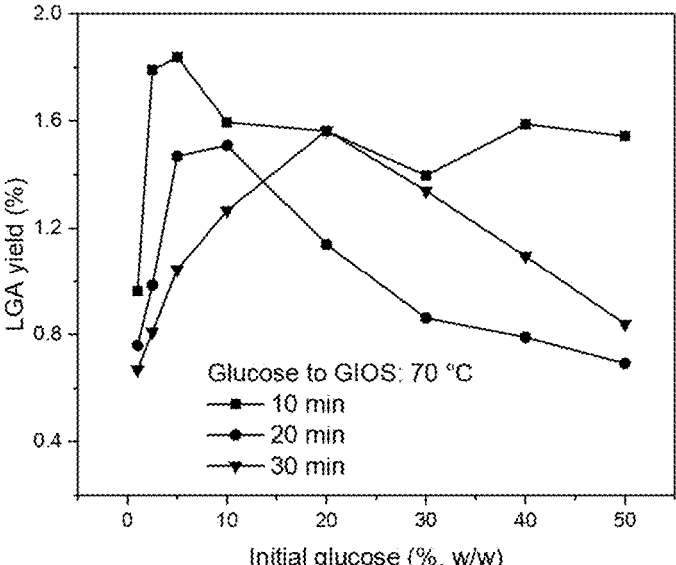
Figure 1F:
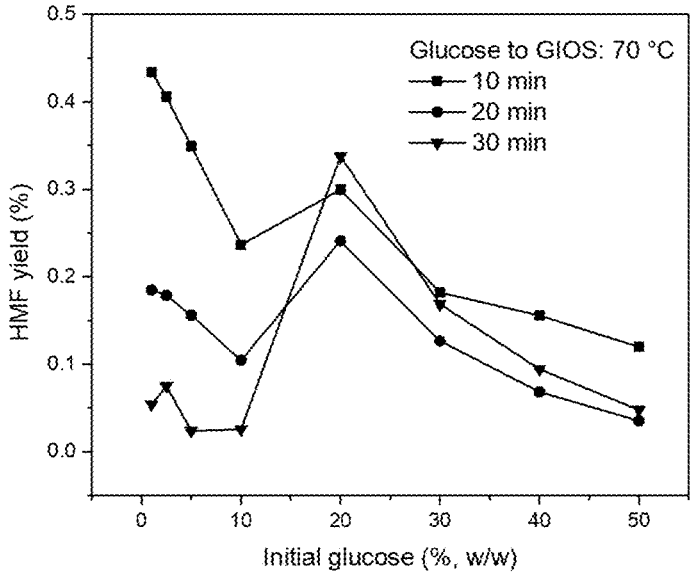

Isomaltose (IM, $\alpha$-1,6 linked disaccharide of glucose) and gentiobiose (GB, a $\beta$-1,6 linked disaccharide of glucose) were the most abundant disaccharides in the GlOS. The yield of IM and GB slightly increased then remained almost unchanged as initial glucose increased (FIG. 1D). When initial glucose was 5 wt %, the IM and GB yield reached highest (2.27% and 0.91%, respectively) after 10 min glycosylation at 70° C. Other than glucose glycosylation, glucose could undergo reversible intramolecular dehydration to form levoglucosan (LGA, 1,6-anhydro-$\beta$-D-glucose). The yield of LGA increased with reaction time obviously, and slightly increased with initial glucose (FIG. 1E). The maximum LGA yield was 0.12% at 70° C., 30 min. The irreversible glucose dehydration to 5-hydroxymethylfufural (HMF) is a main side reaction for glucose glycosylation. The HMF yield slightly decreased from 0.33% to 0.04% when initial glucose increased from 20 wt % to 50% w/w at 70° C., 30 min (FIG. 1D).

ii. Effect of $H_2SO_4$ Concentration

The effect of sulfuric acid concentration ($H_2SO_4$) on glucose glycosylation to GlOS is shown in FIG. 2. From FIG. 2A, over 90 mol % glucose was consumed within 10 min when $H_2SO_4$ concentration was larger than 76 wt %. Apparently, the residual glucose yield decreased as $H_2SO_4$ concentration increased from 60 wt % to 84 wt %, which suggested that higher $H_2SO_4$ concentration favored the glucose conversion. But there was a slightly increase in residual glucose when $H_2SO_4$ was larger than 84 wt %, probably because glucose could not be totally dissolved in such concentrated $H_2SO_4$.

Figure 2A:
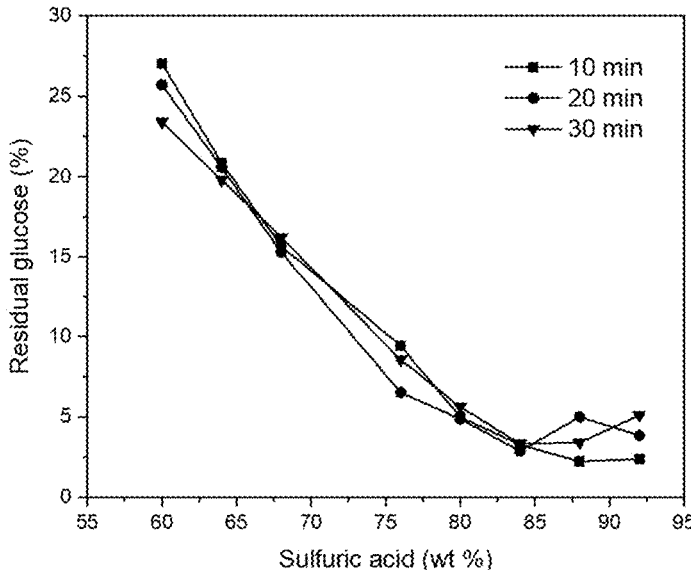
FIGS. 2A-2F show the effect of sulfuric acid concentration (60-92 wt %) on the synthesis of GlOS from glucose glycosylation with 30 wt % initial glucose at 70° C. (2A) residual glucose yield; (2B) GlOS yield; (2C) GlOS selectivity; (2D) IM and GB yield; (2E) LGA yield; (2F) HMF yield.
Figure 2B:
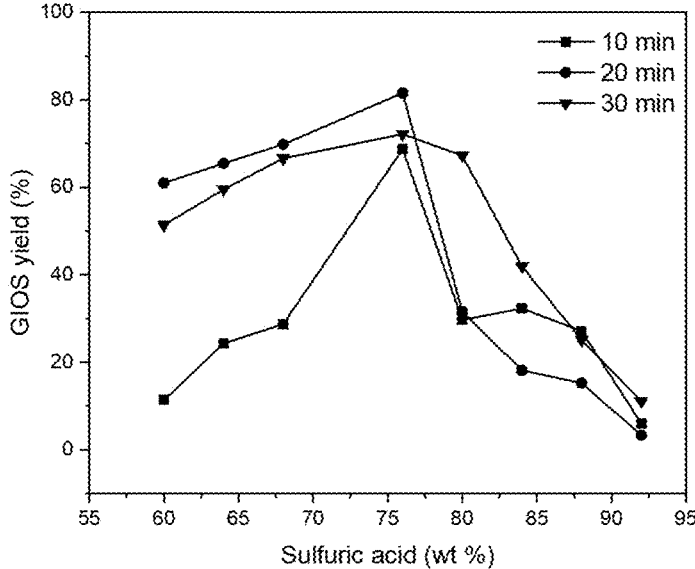
Figure 2C:
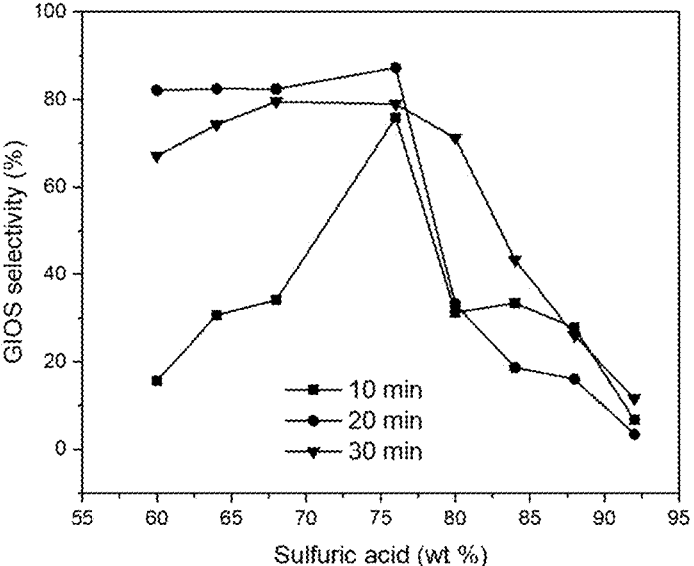
Figure 2D:
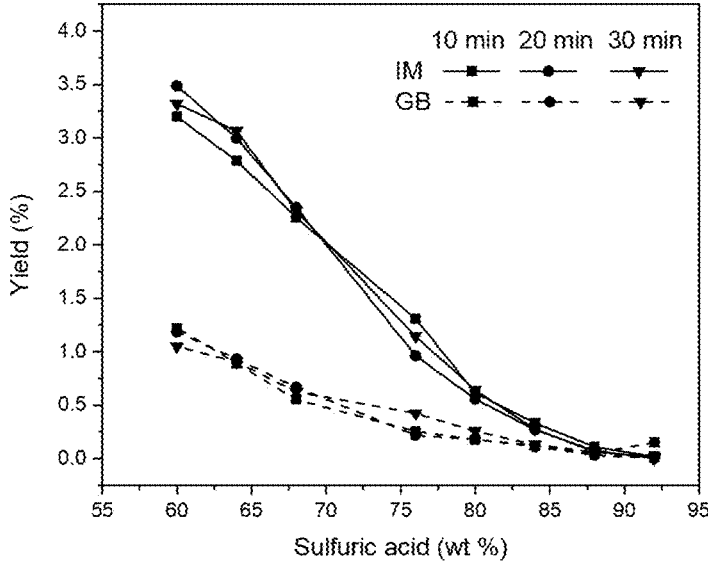
Figure 2E:
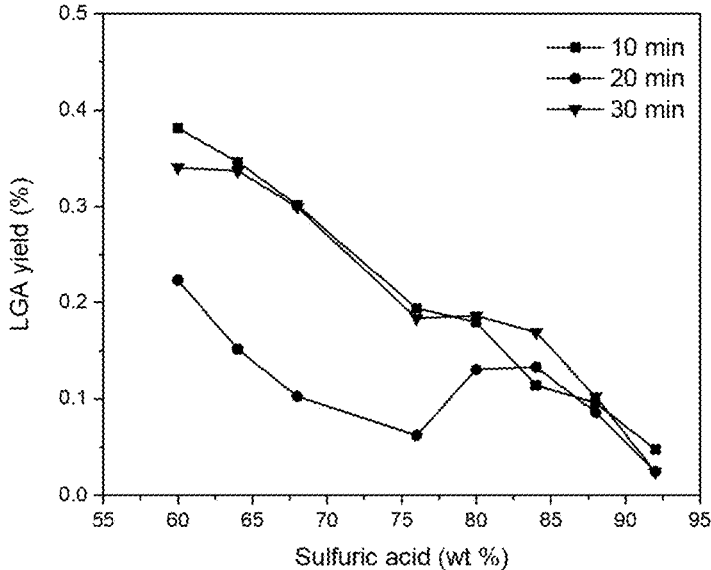
Figure 2F:
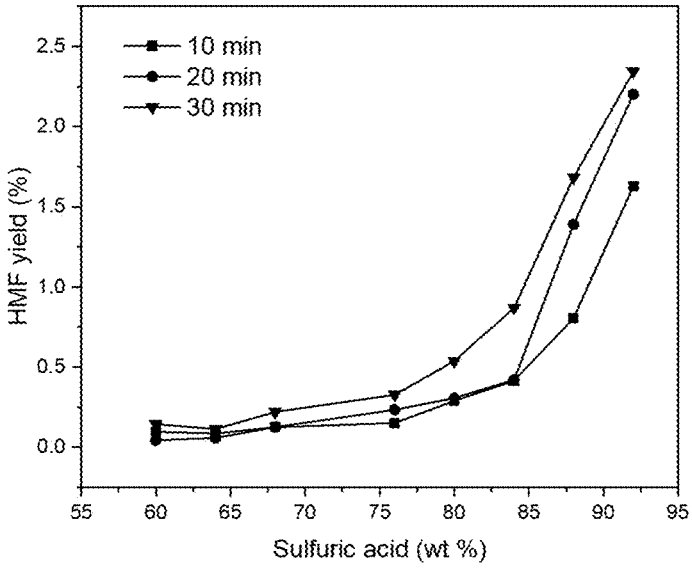
Figure 3A:
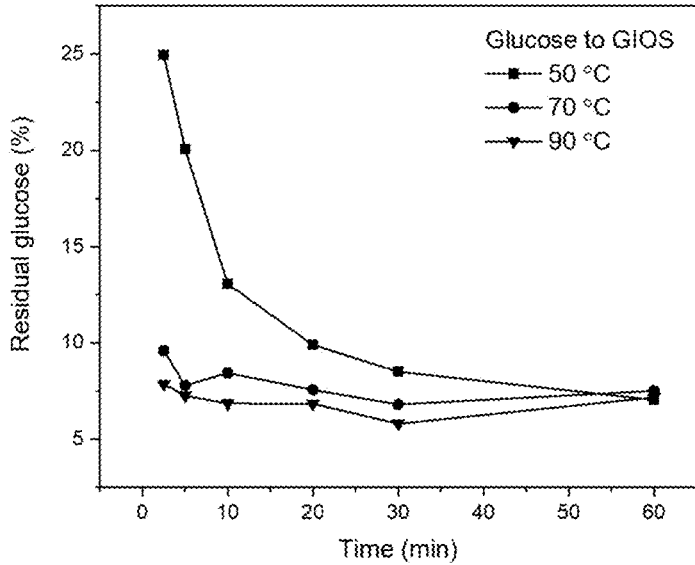
FIGS. 3A-3F show glucose glycosylation to GlOS in $H_2SO_4$ at 50, 70 and 90° C. for 2.5-60 min. (3A) residual glucose yield; (3B) GlOS yield; (3C) GlOS selectivity; (3D) IM and GB yield; (3E) LGA yield; (3F) HMF yield. (50 wt % initial glucose and 76 wt % $H_2SO_4$).
Figure 3B:
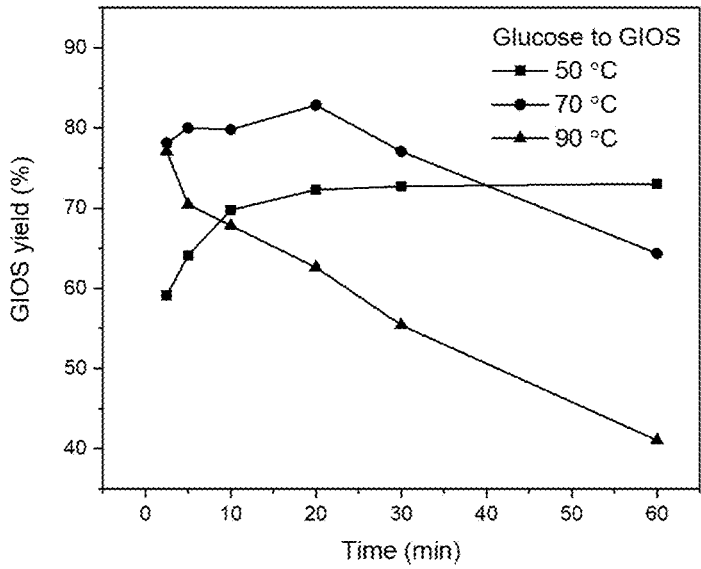
Figure 3C:
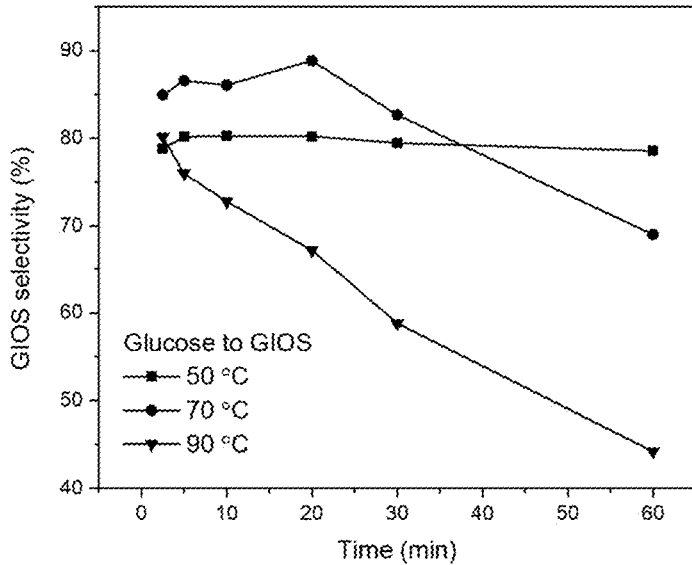
Figure 3D:
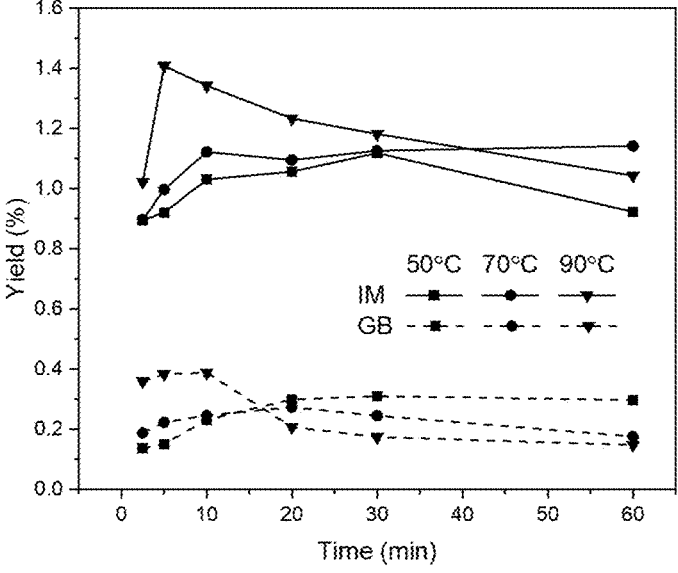
Figure 3E:
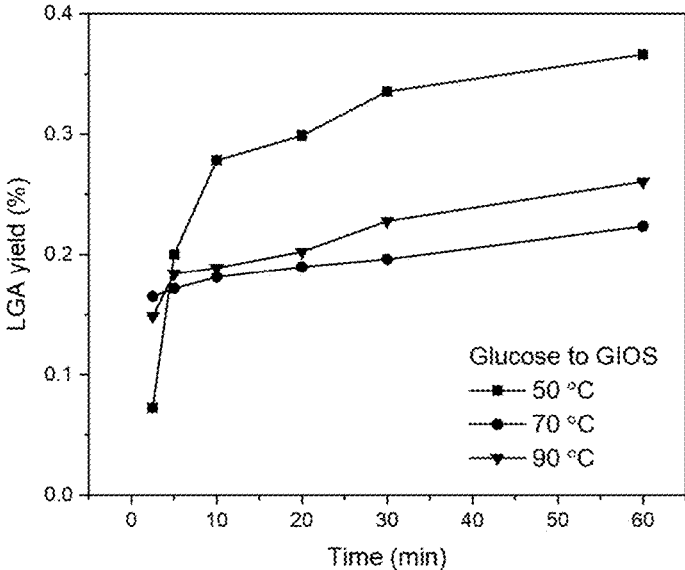
Figure 3F:
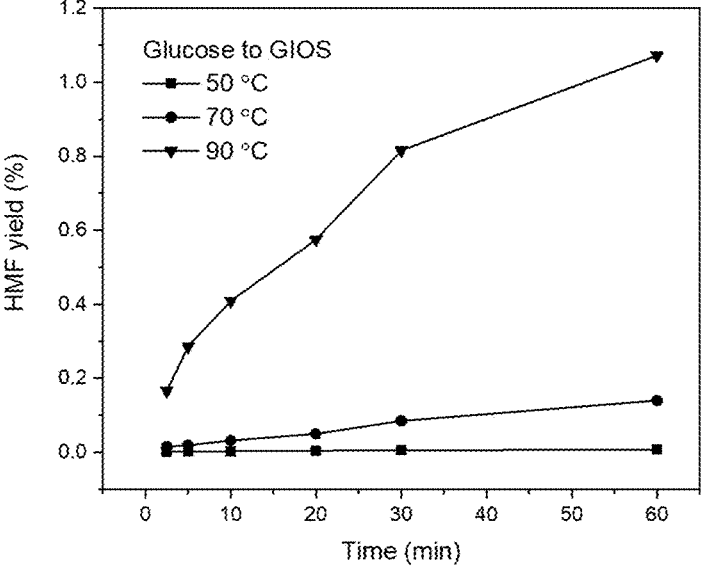

As shown in FIGS. 2B and 2C, the optimum GlOS yield (81.6%, with a selectivity of 87.3%) was achieved at 76 wt % $H_2SO_4$ at 70° C., 20 min. The GlOS yield and selectivity showed an increase with $H_2SO_4$ concentration when it was lower than 76 wt %. This was mainly because there was less free water in concentrated $H_2SO_4$, which favored the glucose dehydration to GlOS. But there was an obvious decrease in GlOS yield and selectivity when $H_2SO_4$ was larger than 76 wt %, which was mostly because higher $H_2SO_4$ concentration promoted the dehydration of glucose to HMF (FIG. 2F) as the LGA yield slightly decreased with the $H_2SO_4$ concentration. FIG. 2D showed that the yield of IM and GB gradually decreased with $H_2SO_4$ concentration. It was likely that disaccharides IM and GB undergo further glycosylation to form larger GlOS molecules under high $H_2SO_4$ concentration. The highest yield of IM and GB was 3.22% and 1.20%, respectively.

iii. Effect of Reaction Temperature

The results of glucose glycosylation to GlOS at varied temperatures (50, 70 and 90° C.) was shown in FIG. 3. Elevating the reaction temperature from 50 to 90° C. accelerated the glucose glycosylation reaction (FIG. 3A), since the residual glucose decreased from 25.0 to 7.9 mol % after 2.5 min reaction. As the reaction time extended to 60 min, the residual glucose was almost same for all reaction temperatures. At 50° C., the GlOS yield gradually increased with reaction time, reaching the maximum of 73.0% (with 78.6% selectivity) at 60 min (FIG. 3B). When reaction temperature was increased to 70° C., the maximum GlOS yield ascended to 82.9% (with 88.9% selectivity) after 20 min glycosylation. But when temperature was further elevated to 90° C., the GlOS yield decreased with reaction time and maximum yield was 77.1% (with 80.2% selectivity) at 2.5 min. This was mainly because more degradation products (e.g., HMF) was formed at higher reaction temperature and longer reaction time (FIG. 3F). When reaction time was less than 10 min, elevating temperature favored the formation of IM and GB. The maximum yield of IM and GB was obtained at 90° C. 5 min, which was 1.4% and 0.4%, respectively.

iv. Glucose Glycosylation to GlOS in Concentrated $H_3PO_4$

TABLE 1

Glucose glycosylation to GlOS in concentrated phosphoric acid

| | Temperature (° C.) | | | |
| | 70 | | 90 | |
| | $H_3PO_4$ (wt %) | | | |
| | 70 | 80 | 70 | 80 |
| Residual glucose (%) | 80.4 | 70.4 | 37.0 | 19.4 |
| GlOS yield (%) | 17.7 | 44.9 | 2.0 | 20.1 |
| GlOS selectivity (%) | 7.8 | 24.6 | 3.2 | 25.0 |
| IM (%) | 1.0 | 1.7 | 2.7 | 1.6 |
| GB (%) | 1.1 | 2.2 | 2.4 | 1.2 |
| LGA (%) | 0.22 | 0.74 | 0.45 | 0.54 |
| HMF (%) | 0.0101 | 0.0109 | 0.0724 | 0.0737 |

Initial glucose 50 wt %, time 30 min

The glucose glycosylation to GlOS in concentrated phosphoric acid was summarized in Table 1. It can be seen that over 70 mol % glucose remained unreacted after glycosylation in $H_3PO_4$ at 70° C. for 30 min. Increasing reaction temperature from 70° C. to 90° C. significantly improved the glucose conversion. The optimum GlOS yield was 44.9% for glucose glycosylation in 80 wt % $H_3PO_4$ at 70° C. for 30 min, which was obviously lower than that in $H_2SO_4$ at identical condition (GlOS yield 67.2%). The highest IM and GB yield was obtained at 70 wt % $H_3PO_4$ at 90° C., which was 2.7% and 2.4% respectively. The HMF yield was relatively low (all below 0.1%) for all reaction in $H_3PO_4$. It can be concluded that $H_3PO_4$ is an effective solvent for glucose glycosylation to GlOS, but its dehydration ability is not as good as $H_2SO_4$. So, higher $H_3PO_4$ concentration and longer reaction time may be required to achieve a satisfactory GlOS yield.

Example 2: Lactose Glycosylation to GaOS in Concentrated $H_2SO_4$ i. Effect of Initial Lactose Concentration

Figure 4A:
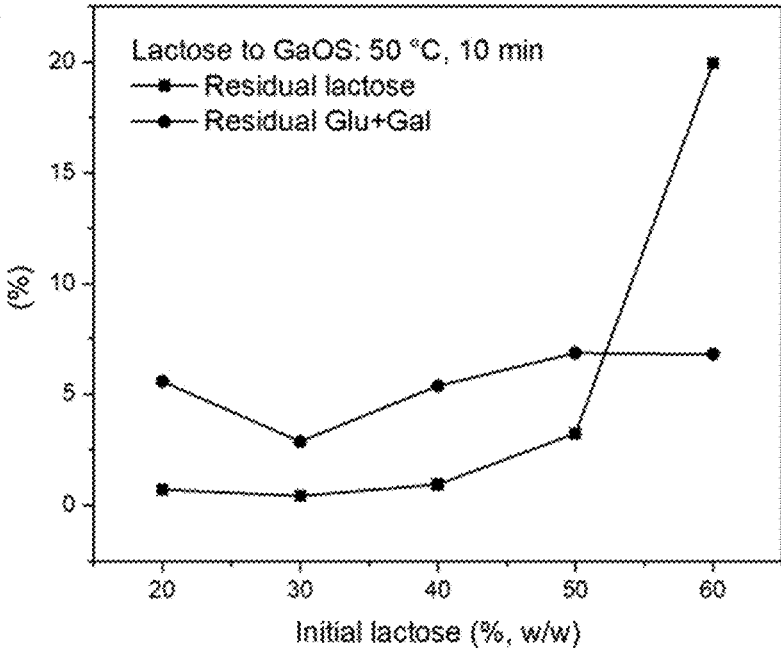
FIGS. 4A-4C show the effect of initial lactose (20-60%, w/w) on GaOS synthesis from lactose glycosylation in 76 wt % wt $H_2SO_4$ at 50° C. for 10 min. (4A) residual lactose yield and residual glucose and galactose yield; (4B) GaOS yield and selectivity; (4C) yields of side products formic acid (FA), levulinic acid (LA), hydroxymethylfurfural (HMF) and levoglucosan (LGA).
Figure 4B:
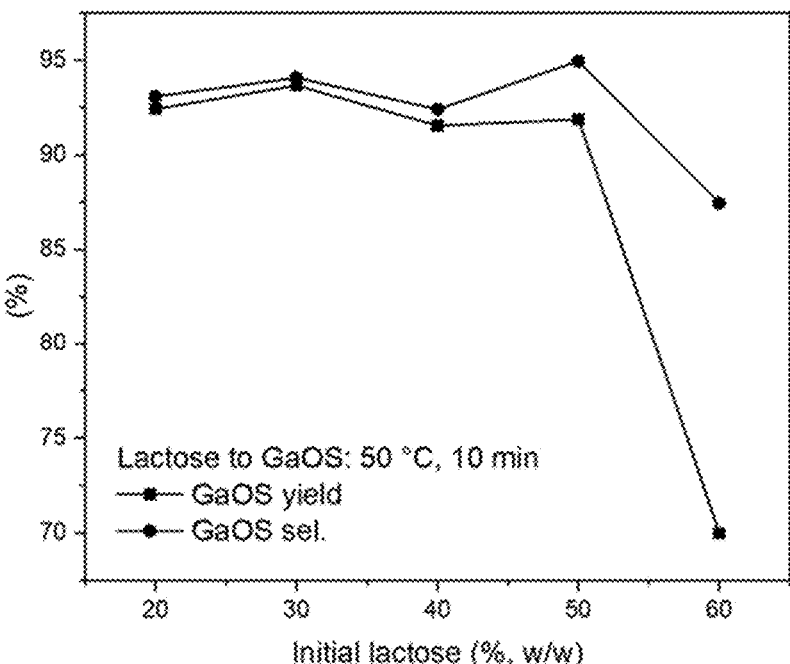
Figure 4C:
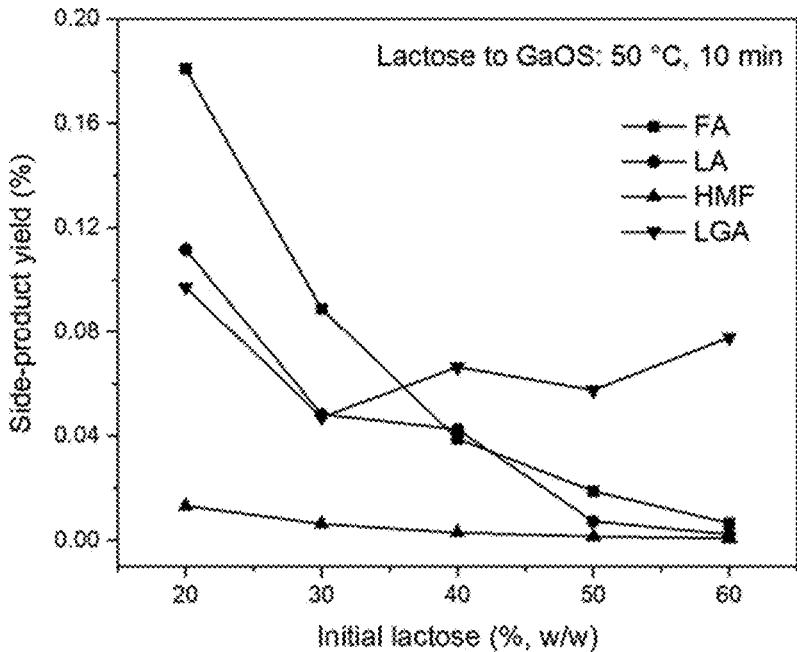

Galactooligosaccharides (GaOS) is the one of the most extensively studied prebiotic oligosaccharides. The effect of initial lactose on lactose glycosylation to GaOS in $H_2SO_4$ was shown in FIG. 4. It can be seen from FIG. 4A that over 95% lactose was consumed in glycosylation when initial lactose was no more than 50%. The yield of residual glucose and galactose that derived from lactose hydrolysis was no more than 10%, which suggested that the majority of sugar substrates was glycosylated to GaOS. FIG. 4B showed that the GaOS yield was as high as 90% when initial lactose was within 20-50%. The maximum GaOS yield (93.7%) was obtained at 30% initial lactose with a selectivity of 94.1%. But when initial lactose increased to 60%, the GaOS yield decreased to 70.0% with 87.5% selectivity. This was mainly because 20.0% lactose remained unreacted at this condition (50° C., 10 min). Elevating the glycosylation temperature is expected to improve the GaOS yield. From FIG. 4C, the yield of degradation products FA, LA and HMF was all below 0.2% and decreased with the initial lactose. The yield of reversible dehydration product LGA didn't change much with initial lactose. This indicated that lactose, glucose, and galactose are relatively stable and not easily dehydrated during lactose glycosylation to GaOS.

ii. Effect of $H_2SO_4$ Concentration

Figure 5A:
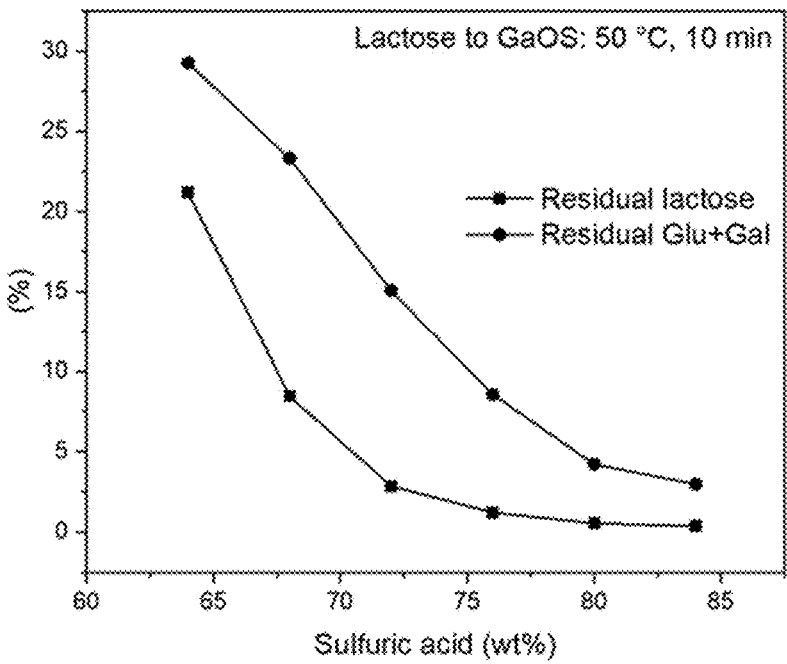
FIGS. 5A-5C show the effect of sulfuric acid concentration (64-84 wt %) on GaOS synthesis from lactose glycosylation in 30 wt % initial lactose at 50° C. for 10 min. (5A) residual lactose yield and residual glucose and galactose yield; (5B) GaOS yield and selectivity; (5C) yields of side products formic acid (FA), levulinic acid (LA), hydroxymethylfurfural (HMF) and levoglucosan (LGA).
Figure 5B:
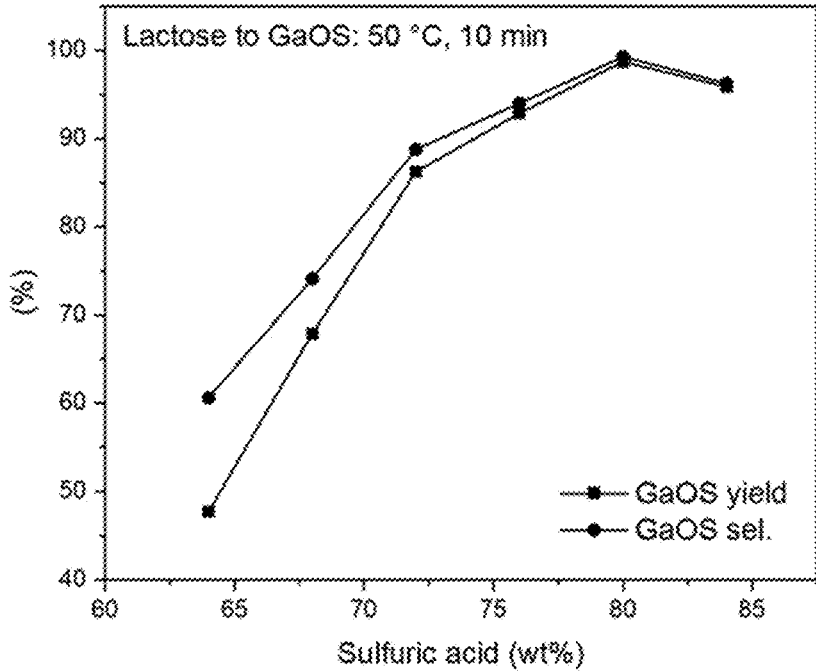
Figure 5C:
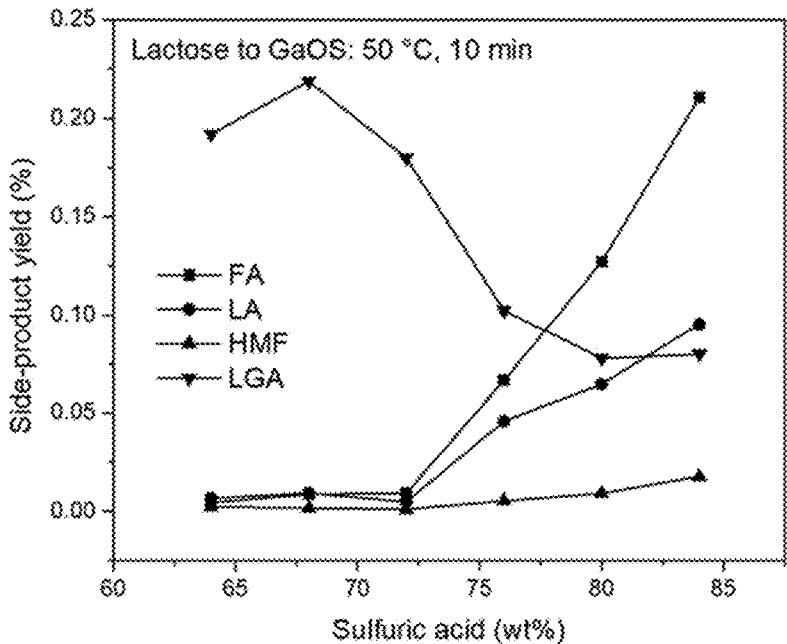

The effect of sulfuric acid concentration on lactose glycosylation to GaOS was summarized in FIG. 5. From FIG. 5A, the residual lactose decreased from 21.2% to 2.8% as $H_2SO_4$ increased from 64 to 72 wt %, and further decreased to 0.4% as $H_2SO_4$ ascended to 84 wt %. The residual glucose and galactose also decreased gradually with $H_2SO_4$ concentration, which suggested that higher $H_2SO_4$ concentration favor sugar conversion during glycosylation. The GaOS yield increased from 47.7% to 92.8% as $H_2SO_4$ concentration increased from 64% to 72% (FIG. 5B). The maximum GaOS yield (98.7%) with 99.3% selectivity was obtained at 80 wt % $H_2SO_4$ and slightly decreased to 95.9% when $H_2SO_4$ was 84%. As shown in FIG. 5C, the side-product yield was below 0.01% when $H_2SO_4$ was below 72 wt %, and then increased obviously with $H_2SO_4$ concentration. The maximum FA, LA and HMF yield was 0.21%, 0.09% and 0.02% respectively, which was still very low.

iii. Effect of Reaction Temperature

The effect of reaction temperature on lactose glycosylation to GaOS in concentrated $H_2SO_4$ was summarized in FIG. 6. As shown in FIG. 6A, over 80 mol % lactose was consumed in 2.5 min at 50° C., and the residual lactose gradually decreased with reaction time, with only 0.9 mol % lactose remained at 60 min. When reaction temperature was elevated to 70° C., over 98 mol % lactose was consumed at 2.5 min, which indicated that heat accelerated the lactose conversion obviously. The yield of residual glucose and galactose was below 0.1% at 2.5 min, and decreased with temperature (FIG. 6B). This indicated that almost all glucose and galactose was consumed in glycosylation reaction. It can be seen from FIGS. 6C and 6D that the GaOS yield and selectivity showed a different pattern at different glycosylation temperature. At 50° C., the GaOS yield gradually increased from 71.9% to 93.5% as reaction time extended from 2.5 to 60 min. At 70° C., the GaOS yield increased to 93.3% at 2.5 min and remained around 90% during 60 min reaction. At 90° C. 2.5 min, the GaOS yield further increased to 96.6% but decreased dramatically with reaction time. This was mainly because degradation side products FA, LA and HMF are favored at higher temperature and longer reaction time, as shown in FIG. 6E, FIG. 6F and FIG. 6G. The reversible degradation product LGA was also favored at higher temperature, but the overall yield was still very low (FIG. 6H). The maximum GaOS yield (95.6%) was obtained at 70° C., 20 min with GaOS selectivity of 96.6%. Therefore, moderate heat accelerated the lactose glycosylation and improved the overall GaOS yield and selectivity.

Figure 7A:
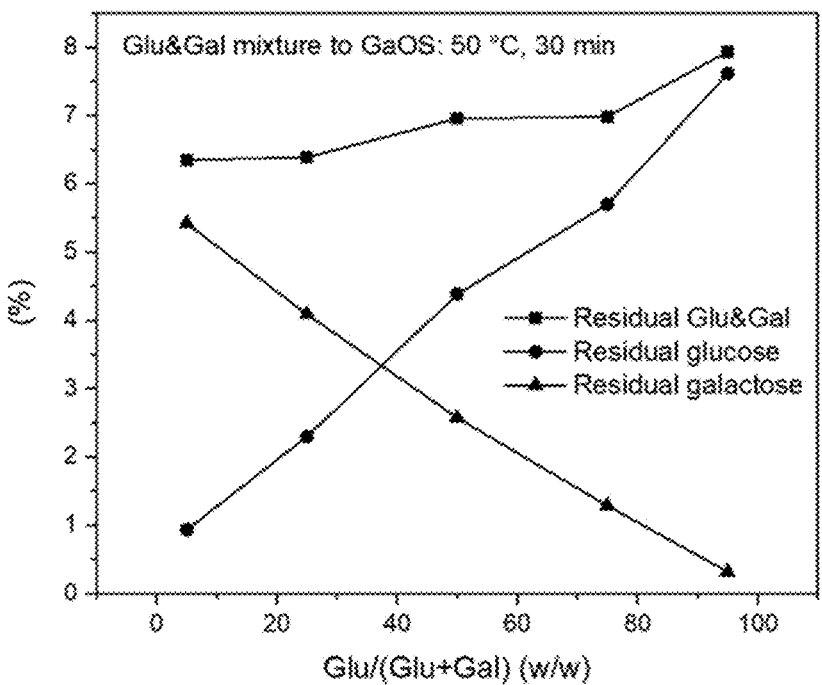
FIGS. 7A-7B show glucose-galactose mixture glycosylation to GaOS at 50° C. for 30 min. The glycosylation was conducted at 50 wt % initial sugar (glucose and galactose) and 76 wt % $H_2SO_4$ (7A) residual glucose and galactose; (7B) GaOS yield and selectivity.
Figure 7B:
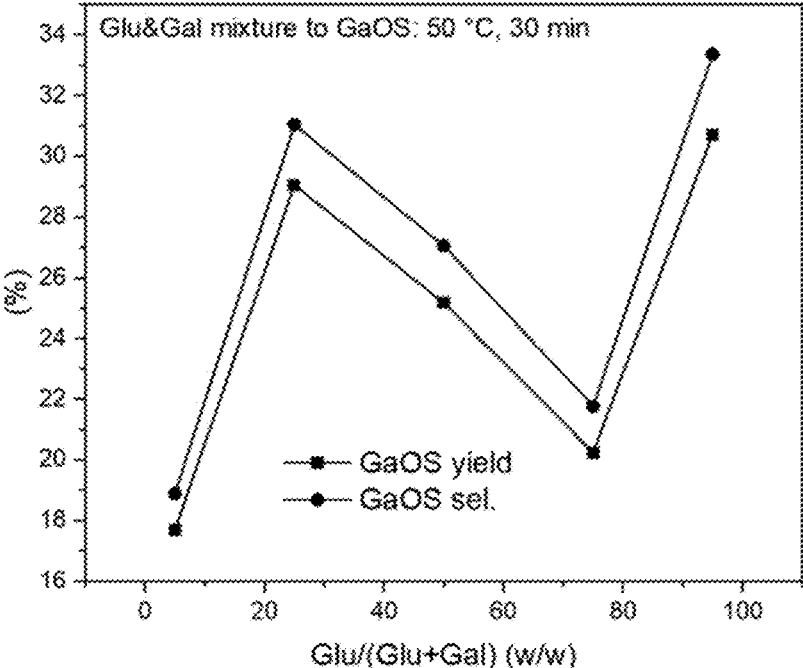

Example 3: GaOS Synthesis from Galactose or Glucose-Galactose Mixture Glycosylation In order to elucidate the reactivity of monosugar (glucose and galactose) towards glycosylation, glucose-galactose mixture (total initial sugar 50 wt %) with different glucose ratio (5-95 wt %, mass of glucose to the mass of glucose and galactose) was used to synthesize GaOS. As shown in FIG. 7A, the total residual glucose and galactose was less than 10 mol %, which indicated that most monosugar was consumed in glycosylation. As the glucose content in the mixture gradually increased, the residual glucose increased from 0.9% to 7.6%, and the residual galactose decreased from 5.4% to 0.3%. The GaOS yield and selectivity showed no direct relationship with the glucose content, though the lowest glucose ratio (5 wt %) gave the lowest GaOS yield (17.7%), and the highest glucose ratio (95 wt %) gave the highest GaOS yield (30.7%) (FIG. 7B). It was very interesting that the GaOS yield of 25 wt % glucose ratio was obviously higher than that of 75 wt %. Further detailed study is required to figure out the reason.

Figure 8A:
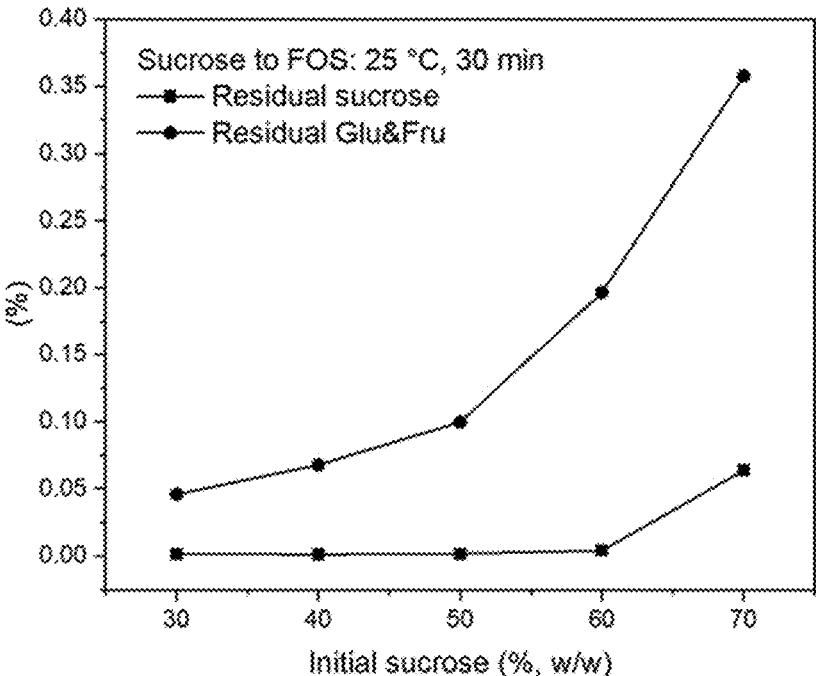
FIGS. 8A-8C show the effect of initial sucrose (30-70%, w/w) on FOS synthesis from sucrose glycosylation in 76 wt % wt $H_2SO_4$ at 25° C. for 30 min. (8A) residual sucrose yield and residual glucose and fructose yield; (8B) FOS yield and selectivity; (8C) yields of side products formic acid (FA), levulinic acid (LA), hydroxymethylfurfural (HMF) and levoglucosan (LGA).
Figure 8B:
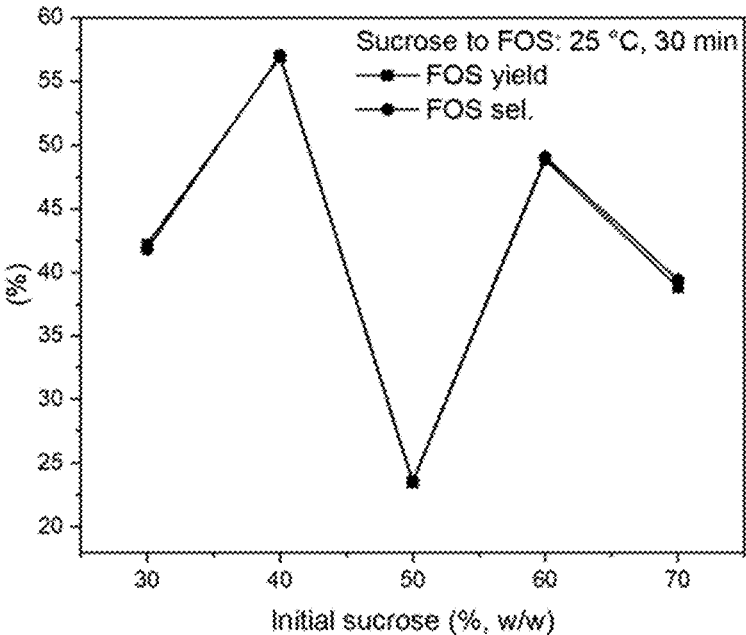
Figure 8C:
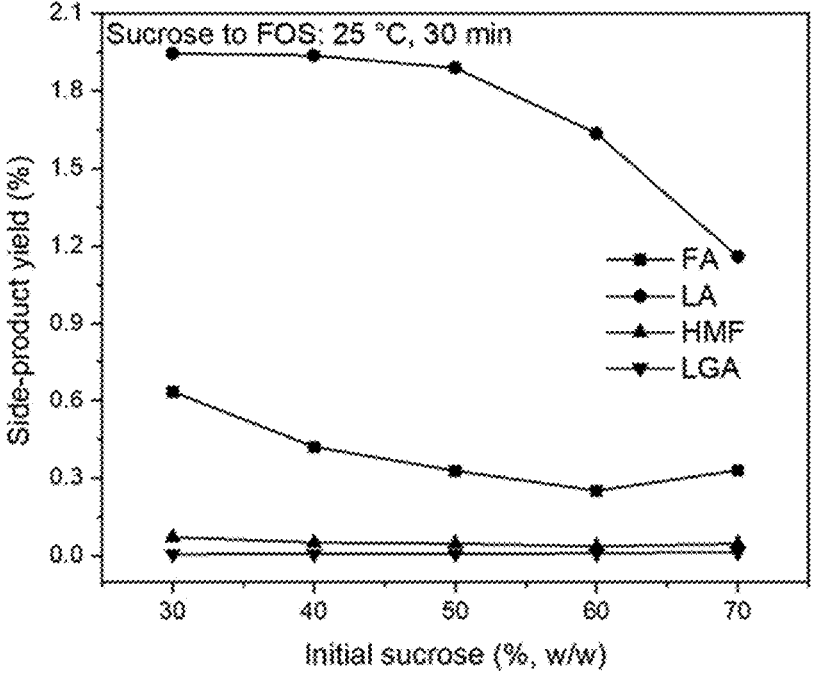

Example 4: Sucrose Glycosylation to FOS in Concentrated $H_2SO_4$ i. Effect of Initial Sucrose Concentration The effect of initial sucrose content on the synthesis of fructooligosaccharides (FOS) from sucrose glycosylation was shown in FIG. 8. After glycosylation in 76 wt % $H_2SO_4$ at 25° C. for 30 min, over 99.9 mol % sucrose was consumed, and the yield of glucose and fructose that derived from sucrose hydrolysis increased from 0.05% to 0.36% when initial sucrose increased from 30% to 70% (FIG. 8A). This indicated that sucrose conversion is very fast in concentrated $H_2SO_4$ even at moderate temperature. It can be seen from FIG. 8B that there is no direct relationship between initial sucrose and FOS yield/selectivity. The maximum FOS yield (56.9%) was obtained at 40% initial sucrose, while the minimum FOS yield (23.4%) was obtained at 50% initial sucrose. The FOS yield at 30% initial sucrose was very similar to that of 70% initial sucrose, which was 42.2% and 38.8%, respectively. As shown in FIG. 8C that the yield of reversible dehydration product LGA and irreversible dehydration product HMF was below 0.1%. The yield of FA and LA that derived from rehydration of HMF decreased with initial sucrose. The maximum FA, LA and HMF yield was obtained at 30% initial sucrose, which was 0.63%, 1.95% and 0.07%, respectively. In conclusion, 40% initial sucrose was the optimum for sucrose glycosylation at 25° C. for 30 min.

ii. Effect of $H_2SO_4$ Concentration

Figure 9A:
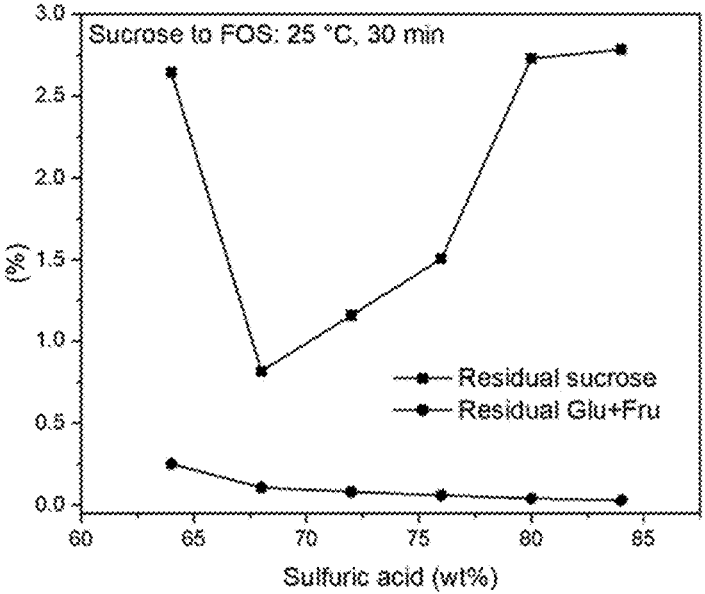
FIGS. 9A-9C show the effect of sulfuric acid concentration (64-84 wt %) on FOS synthesis from sucrose glycosylation in 40 wt % initial lactose at 25° C. for 30 min. (9A) residual sucrose yield and residual glucose and fructose yield; (9B) FOS yield and selectivity; (9C) yields of side products formic acid (FA), levulinic acid (LA), hydroxymethylfurfural (HMF) and levoglucosan (LGA).
Figure 9B:
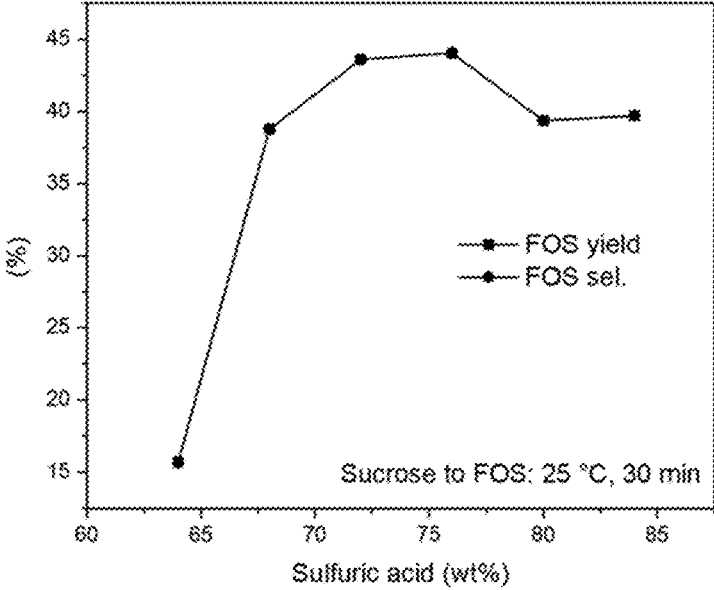
Figure 9C:
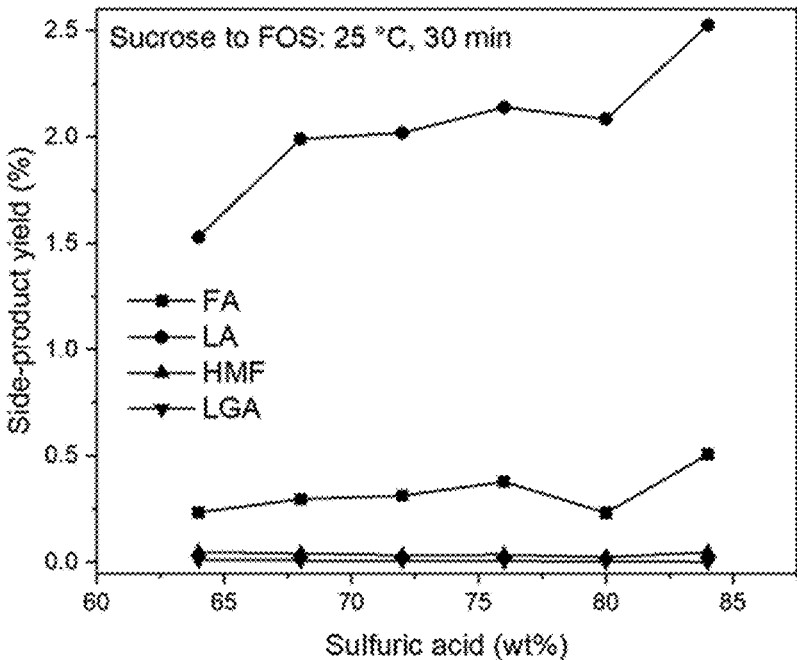
Figure 10A:
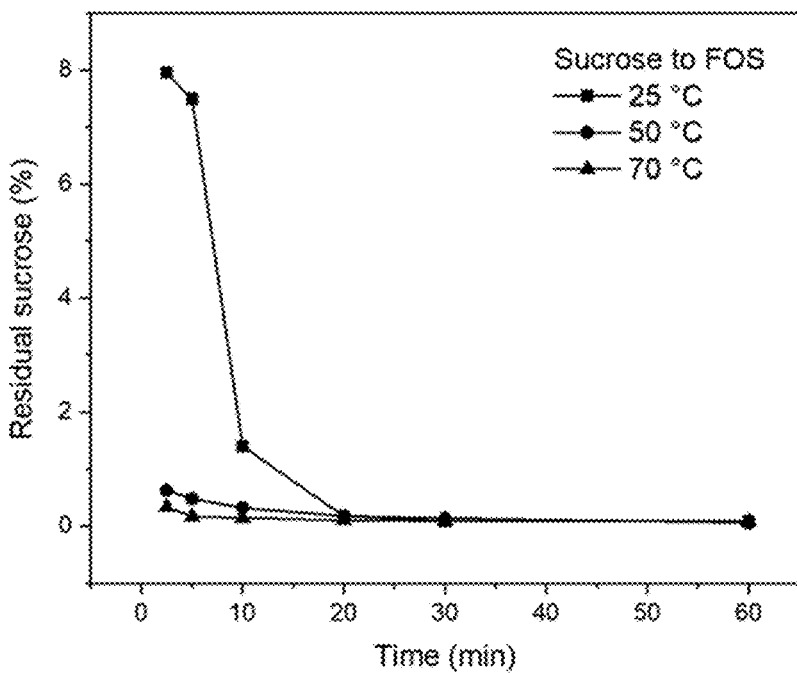
FIGS. 10A-10H show the effect of reaction temperature (25, 50 and 70° C.) on sucrose glycosylation to FOS with 50 wt % initial sucrose and 76 wt $H_2SO_4$% (10A) residual sucrose yield; (10B) residual glucose and fructose yield; (10C) FOS yield; (10D) FOS selectivity; (10E) FA yield; (10F) LA yield; (10G) HMF yield; (10H) LGA yield.
Figure 10B:
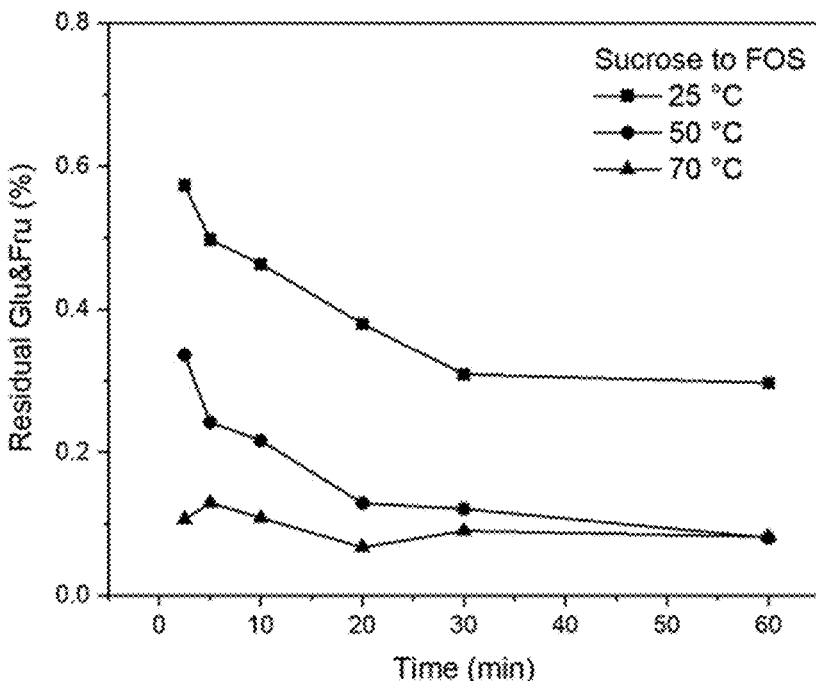
Figure 10C:
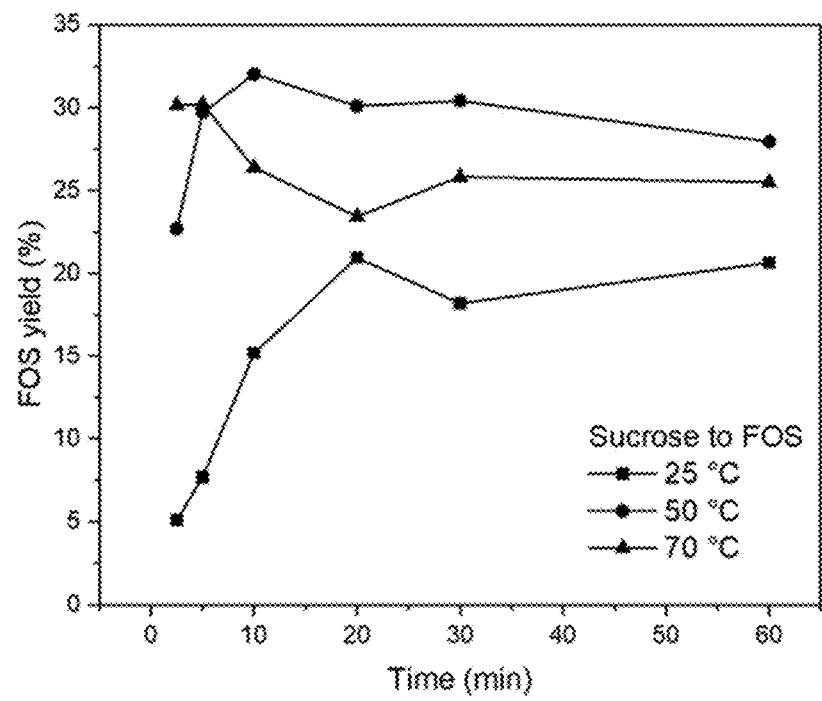
Figure 10D:
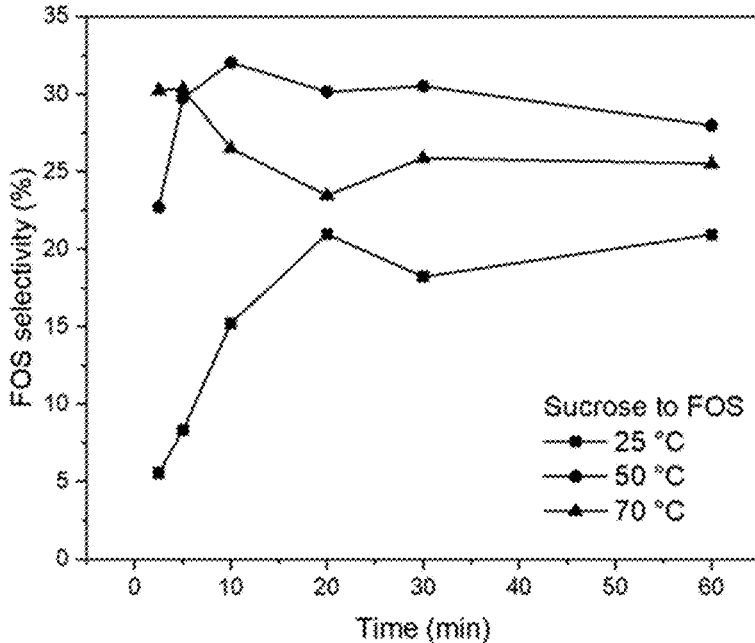
Figure 10E:
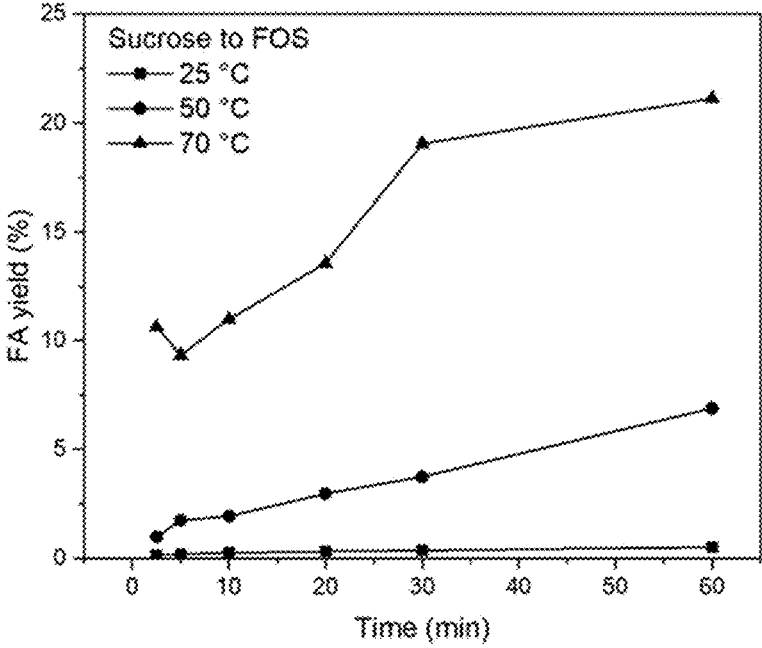
Figure 10F:
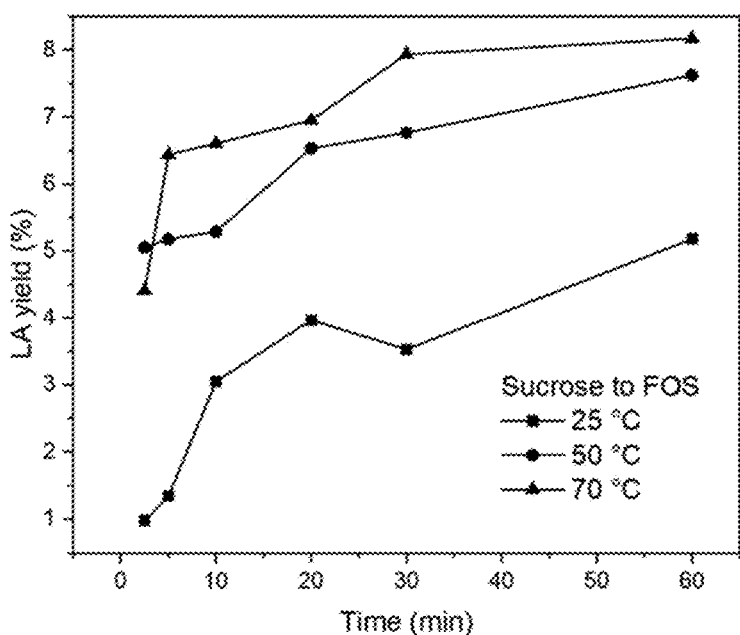
Figure 10G:
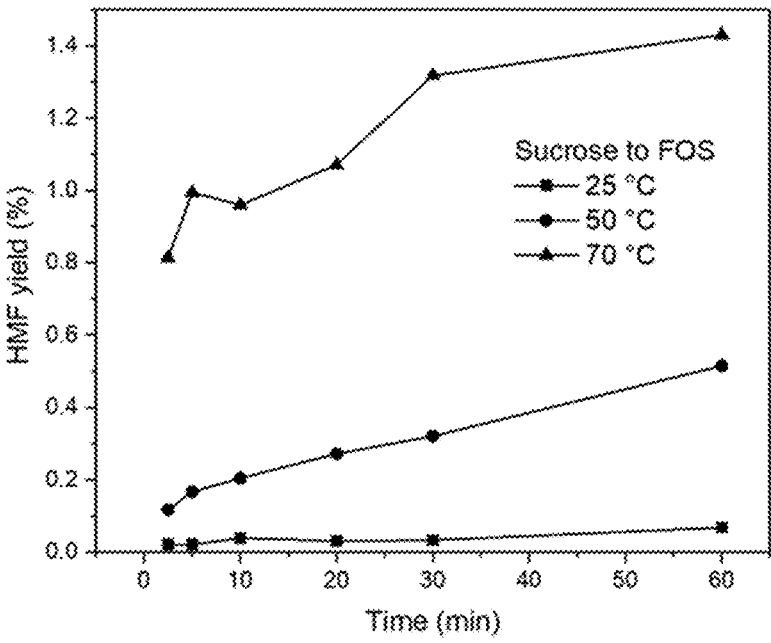
Figure 10H:
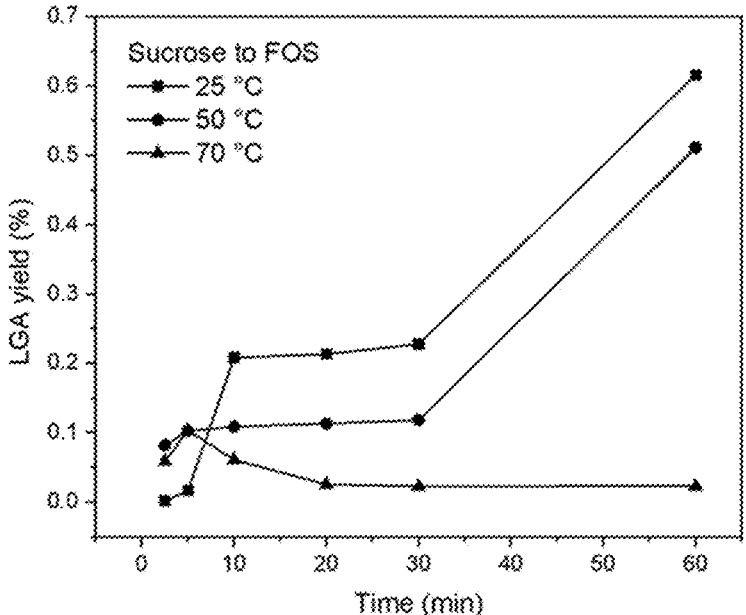

The effect of $H_2SO_4$ concentration on the synthesis of FOS from sucrose glycosylation was also studied. As shown in FIG. 9A, the residual sucrose decreased from 2.6% to 0.8% when $H_2SO_4$ increased from 64% to 68%, and then gradually increased to 2.8% when $H_2SO_4$ further increased to 84%. The yield of residual glucose and fructose gradually decreased with $H_2SO_4$ concentration, and was all below 0.5%. From FIG. 9B, the FOS yield increased obviously from 15.7% to 38.7% when $H_2SO_4$ increased from 64% to 68%, which was probably because more sucrose was consumed. The maximum FOS yield (44.0%) was obtained at 76% $H_2SO_4$, with FOS selectivity of 44.0%. Then the FOS yield and selectivity slightly decreased as $H_2SO_4$ further increased to 84%. This was probably because less sucrose was consumed, and more degradation products were formed at higher $H_2SO_4$ concentration (FIG. 9C). The yield of LGA decreased from 0.013% to 0.002% as $H_2SO_4$ increased from 64% to 84%. The yield of HMF yield was around 0.05% for all $H_2SO_4$ concentration, while the yield of FA and LA derived from HMF rehydration increased with $H_2SO_4$ concentration. The maximum FA, LA and HMF yield was 0.51%, 2.52% and 0.05%, respectively, with 84% $H_2SO_4$.

iii. Effect of Reaction Temperature

Figure 6A:
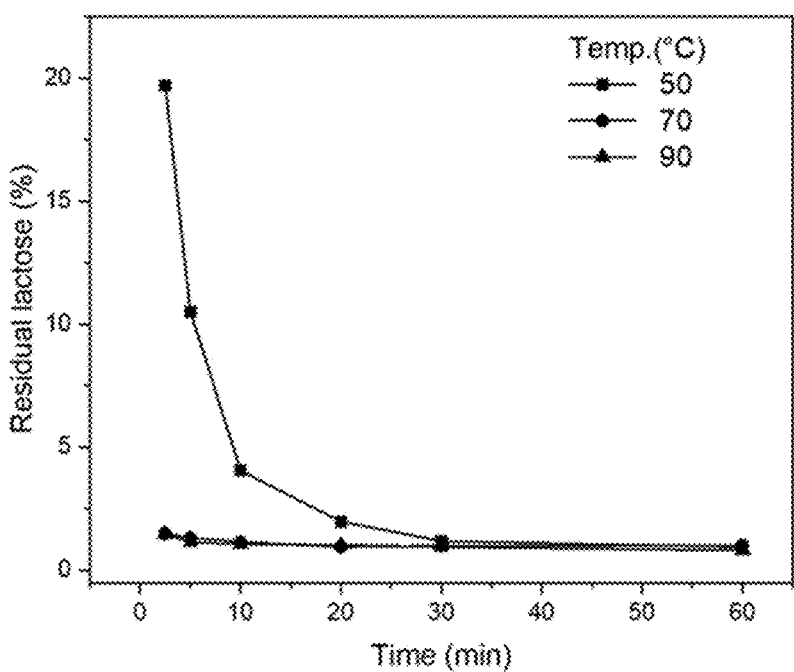
FIGS. 6A-6H show the effect of reaction temperature (50, 70 and 90° C.) on lactose glycosylation to GaOS with 50 wt % initial lactose and 76 wt $H_2SO_4$% (6A) residual lactose yield; (6B) residual glucose and galactose; (6C) GaOS yield; (6D) GaOS selectivity; (6E) formic acid yield; (6F) levulinic acid yield; (6G) HMF yield; (6H) LGA yield.
Figure 6B:
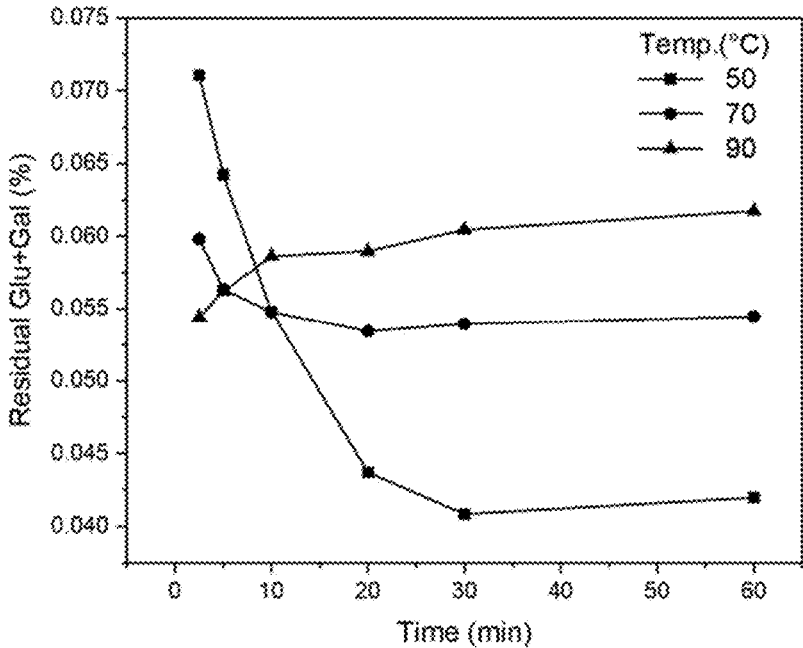
Figure 6C:
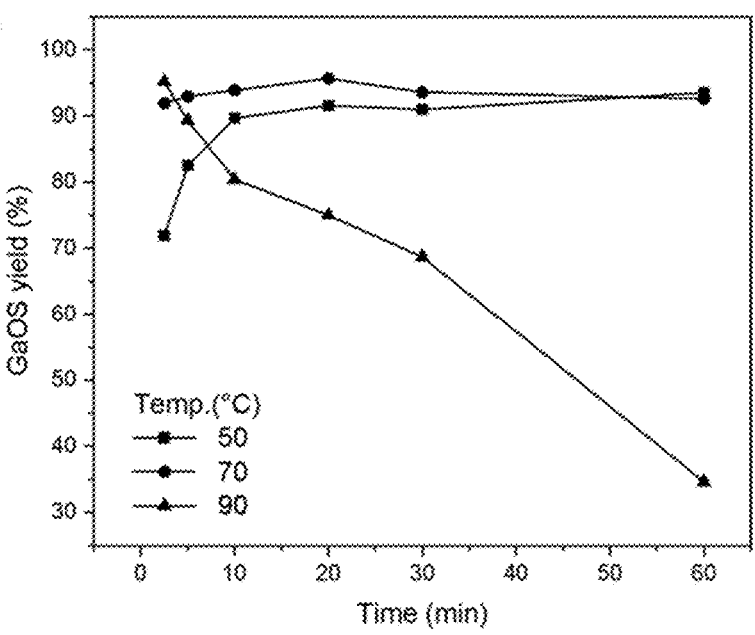
Figure 6D:
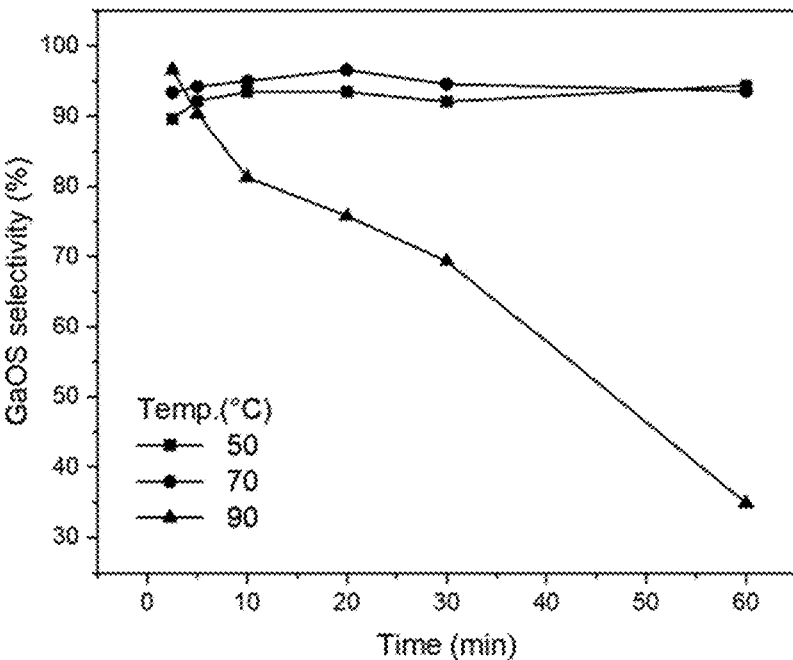
Figure 6E:
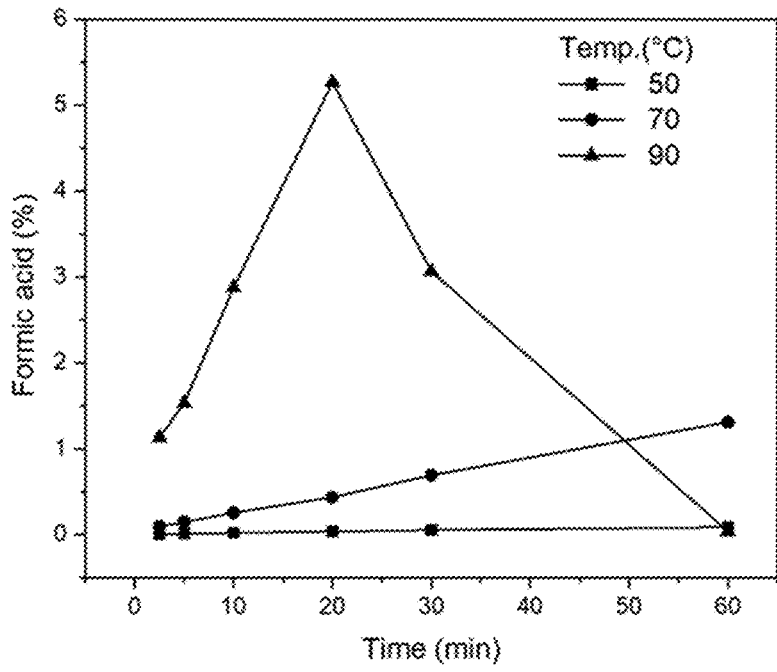
Figure 6F:
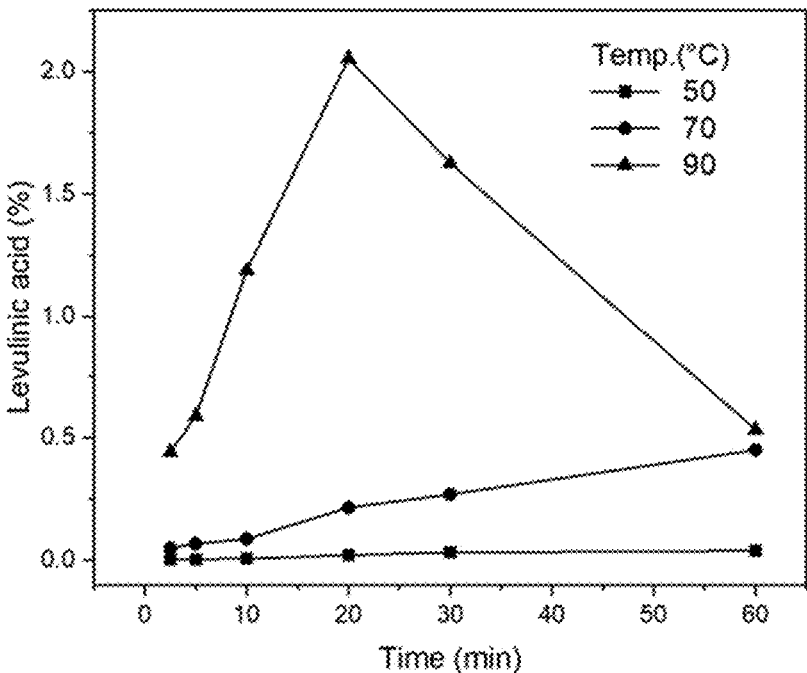
Figure 6G:
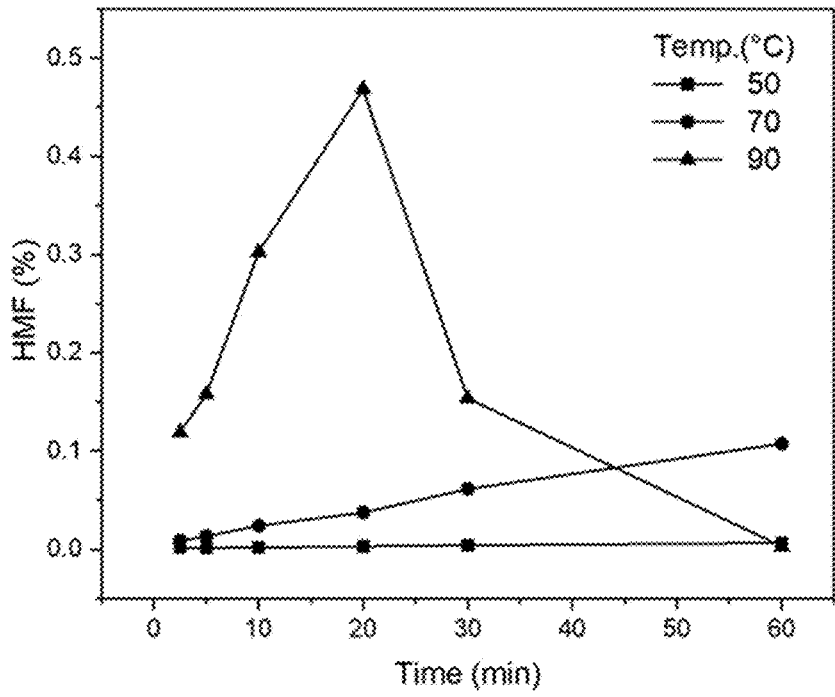
Figure 6H:
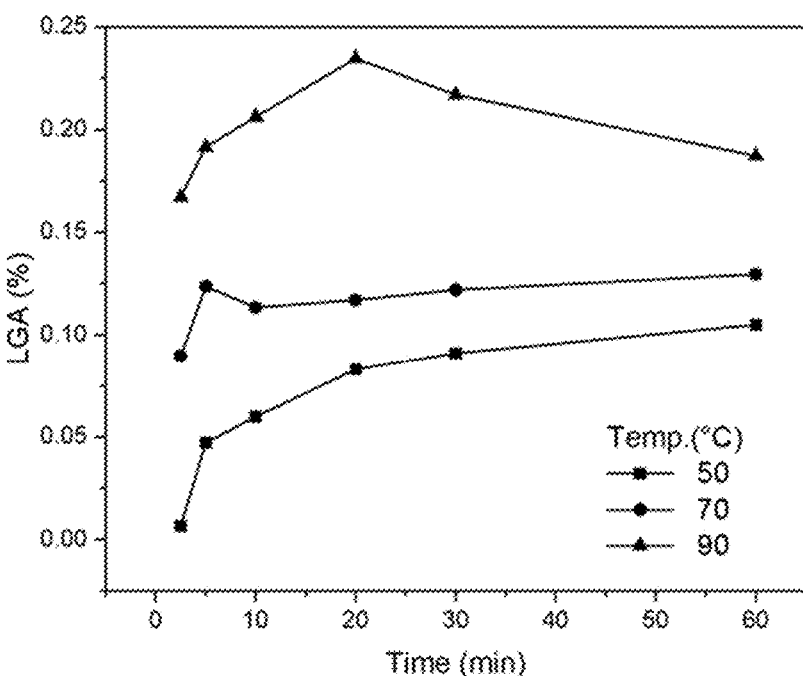

The effect of reaction temperature (25, 50 and 70° C.) on FOS synthesis from sucrose glycosylation was summarized in FIG. 10. From FIG. 10A, over 90 mol % sucrose was consumed at 25° C. within 2.5 min, and the residual sucrose gradually decreased with reaction time, with only 0.17 mol % sucrose remained at 20 min. When reaction temperature was elevated to 50° C., over 99 mol % sucrose was consumed within 2.5 min. The total yield of glucose and fructose from sucrose hydrolysis also decreased (FIG. 6B). This indicated that heating accelerated the conversion of sucrose, glucose and fructose. The FOS yield and selectivity at varied temperature was shown in FIGS. 10C and 10D. At 25° C., the FOS yield gradually increased and achieved maximum of 20.9% at 20 min. At 50° C., the maximum FOS yield (32.0%) was obtained at 10 min, while the maximum FOS yield at 70° C. (30.2%) was at 5 min. The yield of degradation products FA, LA, and HMF all increased with reaction temperature and time, which was in consistent with the results of GlOS/GaOS synthesis from glucose/lactose glycosylation. The yield of reversible dehydration product LGA was below 1.0%. The effect of temperature on FOS yield and selectivity of sucrose glycosylation was relatively similar to that of glucose glycosylation to GlOS. However, the FOS yield from sucrose glycosylation was relatively low (around 30%) compared to the yield of GlOS from glucose glycosylation and the yield GaOS from lactose glycosylation (around 90%). This was probably because, compared to lactose, sucrose is easier to be hydrolyzed to glucose and fructose. Also, fructose is more unstable than glucose and galactose, which can easily degrade to HMF, then rehydrated to form formic acid and levulinic acid in concentrated $H_2SO_4$.

Example 5: Glucose-Fructose Mixture Glycosylation to FOS

Figure 11A:
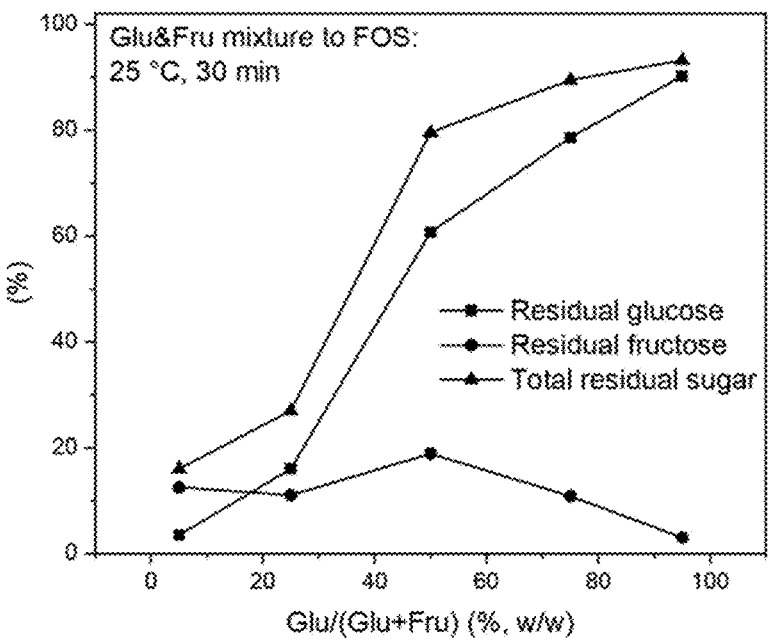
FIGS. 11A-11D show glucose-fructose mixture glycosylation to FOS at 25° C. for 30 min. The glycosylation was conducted at 50 wt % initial sugar (glucose and fructose) and 76 wt % $H_2SO_4$ (11A) residual glucose and fructose; (11B) FOS yield and selectivity; (11C) side-product yield of HMF; (11D) side-product yield of LGA.
Figure 11B:
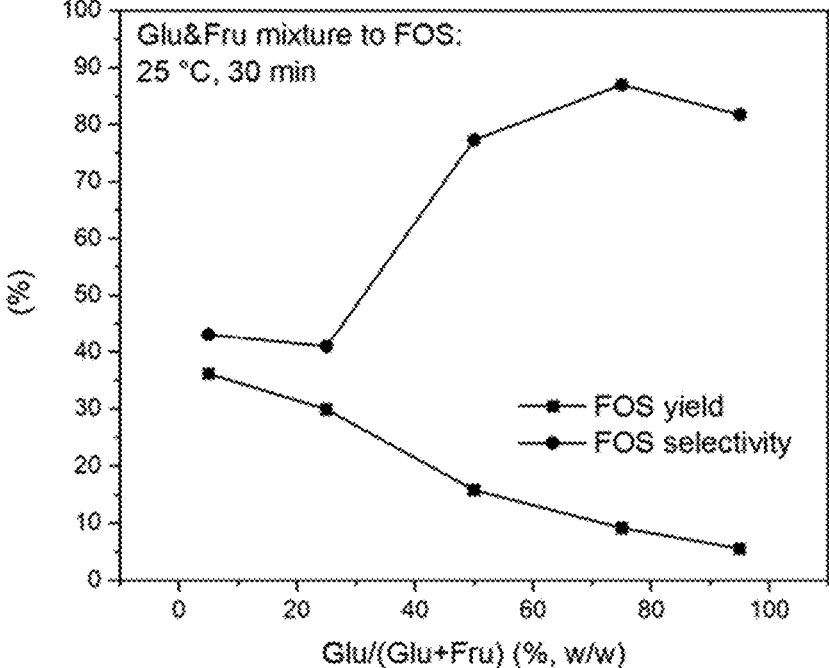
Figure 11C:
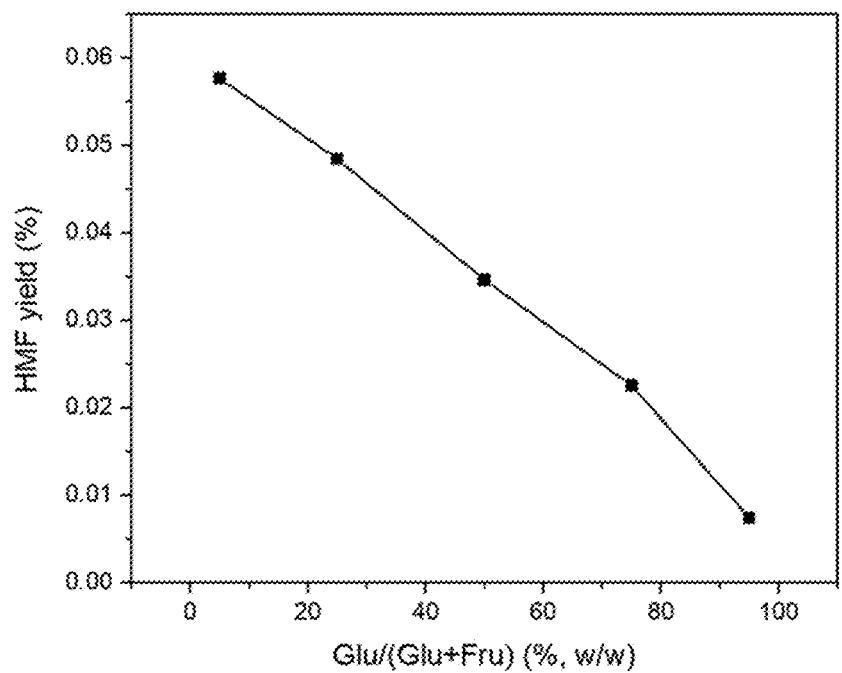
Figure 11D:
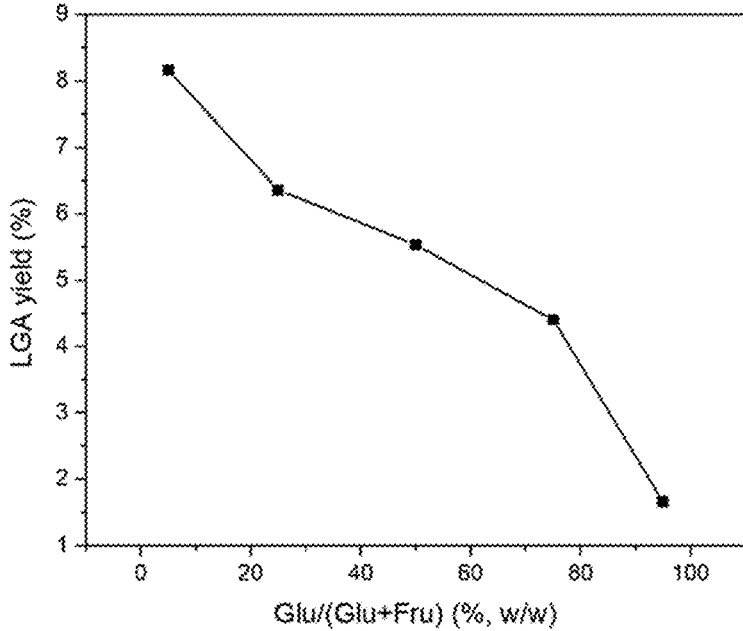

A mixture of glucose and fructose with different glucose ratio (5-95 wt %, mass of glucose to the mass of glucose and fructose) was used to synthesize FOS. The glycosylation was conducted with 50 wt % initial sugar (total) in 76 wt % $H_2SO_4$ at 25° C. for 30 min, and the result was shown in FIG. 11. As shown in FIG. 11A, around 80 mol % monosugars (glucose and fructose) was consumed when glucose was 5 wt %. As the glucose ratio gradually increased, the residual glucose increased obviously, which explained the increase of the total residual sugar. The residual fructose was below 20 mol % for all the glucose ratio, which suggested that fructose is easier to be consumed than glucose at this condition. From FIG. 11B, the FOS yield decreased from 36.2% to 5.6% as the glucose ratio increased from 5 wt % to 95 wt %, which was probably because large amount of glucose was remained unused. The FOS selectivity slightly decreased (around 40%) when the glucose ratio was between 5 and 25 wt %, then increased to around 80% when the glucose ratio was equal or greater than 50 wt %, which indicated that higher glucose ratio corresponded to higher FOS selectivity. From FIGS. 11C and 11D, the irreversible dehydration product HMF and reversible dehydration product LGA both gradually decreased as the glucose ratio increased. This suggested that fructose is easier dehydrated to side products than glucose, and this explained why the FOS selectivity was lower at lower glucose ratio.

Figure 12A:
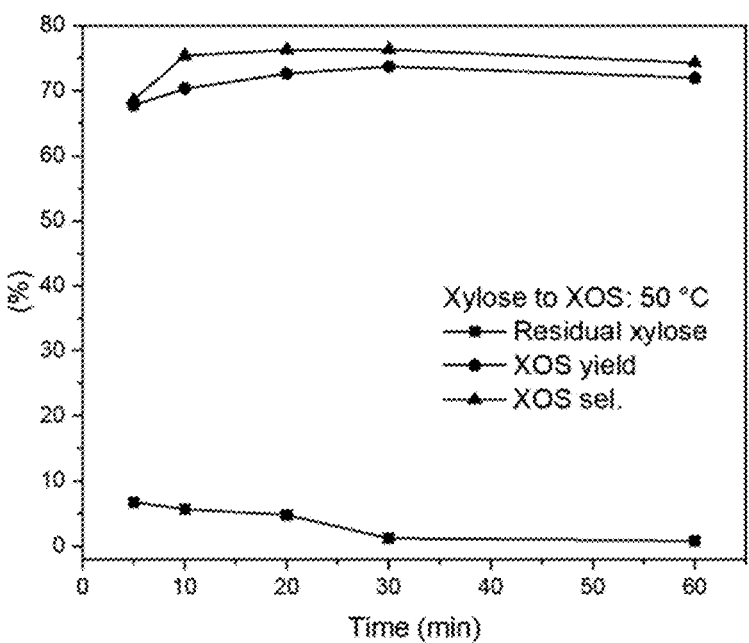
FIGS. 12A-12B show xylose glycosylation to XOS at 50° C., with 50 wt % initial xylose and 76 wt % $H_2SO_4$: (12A) residual xylose yield, XOS yield and selectivity; (12B) yields of side-product formic acid, levulinic acid and furfural.

Example 6: Xylose Glycosylation to Xylooligosaccharides (XOS) in Concentrated $H_2SO_4$ The synthesis of xylooligosaccharides (XOS) from xylose glycosylation in concentrated $H_2SO_4$ was summarized in FIG. 12. The xylose glycosylation was conducted at 50° C.

22 glycosylated in 76 wt % $H_2SO_4$ at 50° C., 20 min to synthesize the corresponding oligosaccharides. As shown in Table 2, mannose, a C-2 epimer of glucose, was glycosylated to mannooligosaccharides (MOS) with 84.9% yield and 91.4% MOS selectivity. The total yield of side-product (FA, LA and HMF) for mannose glycosylation was only 0.45%. Similarly, galactooligosaccharides (GaOS) was synthesized from monosugar galactose (C-4 epimer of glucose) with a yield of 88.9% and 94.1% selectivity. Maltose and cellobiose are disaccharides that consisting of two glucose units linked by $\alpha$-1,4 and $\beta$-1,4 glycosidic bond, respectively. After 20 min glycosylation in 76 wt % $H_2SO_4$, 93.4 mol % maltose was converted and yielded 78.1% maltooligosaccharides (MOS) with 83.6% selectivity. Similarly, cellobiose was glycosylated to cellooligosaccharides with 80.2% yield and 84.8% selectivity. The total yield of side-products for maltose/cellobiose glycosylation was very low. The results above indicated that the oligosaccharides could be synthesized from different sugar substrates with good yield and selectivity in concentrated $H_2SO_4$.

TABLE 2

| Application of concentrated $H_2SO_4$ in various sugar glycosylation reactions | | | | | | | |
|---|---|---|---|---|---|---|---|
| Target oligosaccharides | Substrate | Residual substrate (%) | Yield (%) | Sel. (%) | Side-product (%) | | |
| | | | | | FA | LA | HMF |
| mannooligosaccharides | mannose | 7.1 | 84.9 | 91.4 | 0.25 | 0.19 | 0.0104 |
| galactooligosaccharides | galactose | 5.5 | 88.9 | 94.1 | 0.03 | 0.02 | 0.0017 |
| maltooligosaccharides | maltose | 6.6 | 78.1 | 83.6 | 0.02 | 0.08 | 0.0037 |
| cellooligosaccharides | cellobiose | 5.5 | 80.2 | 84.8 | 0.03 | 0.02 | 0.0041 |

Figure 12B:
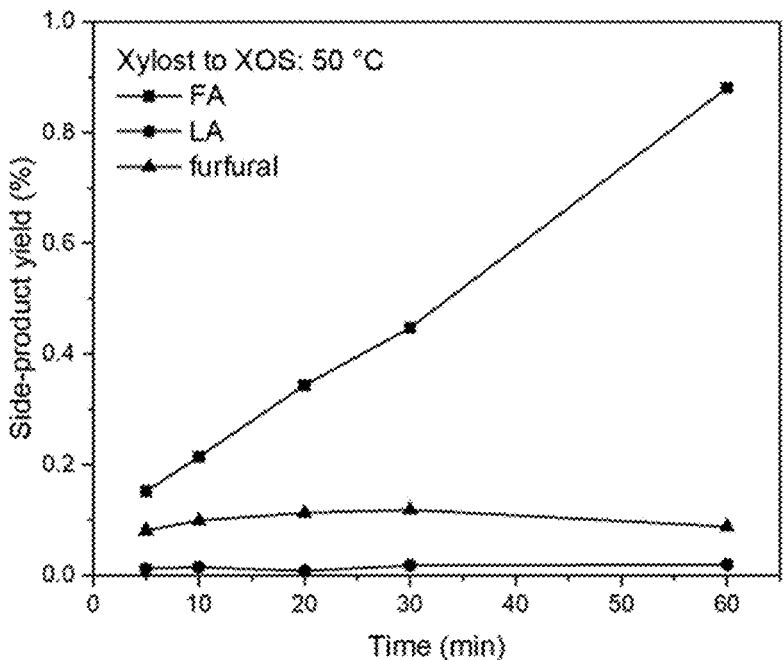

Glycosylation condition: 50° C., 20 min, 76 wt % $H_2SO_4$, 50 wt % initial sugar for 5-60 min. Over 90 mol % xylose was consumed at 5 min, and the residual xylose gradually decreased with reaction time, with only 0.8 mol % xylose remained at 60 min. At 50° C., the XOS yield was as high as 67.7% at 5 min, and remained above 70% at the rest of glycosylation. The maximum XOS yield was obtained at 30 min, which was 73.7% with 76.3% XOS selectivity. Then, the XOS yield slightly decreased to 71.2% as reaction time extended to 60 min, which was mainly because the more degradation products were formed at this time (FIG. 12B). Irreversible dehydration of xylose formed furfural, followed by subsequent decomposition of furfural to form formic acid (FA) and levulinic acid (LA). At 60 min, the yield of FA, LA and furfural was only 0.88%, 0.02% and 0.09% respectively. Therefore, it is effective to synthesize XOS from xylose glycosylation in concentrated $H_2SO_4$.

Example 7: Synthesis of Various Oligosaccharides in Concentrated $H_2SO_4$

In previous sections, concentrated $H_2SO_4$ was proved to be an effective solvent for the synthesis of GlOS, GaOS, FOS, XOS from glycosylation of different sugar substrates. In order to test the applicability of concentrated $H_2SO_4$ in glycosylation reaction, four different sugar substrates were

Example 8: Sugar Mixture Glycosylation to Oligosaccharides

The synthesis of oligosaccharides from glycosylation of a mixture of monosugars or disaccharides was studied. Equal amount (0.001 mol) of glucose, galactose, fructose, mannose, xylose and arabinose was mixed together (total 0.006 mol) and glycosylated in 76 wt % $H_2SO_4$ at 50° C. for 10 min, and the result was summarized in Table 3. The residual monosugar (mol %) reflected the amount of the monosugar that was consumed. Only 3.89 mol % fructose was remained, followed by galactose and mannose (around 6.90%), then xylose and arabinose (around 11.50%), and glucose was the highest (12.20%). This suggested that fructose is the most reactive monosugar, probably because it's easily dehydrated to HMF in concentrated $H_2SO_4$. Galactose and mannose are relatively reactive towards glycosylation, compared to xylose, arabinose and glucose. Overall, only 8.80 mol % monosugars were remained, which indicated that most monosugars were consumed after glycosylation. The resultant oligosaccharides had a yield of 65.81% with 72.17 selectivity. The total yield of side-products was 4.56%, in which formic acid (FA) was the most abundant one (2.53%) while furfural was the least (only 0.11%).

TABLE 3

The synthesis of oligosaccharides from a mixture of monosugars

| Substrate | Residual monosugar[a] (%) | Total residual sugars[b] (%) | Oligosaccharides Yield (%) | Sel. (%) | Side-product (%) FA | LA | HMF | furfural |
|---|---|---|---|---|---|---|---|---|
| glucose | 12.20 | 8.80 | 65.81 | 72.17 | 2.53 | 1.76 | 0.16 | 0.11 |
| galactose | 6.86 | | | | | | | |
| fructose | 3.89 | | | | | | | |
| mannose | 6.90 | | | | | | | |
| xylose | 11.50 | | | | | | | |
| arabinose | 11.46 | | | | | | | |

Glycosylation condition: 50° C., 10 min, initial sugar (total) 30 wt %, 76 wt % $H_2SO_4$
[a]The ratio of residual monosugar after glycosylation (mol) to monosugar before glycosylation (mol)
[b]The ratio of total residual monosugar (mol) to total monosugar before glycosylation (mol)

Figure 13:
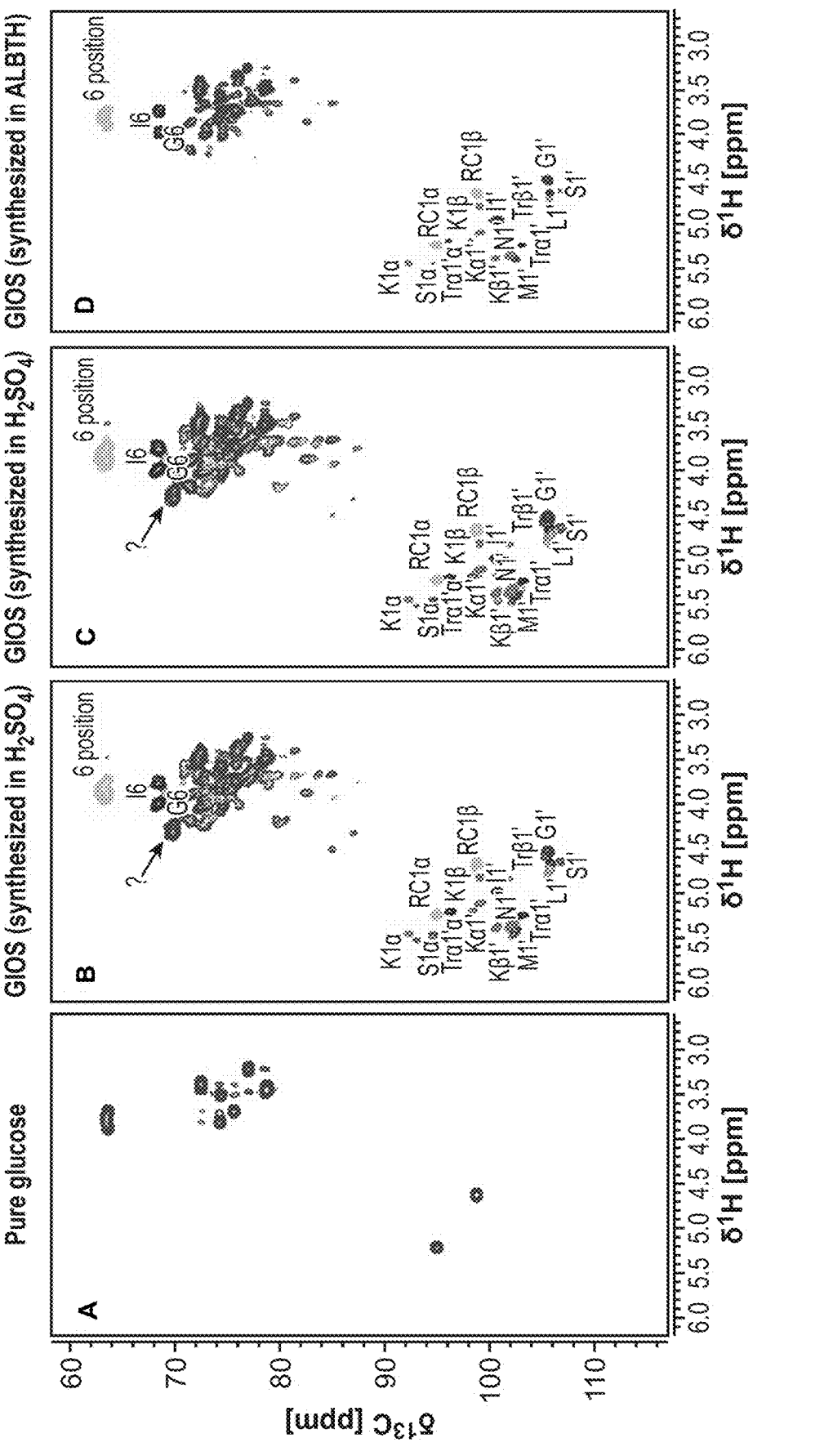
FIG. 13 shows a $^1$H-$^{13}$C HSQC NMR analysis of the glycosidic bonds in the GlOS samples. 13A. pure glucose; 13B. GlOS synthesized in $H_2SO_4$ at 40% (m/v) glucose loading and 30° C.; 13C. GlOS synthesized in $H_2SO_4$ at 100% (m/v) glucose loading and 30° C.; 13D. GlOS synthesized in ALBTH at 100% (m/v) glucose loading and 70° C.

Similarly, equal amount (0.001 mol) of disaccharide lactose, sucrose, cellobiose and maltose (total 0.004 mol) was mixed and glycosylated in 76 wt % $H_2SO_4$ at 50° C. for 10 min. It can be seen from Table 4 that, for every disaccharide, over 95 mol % was consumed after glycosylation, while different disaccharide showed different reactivity. Sucrose (glucose and fructose with $\alpha$-1,2 linkage) was the least remained disaccharide, which probably because $H_2SO_4$ accelerated the hydrolysis of sucrose to glucose and fructose. Cellobiose ($\beta$-1,4 linkage) should be more reactive compared to maltose ($\alpha$-1,4 linkage), though they both consisted of two glucose units. The yield of monosugars that derived from the hydrolysis of disaccharides was 7.79%, with 6.44% glucose, 0.78% galactose and 0.57% fructose, which suggested that glucose is the most stable monosugar, followed by galactose and fructose is the most reactive monosugar. This result is in consistent with the glycosylation of monosugar mixture. The yield of the oligosaccharides from disaccharide mixture was 77.73% with a selectivity of 78.89%, which was relatively higher than that of monosugar mixture. The total yield of side-products was 3.35%, with 1.99% formic acid (FA), 1.16% levulinic acid (LA) and 0.20% 5-hydroxymethylfurfural (HMF).

the filtrate was freeze-dried to yield the GlOS crystals. The glycosidic bonds in GlOS were investigated by 2D NMR, as shown in FIG. 13. Various glycosylic bonds including $\alpha/\beta$-1,1, $\alpha/\beta$-1,2, $\alpha/\beta$-1,3, $\alpha$-1,4, and $\alpha/\beta$-1,6 were identified in GlOS synthesized in 72% $H_2SO_4$. The glucose glycosylation in 72% $H_2SO_4$ was thus confirmed, in consistency with our HPIC results. The glycosylation pattern in the anomeric region was similar to that by the ALBTH method. While a correlation contour at $\delta^{13}C/\delta^1H$ 69.7/4.25 ppm exclusively appeared in the GlOS samples synthesized in 72% $H_2SO_4$. This contour was not assigned since it differed from the contours of glucose and disaccharide standards. In the future research, identification of this contour peak may be helpful to probe the side-reactions during the glycosylation in 72% $H_2SO_4$.

Glucooligosaccharides (GlOS) were successfully synthesized via the glycosylation in concentrated $H_2SO_4$ at mile condition (30° C.) with a one-pass yield of about 90%.

The GlOS have similar structures to those synthesized in a LiBr system (Pan, X. and Li, N., "Methods of producing oligosaccharides for use as prebiotics" U.S. Pat. No. 10,711, 022B2.). The glycosidic bonds newly formed in GlOS were investigated and confirmed by 2D NMR, as shown in FIG.

TABLE 4

The synthesis of oligosaccharides from a mixture of disaccharides

| Substrate | Residual disaccharide[a] (%) | Residual monosugars[b] (%) | Oligosaccharides Yield (%) | Sel. (%) | Side-product (%) FA | LA | HMF |
|---|---|---|---|---|---|---|---|
| lactose | 3.29 | 7.79 | 77.73 | 79.89 | 1.99 | 1.16 | 0.20 |
| sucrose | 1.85 | | | | | | |
| cellobiose | 1.88 | | | | | | |
| maltose | 3.77 | | | | | | |

Glycosylation condition: 50° C., 10 min, initial sugar (total) 30 wt %, 76 wt % $H_2SO_4$
[a]The ratio of residual disaccharide after glycosylation (mol) to initial disaccharide before glycosylation (mol)
[b]The ratio of monosugars (glucose, galactose and fructose) derived from the hydrolysis of disaccharides Example 9: Preliminary Characterization and Prebiotic Activities of the Oligosaccharides Synthesized in Concentrated Acids i. Characterization of the Glucooligosaccharides from Glucose Via Glycosylation in Concentrated $H_2SO_4$ After the glucose glycosylation in 72% $H_2SO_4$, the reaction mixture in 72% $H_2SO_4$ was neutralized by $CaCO_3$. The resultant $CaSO_4$ precipitate was removed by filtration and 13. Various glycosylic bonds including $\alpha/\beta$-1,1, $\alpha/\beta$-1,2, $\alpha/\beta$-1,3, $\alpha$-1,4, and $\alpha/\beta$-1,6 were identified in GlOS synthesized in $H_2SO_4$.

ii. Preliminary Evaluation of the Oligosaccharides Synthesized in Concentrated Acids Via In Vitro Fermentation The concentrations of short-chain fatty acids (SCFAs) and residual sugars after 24 h-*Lactobacillus* fermentation were analyzed by HPLC and HPIC, as shown in FIGS. 14 and 15, respectively. Lactic acid and acetic acid were the major acids produced by *Lactobacillus* fermentation. The lactic acid concentrations varied from 1.6-4.2 g/L, 1.9-3.3 g/L, 1.4-2.7 g/L, 1.1-4.4 g/L, and 2.6-5.8 g/L in GlOS, GOS from galactose, GOS from lactose, FOS from fructose, and FOS from sucrose, respectively. The acetic acid concentrations varied from 0.4-1.5 g/L, 0.4-1.5 g/L, 0.2-1.5 g/L, 0.4-1.1 g/L, and 0.4-0.9 g/L in GlOS, GOS from galactose, GOS from lactose, FOS from fructose, and FOS from sucrose, respectively. Concentrations of the formic acid, propionic acid, and butyric acid was less 0.3, 0.4, and 0.1 g/L, respectively, in all the samples.

Figure 16:
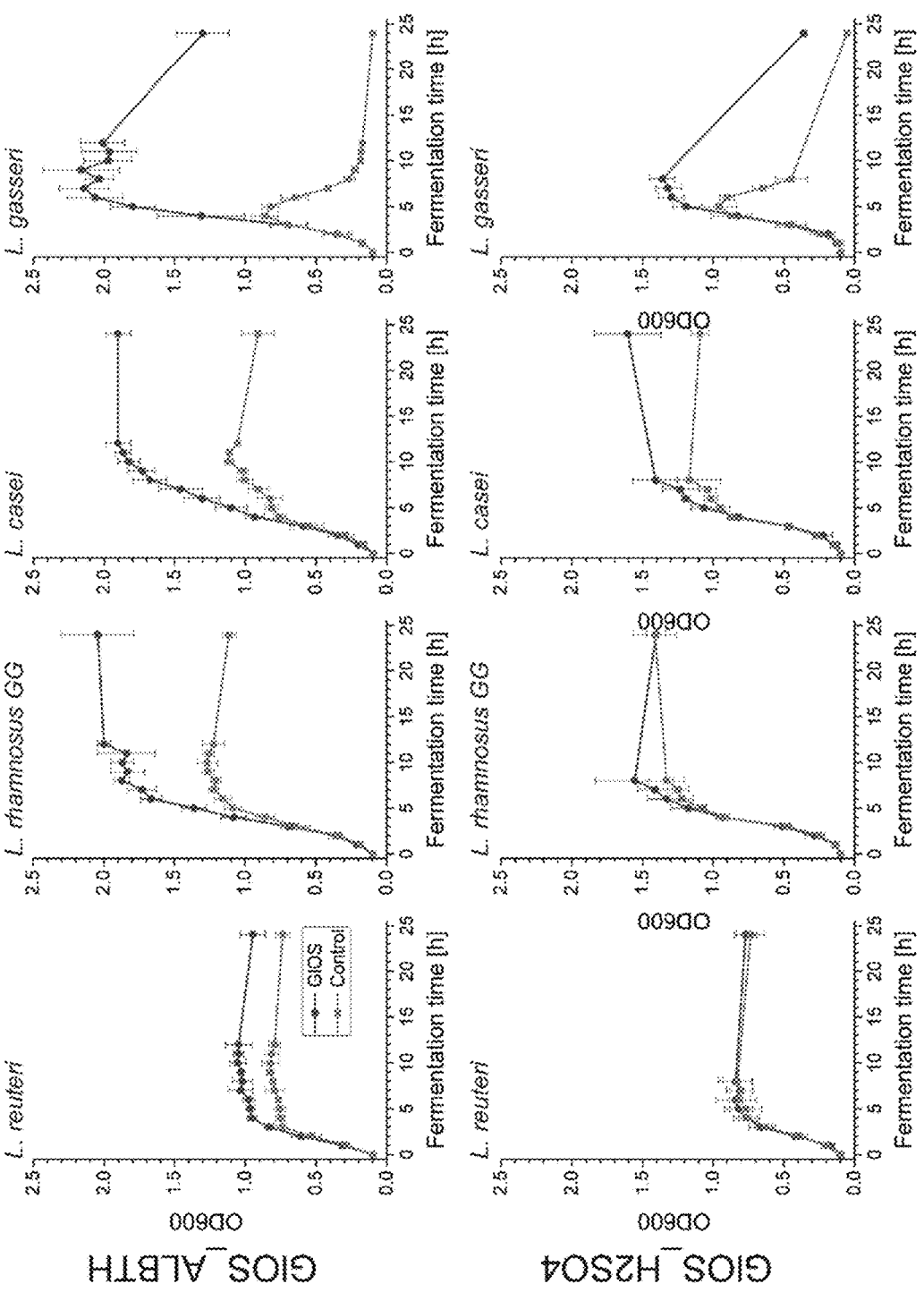
FIG. 16 shows growth curves of *L. reuteri* (ATCC 6475), L. rhamnonsus GG, *L. casei* BFLM 218, L. gasseri ATCC 33323 using GlOS_ALBTH (9.5 g/L GlOS+0.5 g/L glucose) with minimal glucose control (0.5 g/L) and GlOS_$H_2SO_4$ (9.2 g/L GlOS+0.8 g/L glucose) with minimal glucose control (0.8 g/L) as the carbon source.
Figure 17:
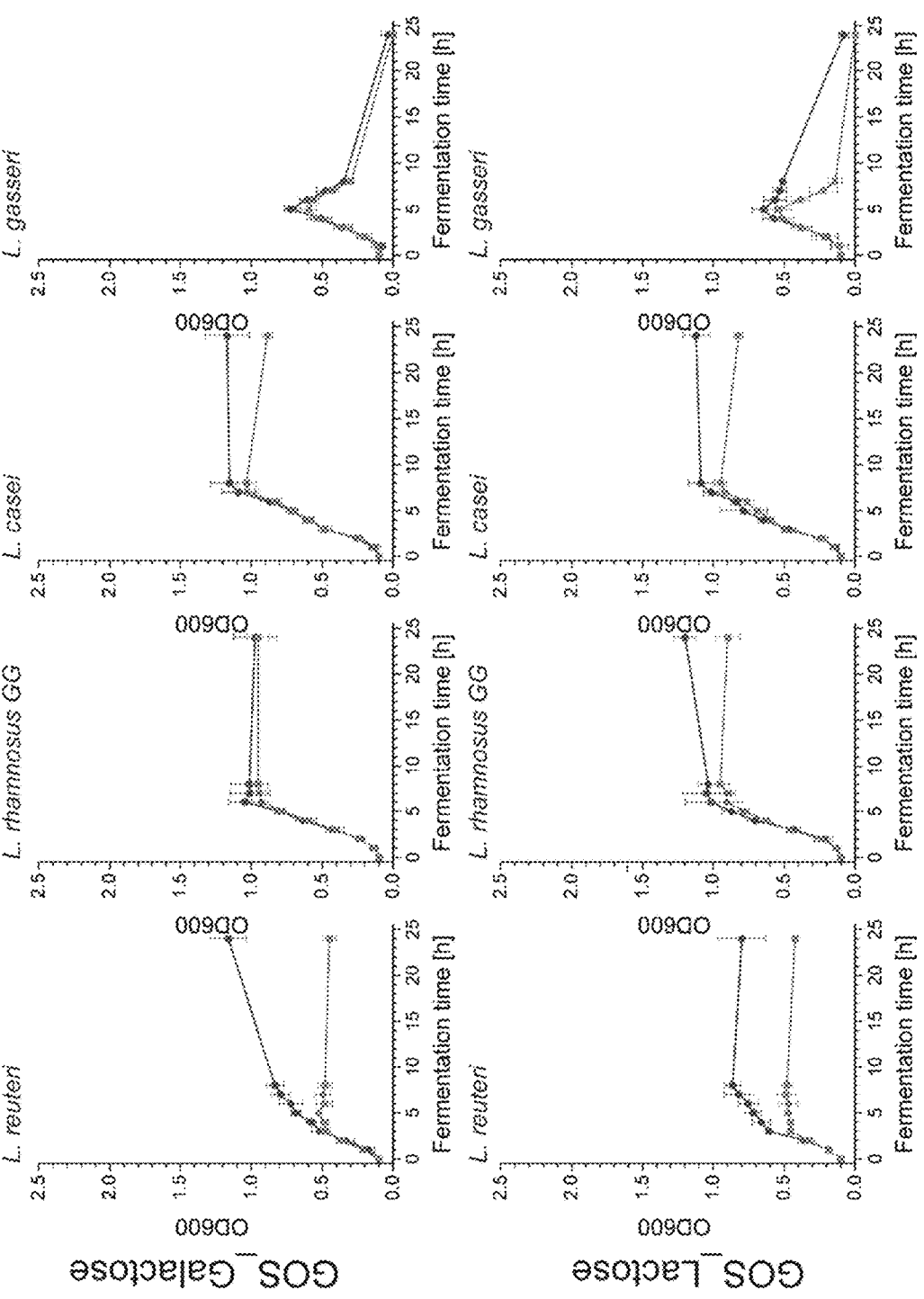
FIG. 17 shows growth curves of *L. reuteri* (ATCC 6475), L. rhamnonsus GG, *L. casei* BFLM 218, L. gasseri ATCC 33323 using GOs_galactose (9.8 g/L GOS+0.2 g/L galactose) with minimal sugar control (0.2 g/L galactose) and GOS_lactose (9.9 g/L GOS+0.1 g/L galactose) with minimal sugar control (0.1 g/L galactose) as the carbon source.
Figure 18:
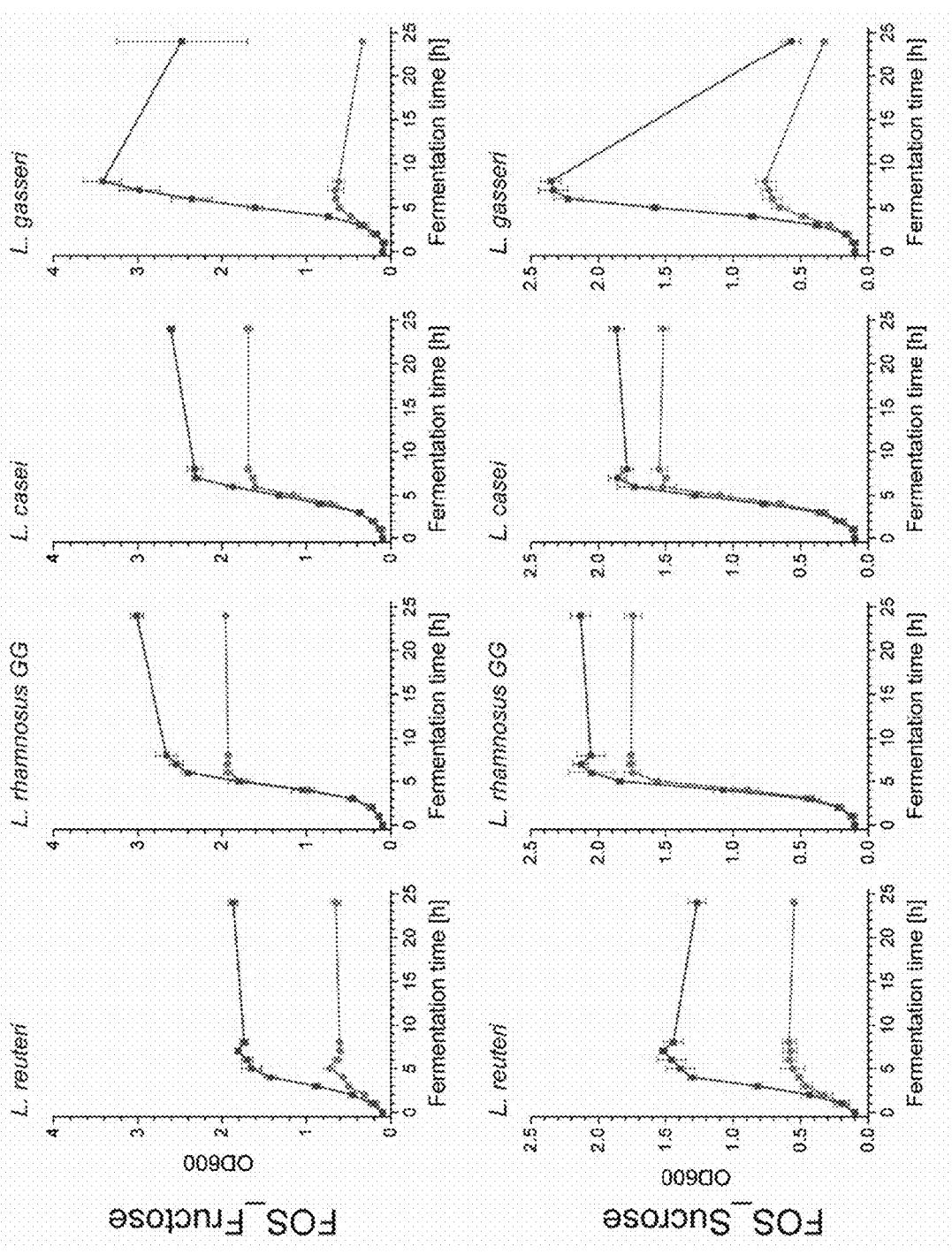
FIG. 18 shows growth curves of *L. reuteri* (ATCC 6475), L. rhamnonsus GG, *L. casei* BFLM 218, L. gasseri ATCC 33323 using FOS Fructose (7.8 g/L FOS+2.2 g/L fructose) with minimal sugar control (2.2 g/L fructose) and FOS Sucrose (6.8 g/L FOS+2.2 g/L glucose+0.8 g/L+0.2 g/L sucrose) with minimal sugar control (2.2 g/L glucose+0.8 g/L fructose+0.2 g/L sucrose) as the carbon source.

The SCFA concentrations were mostly consistent with the *Lactobacillus* growth curves as shown in FIGS. 16, 17, and 18. For example, SCFA concentrations of the GlOS_$H_2SO_4$ sample by *L. reuteri* were comparable to the control, in accordance with the overlapped growth curves. In cases that oligosaccharides favored the growth of *Lactobacillus* (GlOS by *L. casei*, GOS by *L. reuteri*, and FOS by *L. casei* and L. GG), lactic acid concentration was significantly higher the control while acetic acid concentration was indistinguishable. It indicates that oligosaccharides as the carbon source contributed to increase in lactic acid production.

The concentrations of mono- and disaccharides after 24 h fermentation were monitored. Glucose in GlOS and FOS2 samples were fully consumed in all test *Lactobacillus* strains. In the GOS1 and GOS2 samples, the initial concentrations of galactose and glucose were at a minimal level and these sugars kept insignificant after the fermentation. While 0.05-0.17 g/L and 0.14-0.25 g/L of lactose were formed from the *Lactobacillus* fermentation in GOS1 and GOS2 samples, respectively. The consumption of fructose in FOS1 and FOS2 samples were retarded. The residual fructose concentration was higher in oligosaccharide samples than the control. It suggests the *Lactobacillus* strains tended to favor the fructooligosaccharide consumption than the fructose consumption.

Example 10: Test of Different Mineral Acids and Acetic Acid

Different mineral acids were tested to see whether any would be an effective reaction medium for GlOS synthesis from glucose glycosylation to. As shown in Table 5, only phosphoric acid and sulfuric acid are effective reaction mediums for GlOS synthesis, while the rest of mineral acids are not. Boric acid has very low solubility in water even at high temperature (19.1 g/100 mL water, 80° C.), and its acidity is very weak. Acetic acid is miscible with water, but glucose has very limited solubility in the aqueous solution of acetic acid. Nitric acid is a very strong oxidant and glucose was oxidized to form carboxylic acid like D-glucaric acid. Hydrochloric acid is a strong, not oxidative acid, and glucose is well dissolved in the HCl aqueous solution. However, no glycosylation products were detected probably because the HCl is not concentrated enough for the glycosylation reaction (dehydration reaction), and the water content is too high (over 60%). Previous results (in the main manuscript) showed that phosphoric acid worked, but it required higher acid concentration, higher temperature, and longer reaction time to yield comparable glycosylation products compared to sulfuric acid.

Example 11: Applicability to Various Sugar Substrates

The result in the main manuscript proved that the concentrated sulfuric acid worked as the reaction medium to synthesize oligosaccharides from a variety of sugar substrates, including monosaccharides glucose, galactose, fructose, mannose, xylose, arabinose, and disaccharides lactose, sucrose, maltose, cellobiose, individually or in combination, as summarized in Table 6. During the glycosylation of glucose, the formed disaccharides like isomaltose and gentiobiose ($\alpha$-, $\beta$-1,6 linked) can be further glycosylated to higher DP oligosaccharides.

TABLE 6

| Synthesis of oligosaccharides from various substrates using concentrated sulfuric acid | | | | |
| --- | --- | --- | --- | --- |
| Target oligosaccharides | Abbreviation | substrate 1 | substrate 2 | substrate 3 |
| glucooligosaccharides | GlOS | glucose | maltose | cellobiose |
| galactooligosaccharides | GOS | galactose | glucose, galactose | lactose |

TABLE 5

| Test of different mineral acids and acetic acid as the reaction medium for glucose glycosylation to gluco-oligosaccharides (GlOS) | | | | | | |
| --- | --- | --- | --- | --- | --- | --- |
| mineral acid | chemical formula | pKa | acid concentration (wt %) | reaction condition[a] | glycosylation [b] | reason |
| acetic acid | $CH_3OOH$ | 4.76 | 90 | 70° C., 10 min | no | limited glucose solubility |
| boric acid | $H_3BO_3$ | 9.27 | ~20 | 70° C., 10 min | no | low acid concentration, weak acidity |
| phosphoric acid | $H_3PO_4$ | 2.16 | 85 | 70° C., 10 min | yes | — |
| nitric acid | $HNO_3$ | −1.3 | 69-71 | 25° C., 3 h | no | strong oxidative ability |
| sulfuric acid | $H_2SO_4$ | −3 | 60-90 | 70° C., 10 min | yes | — |
| hydrochloric add | HCl | −6 | 37 | 70° C., 10 min | no | Acid concentration is too low for glycosylation (dehydration) |

Note:
[a]glycosylation was conducted at 30 w/w % initial glucose; Since nitric acid is easily decomposed to nitrogen oxides under thermal and light condition, the glycosylation was tested under room temperature without light;
[b] if no disaccharides (isomaltose, gentiobiose) was detected after glycosylation, the acid was considered to be not effective.

TABLE 6-continued

| | Abbrevi- | | | |
|---|---|---|---|---|
| | Synthesis of oligosaccharides from various substrates using concentrated sulfuric acid | | | |
| Target oligosaccharides | ation | substrate 1 | substrate 2 | substrate 3 |
| fructooligosaccharides | FOS | fructose | glucose, fructose | sucrose |
| mannooligosaccharides | MOS | mannose | — | — |
| xylooligosaccharides | XOS | xylose | — | — |
| arabinooligosaccharides | AOS | arabinose | — | — |

Example 12: Characterization of GlOS Synthesized in Concentrated $H_2SO_4$ i. Molecular Weight

Figure 19:
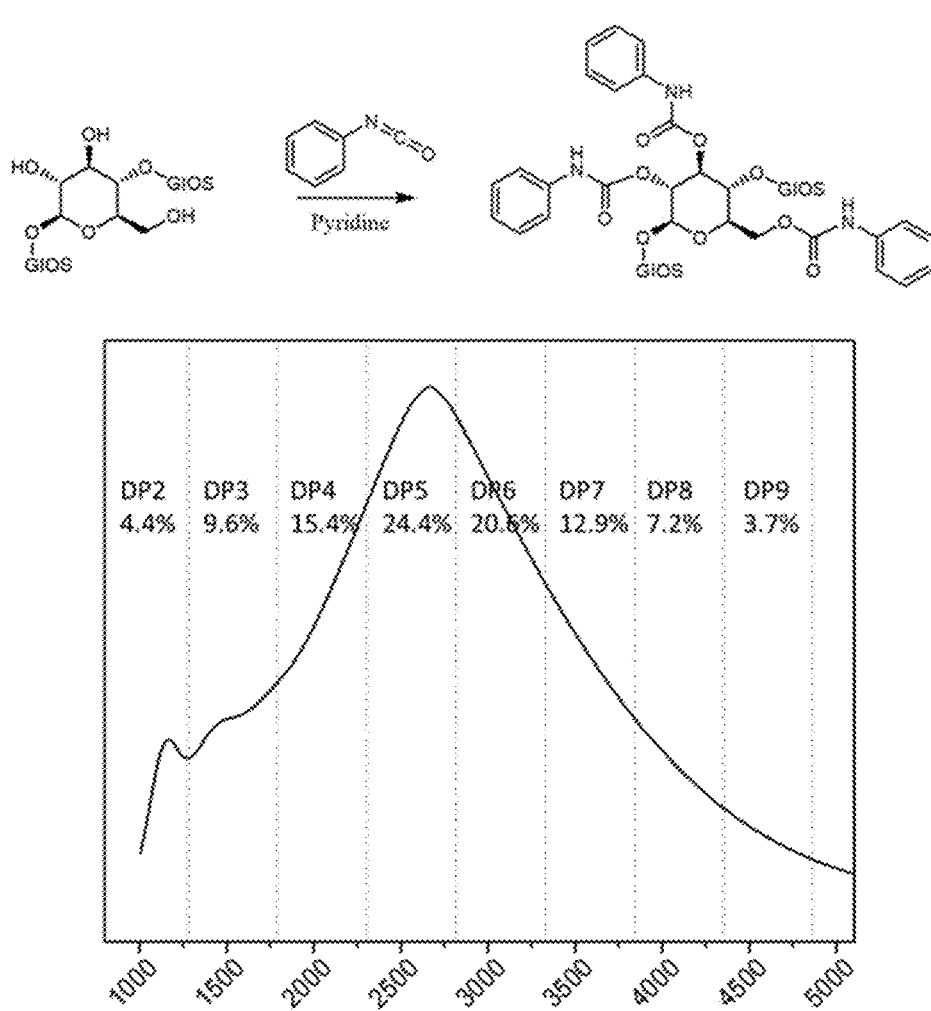
FIG. 19 shows a GPC chromatogram of derivatized GlOS. The glycosylation condition was conducted at 50 wt % initial glucose concentration, 76 wt % $H_2SO_4$, at 50° C. for 15 min.

The GlOS synthesized in the concentrated $H_2SO_4$ was a mixture of oligosaccharides with different lengths, and the average DP of GlOS was estimated by GPC. As shown in FIG. 19, the GlOS consisted of saccharides in a DP range of 2-10, with the average DP of 5.3, indicating the majority of GlOS being penta-saccharides (24.4%), hexa-saccharides (20.6%) and tetrasaccharides (15.4%). It meets the length requirement of prebiotic oligosaccharides, which is mostly $3 \leq DP \leq 10$.

TABLE 7

Effect of glycosylation condition on the average DP and DP percentage of GlOS

| | | | DP percentage (%) | | | | | | | |
|---|---|---|---|---|---|---|---|---|---|---|
| GlOS | Condition | average DP | DP 2 | DP 3 | DP 4 | DP 5 | DP 6 | DP 7 | DP 8 | DP 9 |
| 1 | 90° C., 5 min | 5.4 | 0.4 | 4.0 | 11.1 | 31.2 | 24.4 | 14.0 | 8.0 | 4.4 |
| 2 | 70° C., 5 min | 3.4 | 19.9 | 20.8 | 10.8 | 15.7 | 14.9 | 9.9 | 5.3 | 2.2 |
| 3 | 50° C., 5 min | 3.1 | 19.1 | 29.7 | 22.5 | 9.5 | 6.0 | 4.3 | 3.4 | 2.8 |
| 4 | 30° C., 5 min | 2.3 | 51.5 | 39.2 | 8.1 | 1.1 | — | — | — | — |
| 5 | 50° C., 10 min | 4.4 | 6.1 | 11.3 | 15.8 | 22.5 | 19.8 | 12.5 | 6.8 | 3.5 |
| 6 | 50° C., 15 min | 4.7 | 4.4 | 9.6 | 15.4 | 24.4 | 20.5 | 12.9 | 7.2 | 3.7 |
| 7 | 60% $H_2SO_4$ | 3.2 | 18.9 | 36.3 | 23.4 | 15.1 | 5.4 | 0.9 | 0.4 | — |
| 8 | 68% $H_2SO_4$ | 3.8 | 10.6 | 19.4 | 20.6 | 20.9 | 14.3 | 7.7 | 3.8 | 1.8 |
| 9 | 76% $H_2SO_4$ | 4.6 | 5.1 | 9.1 | 13.9 | 21.9 | 20.9 | 14.2 | 8.3 | 4.4 |
| 10 | 84% $H_2SO_4$ | 5.0 | 1.6 | 7.9 | 15.3 | 24.2 | 22.8 | 15.3 | 8.4 | 3.7 |

Note:
initial glucose concentration 50 wt %; for entry 1-6, 76% $H_2SO_4$

Figure 20:
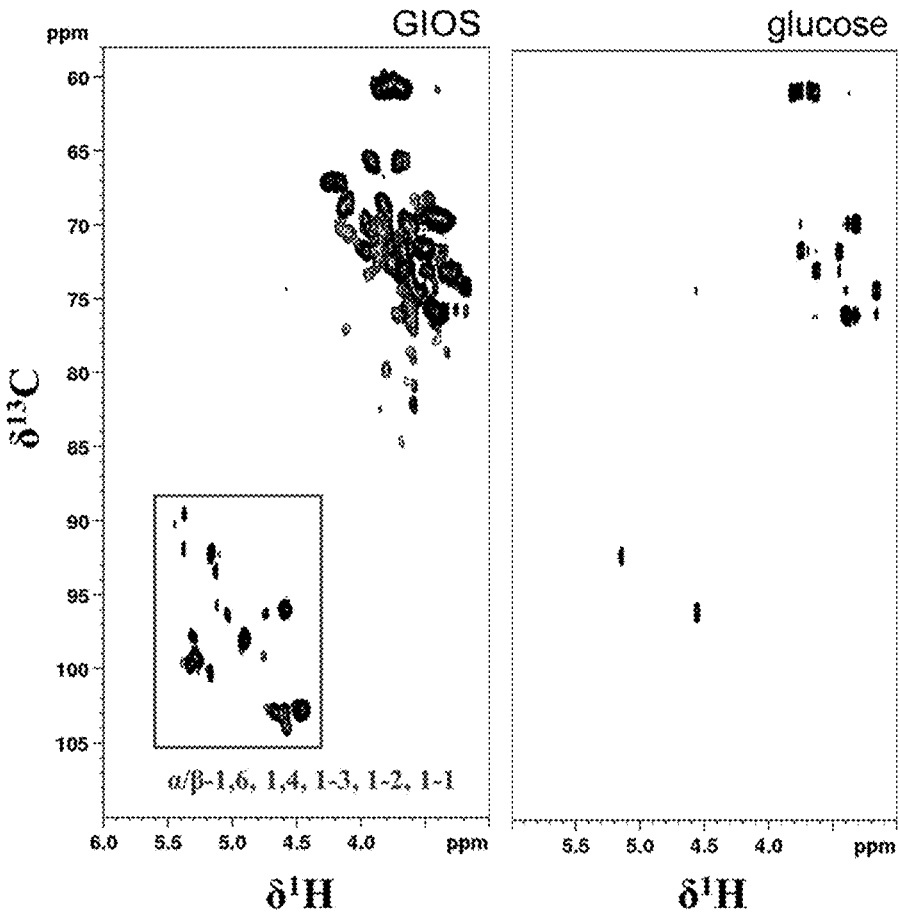
FIG. 20 shows a $^1$H-$^{13}$C HSQC NMR of the GlOS vs. pure glucose. The glucose glycosylation to GlOS was conducted at 50 wt % initial glucose concentration, 76 wt % $H_2SO_4$, at 50° C. for 15 min.

The effect of glycosylation condition on the DP of resultant GlOS was shown in Table 7. For entry 1-4, the average DP of GlOS increased from 2.3 to 5.4 when reaction temperature was increased from 30 to 90° C., which indicated that higher temperature favored the formation of longer oligosaccharides. For entry 3, 5, 6, extending reaction time from 5 to 15 min at 50° C. increased the average DP of GlOS from 3.1 to 4.7. Increasing the $H_2SO_4$ concentration also increased the average DP of GlOS (entry 7-10).

ii. Glycosyl Linkages $^1H$-$^{13}C$ HSQC NMR was conducted to study the regio- and stereo-selectivity of GlOS synthesized in concentrated $H_2SO_4$. As shown in FIG. 20, compared with glucose, there were more crosspeaks showed in the anomeric proton region ($^1H$ 4.3-5.5 ppm, $^{13}C$ 88-105 ppm) for GlOS, which meant that there are various glycosyl linkages formed in GlOS, including different regio- and stereo-isomers ($\alpha/\beta$-1,6, 1-4, 1-3, 1-2, 1-1). GlOS synthesized from concentrated $H_2SO_4$ is expected to have a prebiotic effect as human beings only have the digestive enzymes to break down $\alpha$-1,4 linkages (present in starch).

Example 13: Separation of Acid, Monosaccharides from Oligosaccharides i. Nanofiltration

After the glycosylation reaction in concentrated $H_2SO_4$, there are unreacted monosaccharides like glucose and galactose, which are not prebiotics. So, it is desirable to separate $H_2SO_4$ and non-prebiotic monosaccharides from the prebiotic oligosaccharides. The recovered acid and monosaccharides can be reused for next batch glycosylation. Nanofiltration (NF) is increasingly used in the food and biotechnology industry for purification and concentration of streams, with the advantages of being simple, low-cost, and eco-efficient. In order to seize this potential, a preliminary separation of $H_2SO_4$, monosaccharides from oligosaccharides by nanofiltration was studied.

Figure 21A:
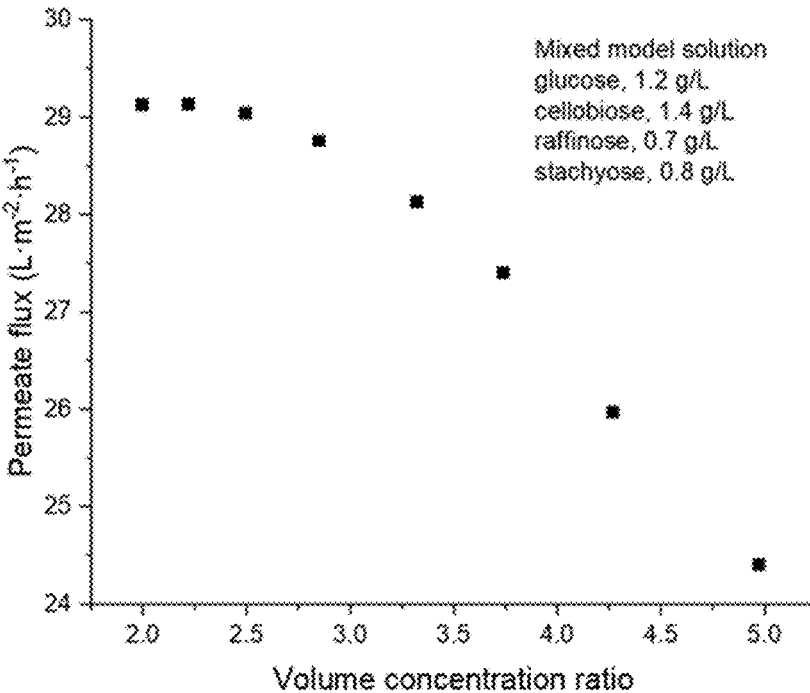
FIGS. 21A-21B show nanofiltration of mixed model solution (saccharides of DP 1-4) using XN45 membrane (300-500 Da) at 3.45 bar, 20° C.

First, the nanofiltration of a model solution (not acidic) containing mono-, di-, tri- and tetra-saccharide (glucose, cellobiose, raffinose, and stachyose, respectively) was studied. As shown in FIG. 21A, the permeate flux gradually decreased as the volume concentration ratio ($V_{initial}$/$V_{retentate}$, VCR) increased, which was attributed to the increase of saccharides concentration in the retentate. The observed rejection values ($R_{obs}$) of each saccharide was shown in FIG. 21B. The initial $R_{obs}$ of glucose was 0.48, and cellobiose, raffinose, stachyose had $R_{obs}$ higher than 0.8. As the nanofiltration proceed (VCR increased), the $R_{obs}$ of each saccharide decreased and finally (VCR=5) glucose and cellobiose all passed membrane, while the $R_{obs}$ of raffinose and stachyose was around 0.4. For the best removal of glucose, VCR should be around 3-3.5, where over 60% cellobiose, and over 80% raffinose and stachyose could be retained. The result in FIG. 21 indicated the potential of using nanofiltration to separate monosaccharide from the rest of oligosaccharides.

Figure 22A:
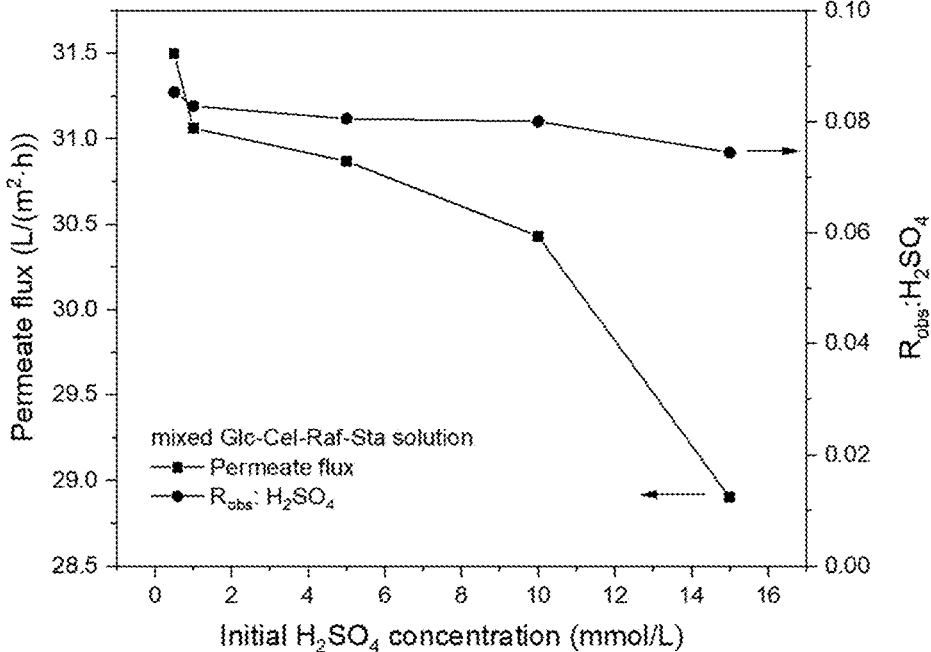
FIGS. 22A-22B show the effect of initial $H_2SO_4$ concentration on the nanofiltration of mixed model solution using XN45 membrane at 3.45 bar, 20° C.
Figure 22B:
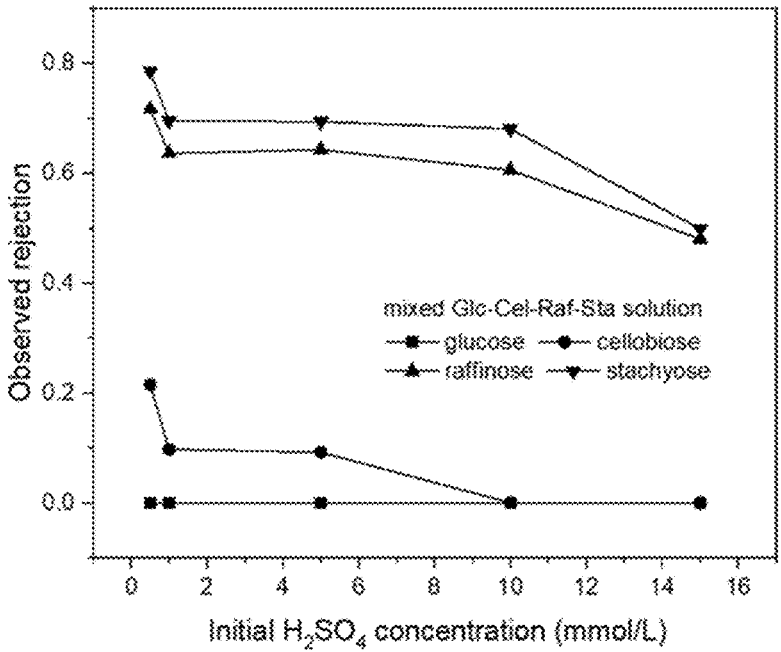

The effect of initial $H_2SO_4$ concentration (0.5-15 mmol/L) (pH 3.0-1.5) on the nanofiltration of mixed model solution was shown in FIG. 22. In FIG. 22A, the permeate flux of the model solution decreased with the initial $H_2SO_4$ concentration, and the $R_{obs}$ of $H_2SO_4$ remained around 0.08 which meant over 99% $H_2SO_4$ permeated the membrane.

Figure 21B:
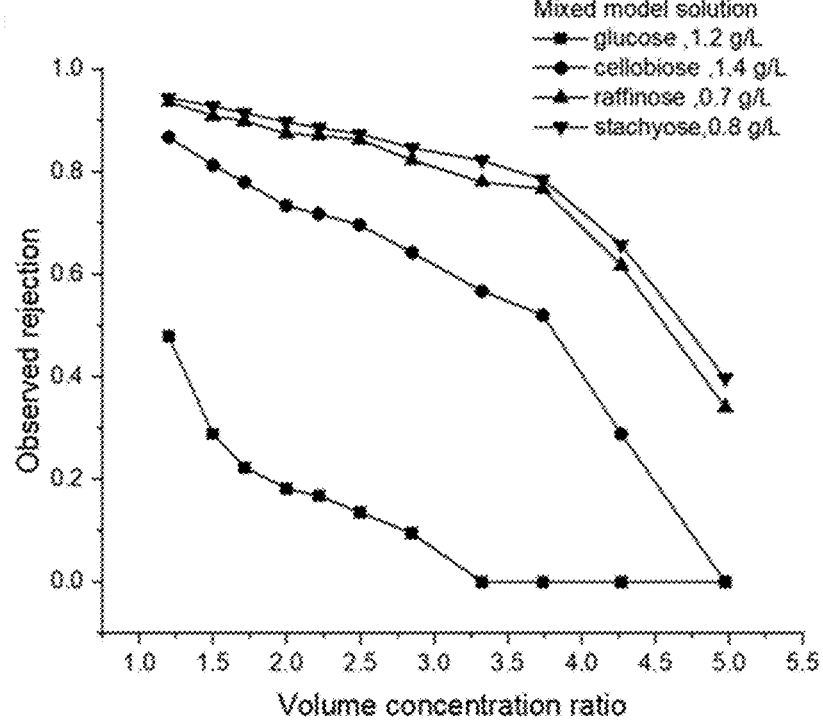

From FIG. 21B, when initial $H_2SO_4$ was 0.5 mmol/L, the $R_{obs}$ of glucose, cellobiose, raffinose and stachyose was 0, 0.22, 0.72, and 0.79. When initial $H_2SO_4$ increased to 15 mmol/L, the $R_{obs}$ of glucose, cellobiose decreased to 0 while the $R_{obs}$ of raffinose and stachyose decreased to 0.48 and 0.50, respectively. This indicated that higher acid concentration disfavors the separation, which lost more high-DP components.

Other Potential Separation Methods

The separation of $H_2SO_4$ and non-prebiotic monosaccharides from the rest prebiotic oligosaccharides can be achieved by other methods such as adsorption chromatography on charcoal, ion-exchange chromatography using strong cationic exchange resins, and low-pressure gel permeation chromatography (preparative). These will be investigated in the following studies.

Example 14: Oligosaccharide Synthesis by Simultaneous Hydrolysis and Glycosylation The simultaneous hydrolysis and glycosylation of corn stover and the model mixture of Avicel and xylan in concentrated $H_2SO_4$ was studied, and the result is shown in Table 8. The oligosaccharides can be formed directly from hydrolysis of polysaccharides, or from the glycosylation of the hydrolyzed monosaccharides like glucose and xylose, or from the glycosylation between the oligosaccharides and/or monosaccharides from the hydrolysis of polysaccharides (cellulose and/or hemicellulose) of the corn stover. The residual solid content was measured by gravity methods, and the mass yield of oligosaccharides were determined by the post hydrolysis methods.

30 product of glucose, was detected with a yield around 1-2%. The oligosaccharides from pentoses (xylose and arabinose) showed a yield in the range 11.4-35.5%. The yield of monosaccharides (glucose and xylose mainly) can be suppressed by increasing the substrate content. Side-products HMF and furfural derived from degradation of glucose and xylose, respectively, were also detected, but the yield was minimal under the reaction condition.

For entry 4-5, the mixture of Avicel and xylan was also studied. The yield of gluco-oligosaccharides and xylo-oligosaccharides was very similar to that of corn stover (entry 3 and 4). This indicated that lignin in corn stover may not affect the hydrolysis and glycosylation very much. The result in Table 1 showed that lignocellulosic biomass can be a potential raw material to prepare prebiotic oligosaccharides.

Experimental Notes: (a) corn stover composition: 39.9% glucan, 23.7% xylan, lignin 19.1%, arabinan 2.3%, galactan 0.9%; the mass ratio of Avicel to xylan was set to monitor that in corn stover; (b) substrate content is calculated as the ratio of substrate mass to the total mass of reaction mixture (substrate and $H_2SO_4$); (c) for corn stover, oligosaccharides from hexoses

TABLE 8

Simultaneous hydrolysis and glycosylation (SHG) of corn stover, mixed Avicel and xylan in concentrated $H_2SO_4$

| | | Reaction condition | | | |
|---|---|---|---|---|---|
| Entry | Substrate | temp. (° C.) | time (min) | $H_2SO_4$ (wt %) | substrate content (wt %) |
| 1 | Corn | 50 | 20 | 72 | 5 |
| 2 | stover | | 10 | | 5 |
| 3 | | | 10 | | 10 |
| 4 | Avicel + | | 10 | | 10 |
| 5 | xylan (1.63:1, w/w) | | 10 | | 20 |

| Entry | Residual solid (w/w %) | Residual glucose (%) | Residual xylose (%) | Oligosaccharides from hexoses (mass %) | Oligosaccharides from pentoses (mass %) |
|---|---|---|---|---|---|
| 1 | 20.6 | 20.9 | 20.0 | 25.4 | 11.4 |
| 2 | 19.1 | 17.9 | 22.1 | 44.8 | 19.1 |
| 3 | 19.1 | 12.1 | 16.2 | 59.5 | 35.5 |
| 4 | 1.5 | 10.0 | 14.6 | 60.7 | 30.2 |
| 5 | 1.5 | 5.5 | 9.1 | 43.9 | 30.4 |

| | Isomaltose | Side-products (%) | |
|---|---|---|---|
| Entry | yield (%) | HMF | furfural |
| 1 | 1.7 | 0.021 | 1.087 |
| 2 | 1.7 | 0.023 | 0.860 |
| 3 | 1.1 | 0.017 | 0.582 |
| 4 | 1.3 | 0.005 | 0.619 |
| 5 | 1.1 | 0.002 | 0.321 |

For entry 1-3, the residual solid content was 19-20%, which was very close to the lignin content in corn stover. This indicated that cellulose and hemicellulose in corn stover should be converted near completely. The total oligosaccharides yield from hexoses (glucose and galactose) was 25.4-59.5%. Isomaltose, which is the glycosylation $$(mass \%) = \frac{\substack{Mass\ (glucose + galactose,\ post\ hydrolysis) - \\ Mass\ (glucose + galactose,\ after\ glycosylation)}}{Mass(glucan + galactan) \times \frac{180}{162}}$$

-continued for corn stover, oligosaccharides from pentoses (mass %) =

$$\frac{\text{Mass(xylose + arabinose, post hydrolysis)} - \text{Mass(xylose + arabinose, after glycosylation)}}{\text{Mass(xylan + arabinan)} \times \frac{150}{132}};$$

(d) for Avicel + xylan, oligosaccharides from hexoses (mass %) =

$$\frac{\text{Mass(glucose, post hydrolysis)} - (\text{glucose, after glycosylation})}{\text{Mass(Avicel)} \times \frac{180}{162}}$$

for Avicel + xylan, oligosaccharides from pentoses (mass %) =

$$\frac{\text{Mass(xylose, post hydrolysis)} - \text{Mass(xylose, after glycosylation)}}{\text{Mass(xylan)} \times \frac{150}{132}}$$

(e) isomaltose yield = $\dfrac{\text{Mass (isomaltose, after glycosylation)}}{\text{Mass(glucan)} \times \frac{180}{162}}$ (f) HMF yield = $\dfrac{\text{Mass (HMF, after glycosylation)}}{\text{Mass(glucan)} \times \frac{180}{162}}$;

furfural yield = $\dfrac{\text{Mass (furfural, after glycosylation)}}{\text{Mass(xylan)} \times \frac{180}{162}}$.

Example 15: Synthesis of Oligosaccharides from Simple Sugars in Concentrated Phosphoric Acid A. Glucose Glycosylation to Gluco-Oligosaccharides (GlcOS)

Figure 23A:
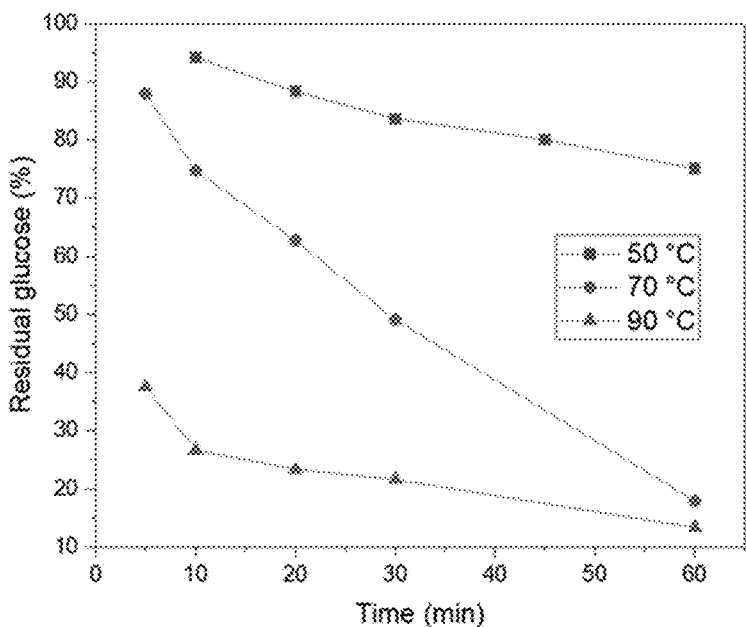
FIGS. 23A-23D show the synthesis of gluco-oligosaccharides (GlcOS) via glucose glycosylation in concentrated phosphoric acid (85% $H_3PO_4$, w/w) at 50, 70, 90° C. for 5-60 min.
Figure 23B:
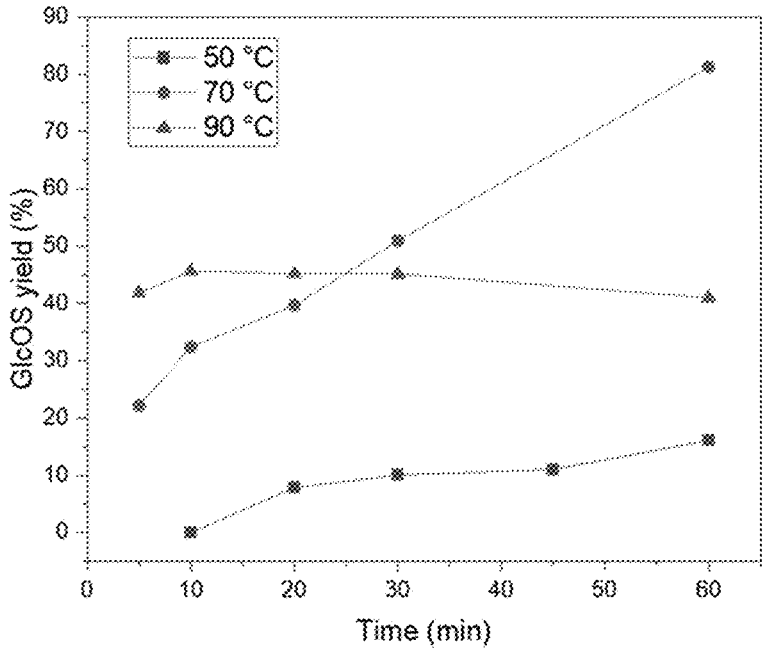
Figure 23C:
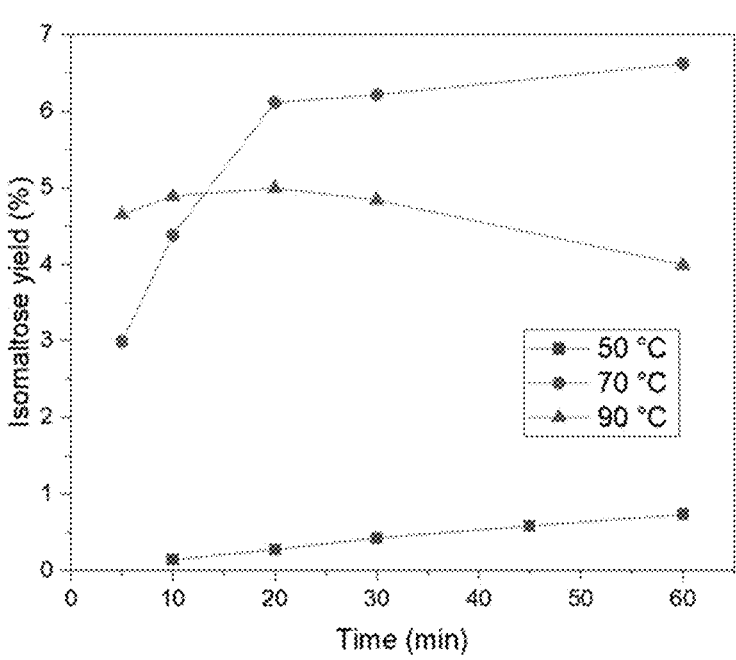
Figure 23D:
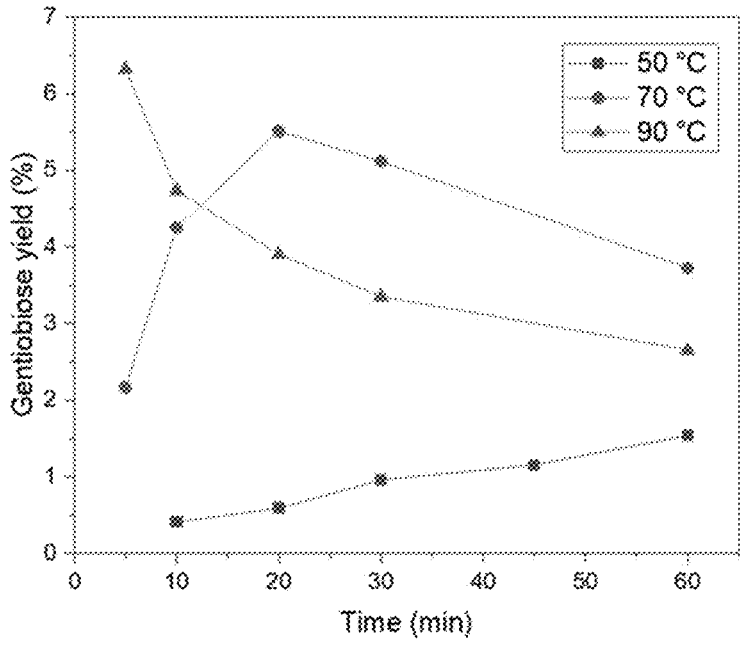

Synthesis of gluco-oligosaccharides (GlcOS) was studied using concentrated phosphoric acid (PA, 85% $H_3PO_4$) and 20% initial glucose loading (glucose around 420 g/L) under three different temperatures (50, 70, 90° C.), and the result was shown in FIG. 23A-23D. At 50° C., glucose conversion in concentrated PA was low because there was still 75% glucose remaining unreacted after 60 min reaction (FIG. 23A). Higher temperatures (70 or 90° C.) accelerated glucose conversion, and over 60% glucose was converted within 5 min at 90° C. Longer reaction times also lead to more glucose conversion, as there was less than 20% glucose remaining unreacted after 60 min. From FIG. 23B, the GlcOS yield at 50° C. was less than 20% due to low glucose conversion. At 70° C., there was an obvious increase in the GlcOS yield which ascended from 22% to the maximum of 81% when reaction time increased from 5 to 60 min. When the temperature was further elevated to 90° C., the GlcOS yield further increased within 20 min but remained unchanged when the reaction extended to 60 min. This was mainly because more side-products including 5-hydroxymethylfurfural, formic acid, levulinic acid are formed at high temperatures and long reaction times (data not shown). Isomaltose (IM, D-Glcp-α-(1→6)-D-Glcp) and gentiobiose (GB, D-Glcp-β-(1→6)-D-Glcp) are disaccharide intermediates during glucose glycosylation, and their yield was shown in FIG. 23C and FIG. 23D, respectively. At 50° C., the yield of IM and GB both slightly increased with reaction time, which reached 0.7% and 1.5% at 60 min. At 70° C., an initial increase was observed for both IM and GB, but a longer reaction time caused a slower increase for IM and a decrease for GB. While at 90° C., the IM yield showed a slight decrease (5.0% to 4.0%) and the GB yield decreased dramatically (6.3% to 2.7%). Overall, the above result proved that concentrated PA is sufficiently dehydrative to favor the glucose glycosylation to produce the GlcOS with a satisfactory yield (81%) after reaction at 70° C. for 60 min. Compared with the result from concentrated sulfuric acid (SA), it is concluded that the dehydration ability of concentrated PA is weaker than concentrated SA, and therefore a higher concentration (85% $H_3PO_4$ versus 76% $H_2SO_4$) and longer reaction time (70° C., 60 min for PA, 70° C., 20 min for SA) would be required to achieve a similar GlcOS yield.

Figure 24:
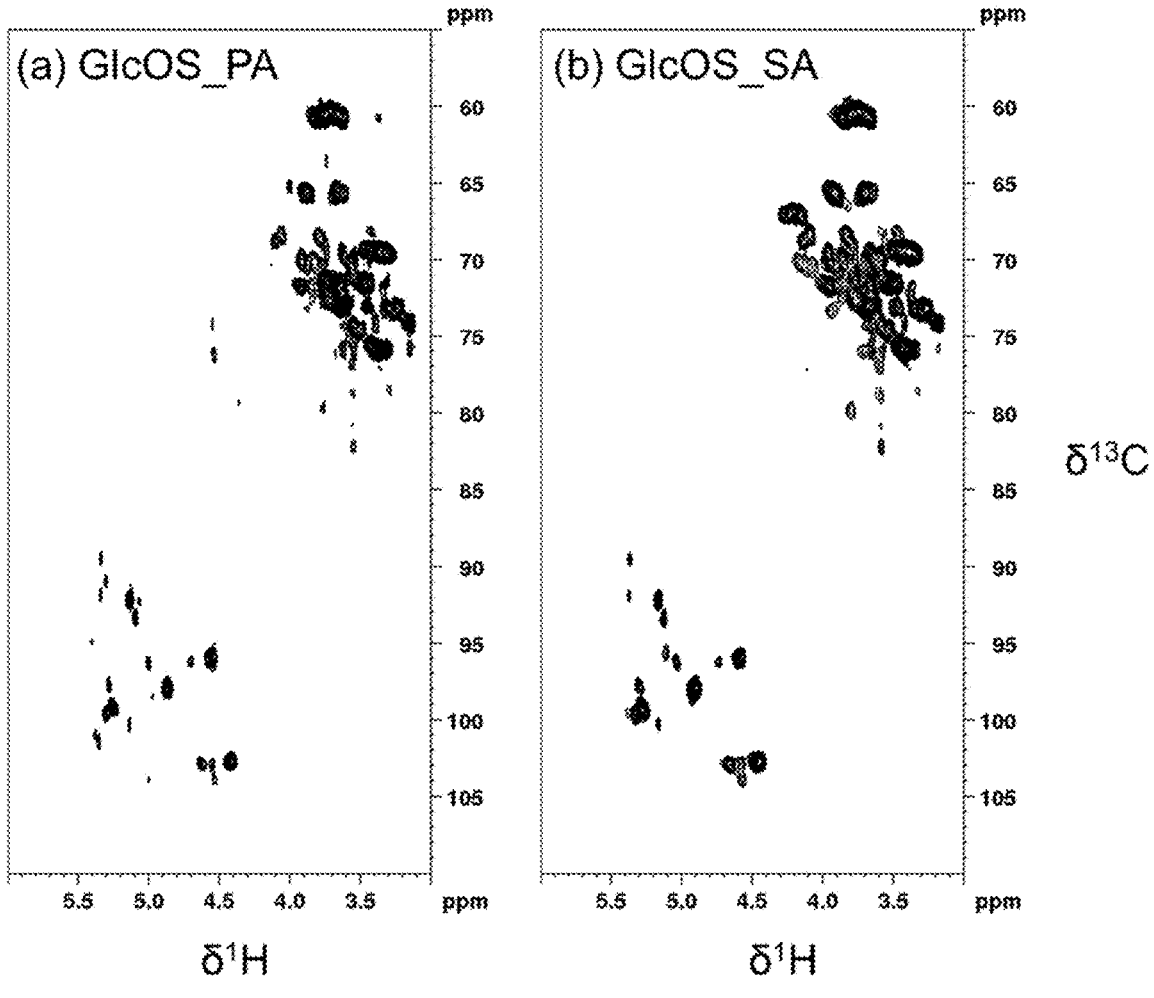
FIG. 24 shows 2D $^1$H-$^{13}$C HSQC NMR analysis of the GlcOS synthesized from concentrated phosphoric acid (GlcOS_PA) versus that from concentrated sulfuric acid (GlcOS_SA).

The glycosidic linkages in the GlcOS synthesized in concentrated PA (GlcOS_PA) were characterized by $^1H$-$^{13}C$ HSQC NMR, and compared with that synthesized in concentrated SA (GlcOS_SA). The anomeric $^1H$ and $^{13}C$ contours of different glycosyl reducing residues in the GlcOS (-(1→x)-D-Glcp) provide signature information about the formed linkages, which showed up in $\delta^1H$ 5.5-4.0 ppm outside the bulky alkyl proton region ($\delta^1H$ 4.0-3.0 ppm). As shown in FIG. 24, for both GlcOS_PA and GlcOS_SA, there were multiple contours in the anomeric region indicating that there are different glycosidic linkages formed including α/β-(1→6), α/β-(1→4), α/β-(1→3), α/β-(1→2), and (1→1) (α, α-, α, β-, β, β-). This again demonstrated that both PA and SA are effective reaction mediums for GlcOS synthesis, and multiple linkages are as expected because all the available hydroxyl groups in the glucose are reactive towards glycosylation. For GlcOS_PA, the contour areas were quite different from that in the GlcOS_SA, which suggested that different concentrated acids may result in different linkage preferences in the formed GlcOS.

B. Xylose Glycosylation to Xylo-Oligosaccharides (XOS)

TABLE 9

Synthesis of xylo-oligosaccharides (XOS) from xylose glycosylation in concentrated phosphoric acid (85% $H_3PO_4$, w/w)

| Entry | Temp. (° C.) | Time (min) | Residual xylose (%) | XOS yield (%) | Furfural yield (%) |
|---|---|---|---|---|---|
| 1 | 50 | 10 | 55 | 45 | 0.1 |
| 2 | 50 | 20 | 47 | 53 | 0.2 |
| 3 | 50 | 30 | 41 | 59 | 0.3 |
| 4 | 50 | 60 | 31 | 68 | 0.5 |
| 5 | 70 | 5 | 34 | 64 | 0.6 |
| 6 | 70 | 10 | 27 | 71 | 1.4 |
| 7 | 70 | 20 | 25 | 69 | 2.2 |
| 8 | 70 | 30 | 24 | 66 | 2.7 |

Note:
The initial xylose loading is 20% (w/w) and the concentration was 420 g/L.

Since concentrated PA proved to be effective for glucose glycosylation to GlcOS, we naturally think about whether it would be also effective for xylose, which is also an important platform sugar in lignocellulosic biorefinery. Table 9 showed the result of xylose glycosylation in concentrated PA under different synthetic conditions to produce xylooligosaccharides (XOS). From entry 1-4, at 50° C., an increase in XOS yield was observed (45-68%) from xylose glycosylation mainly because more xylose was converted as the reaction time increased from 10 to 60 min. When the temperature increased to 70° C. (entry 5-8), xylose conversion was faster, and only 24% xylose remained unreacted at 30 min (41% for 50° C.). But, no obvious increase was observed for XOS yield at 70° C., which reached a maximum of 71% at 10 min. Extending reaction time to 30 min resulted in more side-product furfural, and therefore XOS yield slightly decreased to 66%, which was no big difference compared to 50° C. In general, the XOS yield from xylose glycosylation in concentrated PA (maximum 71%) was lower than the GlcOS yield from glucose glycosylation (maximum 81%). This was probably because the reactivity of xylose towards glycosylation is weaker than glucose, and xylose is more easily degraded to furfural compared with glucose degradation to HMF. The glycosylation reactivity difference between xylose and glucose is likely because there is a primary hydroxyl group on of glucose (C6-OH), while for xylose, only secondary hydroxyl groups are present (C2-OH, C3-OH, C4-OH), thus glucose as an acceptor molecule, has more easily accessible C6-OH for glycosylation reaction.

Figure 25:
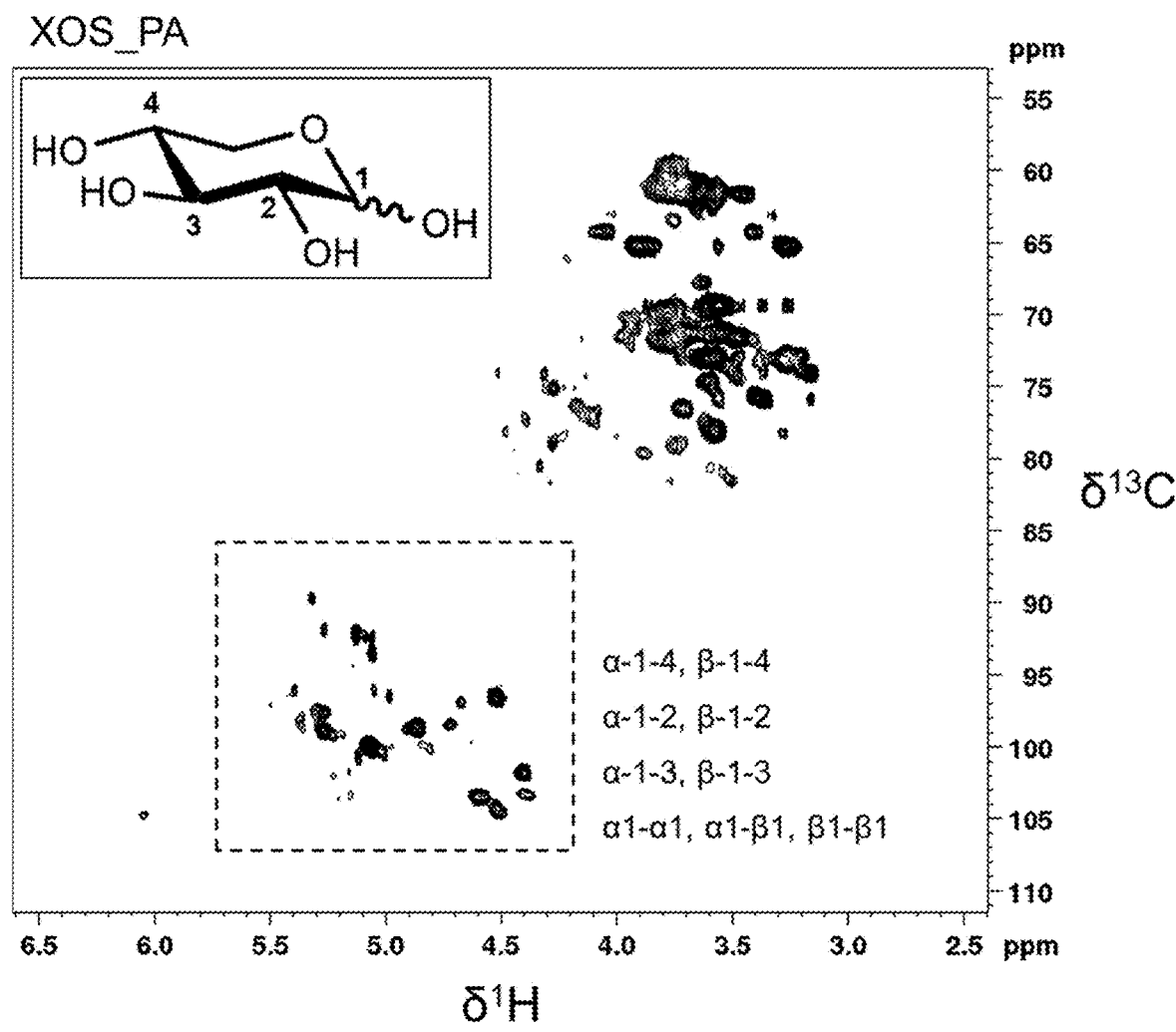
FIG. 25 shows 2D $^1$H-$^{13}$C HSQC NMR analysis of XOS synthesized from xylose glycosylation in concentrated phosphoric acid (XOS_PA).

The glycosidic linkages in the XOS from xylose glycosylation in concentrated phosphoric acid (XOS_PA) were also analyzed by 2D $^1$H-$^{13}$C HSQC NMR (FIG. 25). In a similar pattern as the GlcOS, the anomeric region showed multiple contours indicating that there are various glycosidic linkages formed in XOS including $\alpha/\beta$-(1→4), $\alpha/\beta$-(1→3), $\alpha/\beta$-(1→2), and (1→1) ($\alpha$, $\alpha$-, $\alpha$, $\beta$-, $\beta$, $\beta$-). This demonstrated that all the available hydroxyl groups in xylose are reactive, and the glycosylation occurs in a random manner which resulted in diverse regio- and stereo-chemistry of glycosidic linkages.

Example 16: Synthesis of Gluco- and Xylo-Oligosaccharides from Corn Stover in Concentrated Phosphoric Acid Previous studies have demonstrated that concentrated PA (85% $H_3PO_4$, w/w) can swell and dissolve cellulose in lignocellulose biomass, which increases the digestibility of cellulose in enzymatic hydrolysis to produce glucose.[1] For oligosaccharides synthesis, it is expected that concentrated PA can swell, dissolve and also hydrolyze the polysaccharides, i.e., cellulose and hemicellulose (mainly xylan or mannan), in lignocellulosic biomass, and the hydrolyzed oligosaccharides (e.g., cello-, xylo-oligosaccharides) and monosaccharides (mainly glucose, xylose or mannose) can act as substrates for acid-catalyzed glycosylation in concentrated PA to form gluco-oligosaccharides (GlcOS) and xylo-oligosaccharides (XOS) with new glycosidic linkages aiming for prebiotic function. Corn stover was chosen as the lignocellulosic feedstock for oligosaccharides synthesis because it has a relatively high content of polysaccharides (Table 10), including 36.5±0.6% cellulose and 22.2±0.7% xylan. For oligosaccharides synthesis, corn stover was premixed with 85% $H_3PO_4$ then reacted in an oil bath for a pre-determined time. After the reaction, the insoluble residues (mainly lignin and a small amount of unreacted polysaccharides) were removed by vacuum filtration and quantitated by gravity. The carbohydrates and side-products in the filtrate were analyzed by chromatographic methods to calculate the yield of oligosaccharides.

TABLE 10

Chemical composition of corn stover lignocellulosic biomass

| Chemical Composition | (%) |
|---|---|
| Moisture | 6.3 ± 0.1 |
| Water extractives | 10.6 ± 1.1 |
| Ash | 6.0 ± 0.1 |
| Cellulose | 36.5 ± 0.6 |
| Xylan | 22.2 ± 0.7 |
| Arabinan | 2.5 ± 0.1 |
| Galactan | 1.0 ± 0.1 |

TABLE 10-continued

Chemical composition of corn stover lignocellulosic biomass

| Chemical Composition | (%) |
|---|---|
| Acid-soluble lignin | 2.5 ± 0.0 |
| Acid-insoluble lignin | 15.8 ± 0.3 |

Note:
(1) Chemical composition analyzed by NREL standard method (NREL/TP-510-42618) based on the dry matter; (2) Acid-soluble lignin tested by absorptivity at 320 nm (30 L/g/cm).

Figure 26A:
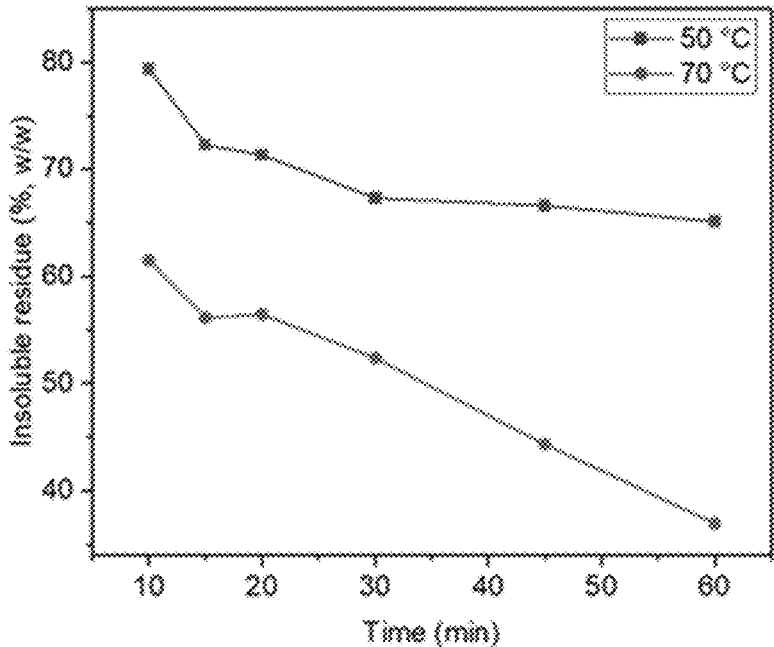
FIGS. 26A-C shows the synthesis of gluco-oligosaccharides (GlcOS) and xylo-oligosaccharides (XOS) from corn stover (initial loading 25%, w/w) using concentrated phosphoric acid (85% $H_3PO_4$, w/w) at 50° C., 70° C. (26A) mass yield of insoluble residues; (26B) mass yield of GlcOS, XOS; (26C) mass yield of glucose, xylose. Note: mass yield was calculated based on the total mass of corn stover.
Figure 26B:
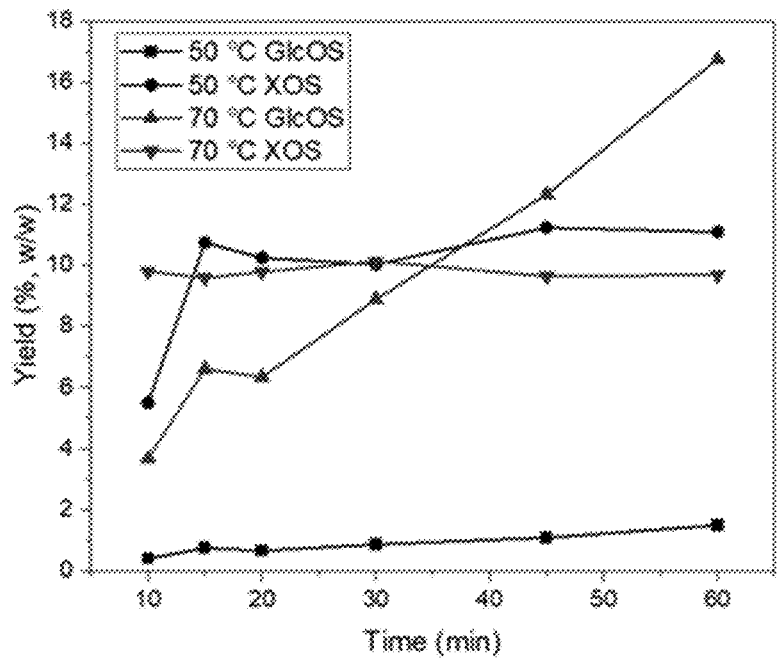
Figure 26C:
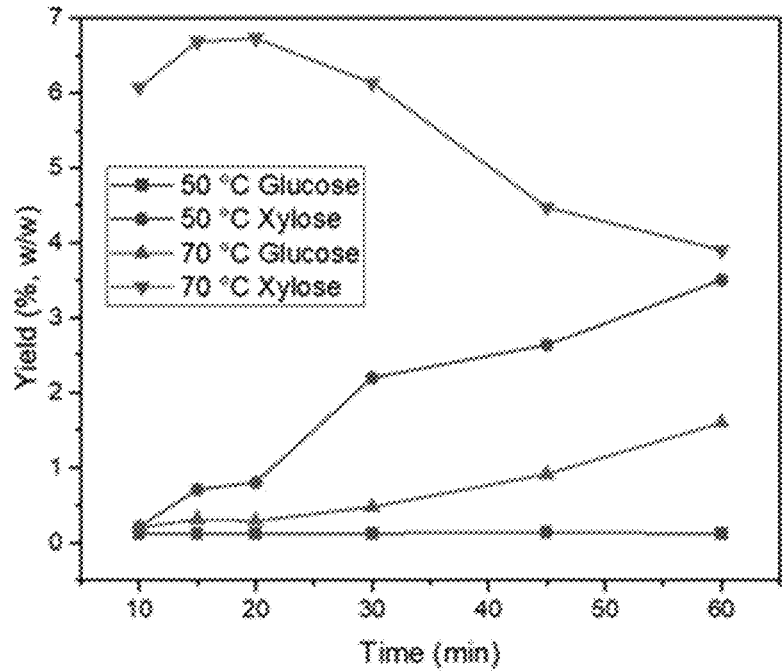

The synthesis of oligosaccharides (GlcOS and XOS) from corn stover was studied using 85% $H_3PO_4$ with 25% initial loading of corn stover, and the result was shown in FIGS. 26A-26C. As shown in FIG. 26A, the yield of insoluble residues gradually decreased with reaction time, and the decrease was more obvious for 70° C. which means high temperature favored the conversion of polysaccharides. After reaction at 70° C. for 60 min, there were still 37% insoluble residues (65% for 50° C.), which was larger than the total of lignin and ash (24.3%). This proved that polysaccharides in corn stover were not fully converted under the synthetic condition, and higher temperature and longer reaction time can be used to further accelerate the conversion of polysaccharides. From FIG. 26B, at 50° C., the GlcOS yield slightly increased with reaction time which reached 1.5% at 60 min, while the XOS yield showed a more obvious increase (6% to 11%). The yield of glucose was around 1% and the xylose yield grew from 0.2% to 3.5% at 50° C. (FIG. 26C), which was produced from the hydrolysis of cellulose and xylan, respectively. The low yield of GlcOS and glucose was mainly because cellulose is minimally converted in concentrated PA at 50° C. due to its highly crystalline nature compared with xylan. When the temperature was elevated to 70° C., higher GlcOS yield was observed compared to 50° C., and it also increased with reaction time (17% at 60 min. This was clearly due to more cellulose being converted at higher temperatures and longer time. While for XOS, the yield at 70° C. was comparable to that at 50° C. within 30 min, a longer reaction time resulted in the loss of XOS. In addition, higher temperatures also lead to more hydrolysis to xylose (6% at 10 min), but xylose decreased with extended time mainly because it was degraded to side-product furfural (0.2%-0.6% from 10 to 60 min). Overall, the maximum GlcOS yield from corn stover in concentrated PA was 17% (70° C., 60 min), and the maximum XOS yield (11%) was obtained at 50° C., 45 min. In general, the synthesis of oligosaccharides from corn stover is more challenging than from monosaccharides (glucose, xylose) because there are non-carbohydrate components in corn stover, and the polysaccharides are present in the recalcitrant matrix of lignocellulose which means lower accessibility by concentrated PA.

REFERENCES

1. N. Sathitsuksanoh, Z. Zhu and Y. H. P. Zhang, *Cellulose*, 2012, 19, 1161-1172.

ILLUSTRATIVE FEATURES

The present technology may include, but is not limited to, the features and combinations of features recited in the following numbered paragraphs, it being understood that the following paragraphs should not be interpreted as limiting the scope of the claims as appended hereto or mandating that all such features must necessarily be included in such claims:

Paragraph P1. A method comprising reacting a mixture comprising one or more types of monosaccharides, disaccharides, and/or polysaccharides and about 40 to about 98 wt % of dehydrating acid to provide a product predominantly comprising prebiotic oligosaccharides; wherein the mixture is reacted at a temperature of about 10° C. to about 160° C.

Paragraph P2. A method comprising reacting a mixture comprising about 1 wt % to about 90 wt % of one or more types of monosaccharides, disaccharides, and/or polysaccharides and an effective amount of a dehydrating acid to provide a product predominantly comprising prebiotic oligosaccharides; wherein the reacting occurs at a temperature of about 10° C. to about 160° C.

Paragraph P3. A method comprising reacting one or more types of monosaccharides, disaccharides, and/or polysaccharides thereof in a solution comprising an effective amount of sulfuric or phosphoric acid at a temperature sufficient to form a product predominantly comprising prebiotic oligosaccharides.

Paragraph P4. The method of Paragraphs P1 or P2, wherein the dehydrating acid is $H_2SO_4$ or $H_3PO_4$.

Paragraph P5. The method of any one of Paragraphs P1, P2, or P4 wherein the mixture comprises about 64 to about 90 wt % dehydrating acid.

Paragraph P6. The method of any one of Paragraphs P1, P2, P4 or P5, wherein the mixture comprises about 70 to about 80 wt % dehydrating acid.

Paragraph P7. The method of Paragraph P3, wherein the solution comprises about 64 to about 84 wt % sulfuric acid.

Paragraph P8. The method of Paragraph P3, wherein the solution comprises about 76 wt % sulfuric acid.

Paragraph P9. The method of Paragraph P3, wherein the solution comprises about 70 to about 80 wt % phosphoric acid.

Paragraph P10. The method of any one of Paragraphs P1 to P9, wherein the temperature is about 50° C. to about 90° C.

Paragraph P11. The method of any one of Paragraphs P1 to P9, wherein the temperature is about 25° C. to about 70° C.

Paragraph P12. The method of any one of Paragraphs P1 to P11, wherein the mixtures comprises glucose, fructose, galactose, xylose, levoglucosan, mannose, arabinose, sucrose, lactose, maltose, isomaltose, gentiobiose, cellobiose, trehalose, apiose, rhamnose, hydrolyzed starch, hydrolyzed cellulose, hydrolyzed lignocellulosic biomass, hydrolyzed dextrin, hydrolyzed dextran, or a combination of two or more thereof.

Paragraph P13. The method of any one of Paragraphs P1 to P11, wherein the mixture or solution comprises about 1 to about 50 wt % of the one or more monosaccharides and/or disaccharides.

Paragraph P14. The method of any one of Paragraphs P1 to P11, wherein the mixture or solution comprises about 30 to about 50 wt % of the one or more monosaccharides and/or disaccharides.

Paragraph P15. The method of any one of Paragraphs P1 to P11, wherein the mixture or solution comprises about 20 to about 70 wt % of the one or more monosaccharides and/or disaccharides.

Paragraph P16. The method of any one of Paragraphs P1 to P15, wherein the one or more monosaccharides and/or disaccharides and the acid are reacted for 1 minute to 60 minutes.

Paragraph P17. The method of any one of Paragraphs P1 to P15, wherein the one or more monosaccharides, disaccharides, or a combination thereof and the acid are reacted for 2 minutes to 30 minutes.

Paragraph P18. The method of any one of Paragraphs P1 to P17, wherein the prebiotic oligosaccharides of the product are selected from the group consisting of glucooligosaccharides (GlOS), fructooligosaccharides (FOS), galactooligosaccharides (GaOS), xylooligosaccharides (XOS), maltooligosaccharides, isomaltooligosaccharides (IMO), and mannooligosaccharides, cellooligosaccharides, pecticoligosaccharides (POS) and combinations of any two or more thereof.

Paragraph P19. The method of any one of Paragraphs P1 to P18, wherein the prebiotic oligosaccharides of the product contain one or more glycosidic bonds selected from the group consisting of $\alpha/\beta$-1,1, $\alpha/\beta$-1,2, $\alpha/\beta$-1,3, $\alpha$-1,4, and $\alpha/\beta$-1,6.

Paragraph P20. The method of any one of Paragraphs P1 to P19, wherein the prebiotic oligosaccharides of the product have a degree of polymerization of 3 to 10.

Paragraph P21. The method of Paragraph P20, wherein the mixture is reacted at a temperature of 50° C. to 70° C. and wherein the prebiotic oligosaccharides of the product have a degree of polymerization of 3.

Paragraph P22. The method of Paragraph P21, wherein the mixture is reacted at a temperature of 90° C. and wherein the prebiotic oligosaccharides of the product have a degree of polymerization of 4 to 7.

Paragraph P23. The method of any one of Paragraphs P1 to P22, further comprising purifying the product.

Paragraph P24. The method of Paragraph P23, wherein the product is purified using nanofiltration, adsorption chromatography on charcoal, ion-exchange chromatography, or low-pressure gel permeation chromatography.

Paragraph P25. The method of any one of Paragraphs P1-P24, wherein the mixture or solution comprises monosaccharides and/or disaccharides as the only source of sugar(s) therein.

Paragraph P26. The method of any one of Paragraphs P1-P11 and P13-P24, wherein the mixture or solution comprises polysaccharides as the only source of sugars therein.

Paragraph P27. The method of any one of Paragraphs P1-P26, wherein the one or more polysaccharides comprise cellulose, hemicellulose, corn stover, or a combination of two or more thereof.

EQUIVALENTS

While certain embodiments have been illustrated and described, a person with ordinary skill in the art, after reading the foregoing specification, can effect changes, substitutions of equivalents and other types of alterations to the methods and oligosaccharides of the present technology or derivatives, nutraceutical compositions, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conditions, starting materials, reagents, compounds, or compositions, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the phrase "consisting essentially of" will be understood to include those elements specifically recited and those additional elements that do not materially affect the basic and novel characteristics of the claimed technology. The phrase "consisting of" excludes any element not specified. The terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. More specifically, it will be understood that each use of terms such as "comprising," "consisting essentially of" or "consisting of", discloses and provides written description and support for the use any of the other terms with the same or any other embodiment described herein.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

The invention claimed is:

1. A method comprising reacting a mixture comprising about 1 wt % to about 90 wt % of one or more types of monosaccharides, disaccharides, and/or polysaccharides and about 64 to about 98 wt % of dehydrating acid to provide a product predominantly comprising prebiotic oligosaccharides; wherein the mixture is reacted at a temperature of about 10° C. to about 160° C.

2. The method of claim 1, wherein the one or more types of monosaccharides, disaccharides, and/or polysaccharides thereof is reacted in a solution comprising a dehydrating acid selected from sulfuric and phosphoric acid.

3. The method of claim 2, wherein the solution comprises about 64 to about 92 wt % sulfuric acid.

4. The method of claim 2, wherein the solution comprises about 70 to about 90 wt % phosphoric acid.

5. The method of claim 1, wherein the dehydrating acid is $H_2SO_4$ or $H_3PO_4$.

6. The method of claim 1, wherein the temperature is about 50° C. to about 90° C.

7. The method of claim 1, wherein the temperature is about 25° C. to about 70° C.

8. The method of claim 1, wherein the mixtures comprises glucose, fructose, galactose, xylose, levoglucosan, mannose, arabinose, sucrose, lactose, maltose, isomaltose, gentiobiose, cellobiose, trehalose, apiose, rhamnose, hydrolyzed starch, hydrolyzed cellulose, hydrolyzed lignocellulosic biomass, hydrolyzed dextrin, hydrolyzed dextran, or a combination of two or more thereof.

9. The method of claim 1, wherein the mixture comprises about 1 to about 50 wt % of the one or more monosaccharides and/or disaccharides.

10. The method of claim 1, wherein the mixture comprises about 20 to about 70 wt % of the one or more monosaccharides and/or disaccharides.

11. The method of claim 1, wherein the one or more monosaccharides and/or disaccharides and the acid are reacted for 1 minute to 60 minutes.

12. The method of claim 1, wherein the prebiotic oligosaccharides of the product are selected from the group consisting of glucooligosaccharides (GlOS or GlcOS), fructooligosaccharides (FOS), galactooligosaccharides (GaOS or GOS), xylooligosaccharides (XOS), maltooligosaccharides, isomaltooligosaccharides (IMO), and mannooligosaccharides, cellooligosaccharides, pecticoligosaccharides (POS) and combinations of any two or more thereof.

13. The method of claim 1, wherein the prebiotic oligosaccharides of the product contain one or more glycosidic bonds selected from the group consisting of (α, α)-1,1; (α, β)-1,1; (β, β)-1,1; α/⊕-1,2; α/β-1,3; α/β-1,4; and α/β-1,6.

14. The method of claim 1, wherein the prebiotic oligo-saccharides of the product have a degree of polymerization of 2 to 10.

15. The method of claim 14, wherein the mixture is reacted at a temperature of 50° C. to 70° C. and wherein the prebiotic oligosaccharides of the product have a degree of polymerization of about 3.

16. The method of claim 1, wherein the mixture is reacted at a temperature of 90° C. and wherein the prebiotic oligo-saccharides of the product have a degree of polymerization of about 4 to 7.

17. The method of claim 1, further comprising purifying the product.

18. The method of claim 17, wherein the product is purified using nanofiltration, adsorption chromatography on charcoal, ion-exchange chromatography, or low-pressure gel permeation chromatography.

19. The method of claim 1, wherein the one or more polysaccharides comprise cellulose, hemicellulose, corn sto-ver, or a combination of two or more thereof.

20. The method of claim 1, wherein the mixtures com-prises glucose, fructose, galactose, xylose, levoglucosan, mannose, arabinose, sucrose, lactose, maltose, isomaltose, gentiobiose, cellobiose, trehalose, apiose, rhamnose, or a combination of two or more thereof.

* * * * *